US007309315B2

(12) United States Patent
Kullok et al.

(10) Patent No.: US 7,309,315 B2
(45) Date of Patent: Dec. 18, 2007

(54) APPARATUS, METHOD AND COMPUTER PROGRAM PRODUCT TO FACILITATE ORDINARY VISUAL PERCEPTION VIA AN EARLY PERCEPTUAL-MOTOR EXTRACTION OF RELATIONAL INFORMATION FROM A LIGHT STIMULI ARRAY TO TRIGGER AN OVERALL VISUAL-SENSORY MOTOR INTEGRATION IN A SUBJECT

(75) Inventors: Saul Kullok, London (GB); Jose R. Kullok, London (GB)

(73) Assignee: Epoch Innovations, Ltd., Dublin (IE)

( * ) Notice: Subject to any disclaimer, the term of this patent is extended or adjusted under 35 U.S.C. 154(b) by 1154 days.

(21) Appl. No.: 10/235,838

(22) Filed: Sep. 6, 2002

(65) Prior Publication Data

US 2004/0049124 A1 Mar. 11, 2004

(51) Int. Cl.
*A61B 13/00* (2006.01)
(52) U.S. Cl. .................................... 600/558
(58) Field of Classification Search ............... 600/558, 600/26, 27, 300; 128/898; 351/200, 201, 351/203, 209, 210, 222, 223, 237, 239; 434/112, 434/178, 236, 238
See application file for complete search history.

(56) References Cited

U.S. PATENT DOCUMENTS

| | | | |
|---|---|---|---|
| 2,099,516 A | 11/1937 | Hackett | |
| 3,893,450 A | 7/1975 | Ertl | |
| 3,900,034 A | 8/1975 | Katz et al. | |
| 3,944,654 A | 3/1976 | Moore | |
| 3,976,058 A | 8/1976 | Tidwell | |
| 4,090,311 A | 5/1978 | Lyons | |
| 4,123,853 A | 11/1978 | Dickensheet | |
| 4,173,832 A | 11/1979 | Chen et al. | |
| 4,201,224 A | 5/1980 | John | |
| 4,245,405 A | 1/1981 | Lien et al. | |

(Continued)

FOREIGN PATENT DOCUMENTS

CA 2012863 A1 9/1991

(Continued)

OTHER PUBLICATIONS

Gibson, J.J., *The Senses Considered as Perceptual Systems*, George Allen & Unwin Ltd., copy of entire book submitted (1966).

(Continued)

*Primary Examiner*—Max F. Hindenburg
*Assistant Examiner*—Brian Szmal
(74) *Attorney, Agent, or Firm*—Sterne, Kessler, Goldstein & Fox PLLC

(57) ABSTRACT

An apparatus, method and computer program product is presented to address early visual-sensory motor perception of a subject, where the method comprising the steps of: (1) controlling photic energetic parameters and/or photic perceptual attributes to trigger pre-attentive cuing or increase reactivity in magnocellular activity towards transient visual stimuli of the subject; and (2) generating a optical field comprising optical events based on said photic energetic parameters and said photic perceptual attributes, wherein said optical field transforms into a simple optical flow in the perceptual visual field of said subject. The photic energetic parameters may comprise light array energetic features, including one or more of wavelength, amplitude, intensity, phase, polarization, coherence, hue, brightness, and saturation.

212 Claims, 42 Drawing Sheets

U.S. PATENT DOCUMENTS

| | | |
|---|---|---|
| 4,273,538 A | 6/1981 | Ross |
| 4,282,864 A | 8/1981 | Pizer |
| 4,289,121 A | 9/1981 | Kupriyanovich |
| 4,302,193 A | 11/1981 | Haynes |
| 4,332,566 A | 6/1982 | Mazeski et al. |
| 4,379,699 A | 4/1983 | Nelson |
| 4,397,635 A | 8/1983 | Samuels |
| 4,454,886 A | 6/1984 | Lee |
| 4,474,186 A | 10/1984 | Ledley et al. |
| 4,580,574 A | 4/1986 | Gavish |
| 4,592,731 A | 6/1986 | Shifflett et al. |
| 4,632,126 A | 12/1986 | Aguilar |
| 4,661,074 A | 4/1987 | Walker |
| 4,738,269 A | 4/1988 | Nashner |
| 4,762,131 A | 8/1988 | Okuda |
| 4,776,323 A | 10/1988 | Spector |
| 4,902,274 A | 2/1990 | Gleeson, III |
| 4,906,193 A | 3/1990 | McMullen et al. |
| 4,930,504 A | 6/1990 | Diamantopoulos et al. |
| 4,979,902 A | 12/1990 | Morelle et al. |
| 5,001,632 A | 3/1991 | Hall-Tipping |
| 5,036,858 A | 8/1991 | Carter et al. |
| 5,046,494 A | 9/1991 | Searfoss et al. |
| 5,047,006 A | 9/1991 | Brandston et al. |
| 5,057,020 A | 10/1991 | Cytanovich |
| 5,076,281 A | 12/1991 | Gavish |
| 5,120,228 A | 6/1992 | Stahl et al. |
| 5,167,610 A | 12/1992 | Kitado et al. |
| 5,188,533 A | 2/1993 | Wood |
| 5,213,562 A | 5/1993 | Monroe |
| 5,256,067 A | 10/1993 | Gildea et al. |
| 5,265,598 A | 11/1993 | Searfoss et al. |
| 5,267,942 A | 12/1993 | Saperston |
| 5,273,433 A | 12/1993 | Kaminski et al. |
| 5,277,586 A | 1/1994 | Branch |
| 5,291,894 A | 3/1994 | Nagy |
| 5,299,125 A | 3/1994 | Baker et al. |
| 5,302,132 A | 4/1994 | Corder |
| 5,304,112 A | 4/1994 | Mrklas et al. |
| 5,343,871 A | 9/1994 | Bittman et al. |
| 5,365,935 A | 11/1994 | Righter et al. |
| 5,365,939 A | 11/1994 | Ochs |
| 5,366,377 A | 11/1994 | Miller |
| 5,387,104 A | 2/1995 | Corder |
| 5,404,444 A | 4/1995 | Billings |
| 5,420,653 A | 5/1995 | Mumford |
| 5,423,328 A | 6/1995 | Gavish |
| 5,429,513 A | 7/1995 | Diaz-Plaza |
| 5,465,729 A | 11/1995 | Bittman et al. |
| 5,474,081 A | 12/1995 | Livingstone et al. |
| 5,478,240 A | 12/1995 | Cogliano |
| 5,485,230 A | 1/1996 | Zimmerman |
| 5,511,980 A | 4/1996 | Wood |
| 5,529,498 A | 6/1996 | Cassily et al. |
| 5,543,867 A | 8/1996 | Mumford |
| 5,545,192 A | 8/1996 | Czeisler et al. |
| 5,546,943 A | 8/1996 | Gould |
| 5,562,719 A | 10/1996 | Lopez-Claros |
| 5,577,919 A | 11/1996 | Collins et al. |
| 5,584,698 A | 12/1996 | Rowland |
| 5,591,219 A | 1/1997 | Dungan |
| 5,613,498 A | 3/1997 | Yasushi et al. |
| 5,636,038 A | 6/1997 | Lynt et al. |
| 5,657,996 A | 8/1997 | Radgowski et al. |
| 5,662,117 A | 9/1997 | Bittman |
| 5,667,470 A | 9/1997 | Janata |
| 5,678,571 A | 10/1997 | Brown |
| 5,686,982 A | 11/1997 | Mumford |
| 5,687,291 A | 11/1997 | Smyth |
| 5,692,517 A | 12/1997 | Junker |
| 5,709,645 A | 1/1998 | Siever |
| 5,720,772 A | 2/1998 | Eckhouse |
| 5,725,472 A | 3/1998 | Weathers |
| 5,734,730 A | 3/1998 | Cho et al. |
| 5,743,744 A | 4/1998 | Cassily et al. |
| 5,762,611 A | 6/1998 | Lewis et al. |
| 5,769,641 A | 6/1998 | Lampotang et al. |
| 5,771,261 A | 6/1998 | Anbar |
| 5,772,508 A | 6/1998 | Sugita et al. |
| 5,782,825 A | 7/1998 | Anderson |
| 5,795,022 A | 8/1998 | Brown |
| 5,799,267 A | 8/1998 | Siegel |
| 5,800,337 A | 9/1998 | Gavish |
| 5,813,861 A | 9/1998 | Wood |
| 5,813,862 A | 9/1998 | Merzenich et al. |
| 5,820,379 A | 10/1998 | Hall et al. |
| 5,823,782 A | 10/1998 | Marcus et al. |
| 5,852,489 A | 12/1998 | Chen |
| 5,883,694 A | 3/1999 | Mumford |
| 5,895,363 A | 4/1999 | Preijde |
| 5,906,492 A | 5/1999 | Putterman |
| 5,911,581 A | 6/1999 | Reynolds et al. |
| 5,913,310 A | 6/1999 | Brown |
| 5,913,876 A | 6/1999 | Taylor et al. |
| 5,918,603 A | 7/1999 | Brown |
| 5,919,217 A | 7/1999 | Hughes |
| 5,938,531 A | 8/1999 | Yasushi et al. |
| 5,944,533 A | 8/1999 | Wood |
| 5,947,908 A | 9/1999 | Morris |
| 5,953,102 A | 9/1999 | Berry |
| 5,973,694 A | 10/1999 | Steele et al. |
| 5,974,262 A | 10/1999 | Fuller et al. |
| 5,983,129 A | 11/1999 | Cowan et al. |
| 5,997,304 A | 12/1999 | Wood |
| 6,004,135 A | 12/1999 | Trattner et al. |
| 6,009,397 A | 12/1999 | Siegel |
| 6,017,302 A | 1/2000 | Loos |
| 6,019,607 A | 2/2000 | Jenkins et al. |
| 6,022,222 A | 2/2000 | Guinan |
| 6,041,215 A | 3/2000 | Maddrell et al. |
| 6,045,363 A | 4/2000 | Phillips |
| 6,045,515 A | 4/2000 | Lawton |
| 6,056,549 A | 5/2000 | Fletcher |
| 6,062,863 A | 5/2000 | Kirksey et al. |
| 6,063,108 A | 5/2000 | Salansky et al. |
| 6,071,123 A | 6/2000 | Tallal et al. |
| 6,076,011 A | 6/2000 | Hoover |
| 6,081,743 A | 6/2000 | Carter et al. |
| 6,090,037 A | 7/2000 | Gavish |
| 6,120,297 A | 9/2000 | Morse, III et al. |
| 6,123,548 A | 9/2000 | Tallal et al. |
| 6,129,748 A | 10/2000 | Kamei |
| 6,146,147 A | 11/2000 | Wasowicz |
| 6,162,059 A | 12/2000 | Murphy et al. |
| 6,186,145 B1 | 2/2001 | Brown |
| 6,212,427 B1 | 4/2001 | Hoover |
| 6,213,956 B1 | 4/2001 | Lawton |
| 6,238,424 B1 | 5/2001 | Thiberg |
| 6,238,425 B1 | 5/2001 | Thiberg |
| 6,260,022 B1 | 7/2001 | Brown |
| 6,261,236 B1 | 7/2001 | Grimblatov |
| 6,299,632 B1 | 10/2001 | Jaillet |
| 6,339,725 B1 | 1/2002 | Naritoku et al. |
| 6,346,486 B2 | 2/2002 | Uochi et al. |
| 6,350,128 B1 | 2/2002 | Neuhaus |
| 6,358,056 B1 | 3/2002 | Jenkins et al. |
| 6,364,666 B1 | 4/2002 | Jenkins et al. |
| 6,382,791 B1 | 5/2002 | Strawderman et al. |
| 6,383,707 B1 | 5/2002 | Anderson et al. |
| 6,390,979 B1 | 5/2002 | Njemanze |
| 6,442,869 B2 | 9/2002 | Coomes |
| 6,443,572 B1 | 9/2002 | Lawson |
| 6,450,820 B1 | 9/2002 | Palsson et al. |
| 6,475,162 B1 | 11/2002 | Hu |

| | | |
|---|---|---|
| 6,517,351 B2 | 2/2003 | Spector |
| 6,565,853 B1 | 5/2003 | Jacobs |
| 6,623,427 B2 | 9/2003 | Mandigo |
| 6,632,174 B1 | 10/2003 | Breznitz |
| 6,639,582 B1 | 10/2003 | Shrader |
| 6,652,283 B1 | 11/2003 | Van Schaack et al. |
| 6,656,116 B2 | 12/2003 | Kim et al. |
| 6,687,535 B2 | 2/2004 | Hautala et al. |
| 6,743,164 B2 | 6/2004 | Airaudi et al. |
| 6,754,632 B1 | 6/2004 | Kalinowski et al. |
| 6,754,874 B1 | 6/2004 | Richman |
| 6,755,657 B1 | 6/2004 | Wasowicz |

FOREIGN PATENT DOCUMENTS

| | | |
|---|---|---|
| EP | 0 434 856 A1 | 7/1991 |
| EP | 1 024 327 A1 | 8/2000 |
| JP | 2-31768 | 2/1990 |
| JP | 11-164894 | 6/1999 |
| JP | 2001-170089 | 6/2001 |
| WO | WO 94 05202 A | 3/1994 |
| WO | WO 00/11397 A1 | 3/2000 |
| WO | WO 00/77760 A1 | 12/2000 |
| WO | WO 01/29799 A2 | 4/2001 |

OTHER PUBLICATIONS

Gibson, J.J., *The Ecological Approach to Visual Perception*, Lawrence Erlbaum Associates, ISBN 0-89859-958-X, copy of entire book submitted (1986).

Mace, W.M., "Ecologically Stimulating Cognitive Psychology: Gibsonian Perspectives," *Cognition and the Symbolic Processes*, Erlbaum, pp. 137-164 (1974).

Johansson, G., "On Theories for Visual Space Perception: A letter to Gibson," *Scandinavian Journal of Psychology*, vol. II, pp. 67-74 (1970).

Piaget, J., *The Origins of Intelligence in Children*, International Universities Press, Inc., copy of entire book submitted (1952).

Piaget, J., *The Construction of Reality in the Child*, Routledge & Kegan Paul Ltd., copy of entire book submitted (1954).

Piaget, J., *The Psychology of Intelligence*, Routledge & Kegan Paul Ltd., copy of entire book submitted (1950).

Auger, J., "Guidelines for Teachers, Parents and Learners," *Children's Written Language Difficulties, Assessment, and Management*, Routledge, pp. 147-169 (1993).

Frith, U., "Brain, Mind and Behaviour in Dyslexia," *Dyslexia: Biology, Cognition and Intervention*, Whurr, pp. 1-19 (1993).

Lovegrove, W. et al., "A Theoretical and Experimental Case for a Visual Deficit in Specific Reading Disability," *Cognitive Neuropsychology*, vol. 3, No. 2, Lawrence Erlbaum Associates Limited, pp. 225-267 (1986).

Lovegrove, W.J. et al., "Experimental evidence for a transient system deficit in specific reading disability," *Journal of American Optometrists Association*, vol. 61, No. 2, pp. 137-146 (1990).

Skottun, B.C., "Mini review: The magnocellular deficit theory of dyslexia: the evidence from contrast sensitivity," *Vision Research*, vol. 40, Elsevier Science Ltd., pp. 111-127 (2000).

Wright, B.A. et al., "Nonlinguistic perceptual deficits associated with reading and language disorders," *Current Opinions in Neurobiology*, vol. 10, pp. 482-486 (2000).

O'Brien, B.A. et al., "The effect of contrast on reading speed in dyslexia," *Vision Research*, vol. 40, Elsevier Science Ltd., pp. 1921-1935 (2000).

Merigan, W.H. amd Maunsell, J.H.R., "How Parallel Are the Primate Visual Pathways?" *Annual Reviews in Neuroscience*, vol. 16, Annual Reviews, Inc., pp. 369-402 (1993).

Newsome, W.T. and Paré, E.B., "A Selective Impairment of Motion Perception Following Lesions of the Middle Temporal Visual Area (MT)," *The Journal of Neuroscience*, vol. 8, No. 6, Society for Neuroscience, pp. 2201-2211 (Jun. 1988).

Cornelissen, P. et al., "Contrast Sensitivity and Coherent Motion Detection Measured at Photopic Luminance Levels in Dyslexics and Controls," *Vision Research*, vol. 35, No. 10, Elsevier Science Ltd., pp. 1483-1494 (1995).

Witton, C. et al., "Sensitivity to dynamic auditory and visual stimuli predicts nonword reading ability in both dyslexic and normal readers," *Current Biology*, vol. 8, No. 14, Current Biology Ltd., pp. 791-797 (1998).

Livingstone, M.S. et al., "Physiological and anatomical evidence for a magnocellular defect in developmental dyslexia," *Proceedings of the National Academy of Science USA*, vol. 88, pp. 7943-7947 (Sep. 1991).

Enroth-Cugell, C. and Robson, J.G., "The Contrast Sensitivity of Retinal Ganglion Cells of the Cat," *Journal of Physiology*, vol. 187, pp. 517-552 (1966).

Shapley, R. and Perry, V.H., "Cat and monkey retinal ganglion cells and their visual functional roles," *Trends in Neuroscience*, Elsevier Science Publishers B.V., pp. 229-235 (May 1986).

Bullier, J. and Nowak, L.G., "Parallel versus serial processing: new vistas on the distributed organization of the visual system," *Current Opinion in Neurobiology*, vol. 5, Current Biology Ltd., pp. 497-503 (1995).

Ungerleider, L.G. and Mishkin, M., "Two Cortical Visual Systems," *Analysis of Visual Behaviour*, pp. 549-586 (1982).

Milner, A.D. and Goodale, M.A., *The Visual Brain in Action*, Oxford University Press, Inc., ISBN 0 19 852136 7, copy of entire book submitted, (1995).

Stein, J.F. and Glickstein, M., "Role of the Cerebellum in Visual Guidance of Movement," *Physiological Reviews*, vol. 72, No. 4, The American Physiological Society, pp. 967-1017 (Oct. 1992).

Goldstein, E.B., *Sensation and Perception*, Brooks/Cole Publishing Company, ISBN 0-534-34680-4, copy of entire book submitted (1999).

Logothetis, N.K., "Physiological Studies of Motion Inputs," *Visual Detection of Motion*, Academic Press Ltd., pp. 177-216 (1994).

Baizer, J.S. et al., "Organization of Visual Inputs to the Inferior Temporal and Posterior Parietal Cortex in Macaques," *The Journal of Neuroscience*, vol. 11, No. 1, Society for Neuroscience, pp. 168-190 (Jan. 1991).

Thach, W.T. et al., "The Cerebellum and the Adaptive Coordination of Movement," *Annual Reviews in Neuroscience*, vol. 15, Annual Reviews Inc., pp. 403-443 (1992).

Ackermann, H. and Hertrich, I., "The contribution of the cerebellum to speech processing," *Journal of Neurolinguistics*, vol. 13, Elsevier Science Ltd., pp. 95-116 (2000).

Fulbright, R.K. et al., "The Cerebellum's Role in Reading: A Functional MR Imaging Study," *American Journal of Neuroradiology*, vol. 20, American Society of Neuroradiology, pp. 1925-1930 (Nov./Dec. 1999).

Nicolson, R.I. and Fawcett, A.J., "Automaticity: A new framework for dyslexia research?"*Cognition*, vol. 35, Elsevier Publishers, B.V., pp. 159-182 (1990).

Fawcett, A.J. et al., "Impaired Performance of Children with Dyslexia on a Range of Cerebellar Tasks," *Annals of Dyslexia*, vol. 46, The Orton Dyslexia Society, pp. 259-283 (1996).

Nicolson, R.I. et al., "Time estimation deficits in developmental dyslexia: evidence of cerebellar involvement," *Proceedings of the Royal Society of London B- Biological Sciences*, vol. 259, The Royal Society, pp. 43-47 (1995).

Wolpert, D.M. et al., "An Internal Model for Sensorimotor Integration," *Science*, vol. 269, pp. 1880-1882 (Sep. 29, 1995).

Wolpert, D.M. et al., "Internal models in the cerebellum," *Trends in Cognitive Sciences*, vol. 2, No. 9, Elsevier Science Ltd., pp. 338-347 (Sep. 1998).

Block, R.A. and Zakay, D., "Models of psychological time revisited," *Time and Mind*, Hogrefe and Huber Publishers, pp. 171-193 (1996).

Lundy-Ekman, L. et al., "Timing and Force Control Deficits in Clumsy Children," *Journal of Cognitive Neuroscience*, vol. 3, No. 4, Massachusetts Institute of Technology, pp. 367-376 (1991).

Ackermann, H. et al., "Categorical Speech Perception in Cerebellar Disorders," *Brain and Language*, vol. 60, Academic Press, pp. 323-331 (1997).

Mathiak, K. et al., "Cerebellum and Speech Perception: A Functional Magnetic Resonance Imaging Study," *Journal of Cognitive Neuroscience*, vol. 14, No. 6, Massachusetts Institute of Technology, pp. 902-912 (2002).

Lovegrove, W.J. et al., "Specific Reading Disability: Differences in Contrast Sensitivity as a Function of Spatial Frequency," *Science*, vol. 210, pp. 439-440 (Oct. 24, 1980).

Lennie, P., "Roles of M and P Pathways," *Contrast sensitivity: Proceedings of the Retina Research Foundation Symposia*, vol. 5, The MIT Press, pp. 201-213 (1993).

Steinman, B.A. et al., "Reading with an M Neuron: How a Defective Magnocellular Pathway Interferes with Normal Reading," *Vision and Reading*, GB Putnam's Sons, pp. 209-228 (1994).

Eden, G.F. et al., "Differences in Eye Movements and Reading Problems in Dyslexic and Normal Children," *Vision Research*, vol. 34, No. 10, Elsevier Science Ltd., pp. 1345-1358 (1994).

Slaghuis, W.L. et al., "Visual And Language Processing Disorders Are Concurrent In Dyslexia And Continue Into Adulthood," *Cortex*, vol. 32, Masson S.p.A., pp. 413-438 (1996).

Lovegrove, W., "Do Dyslexics Have A Visual Deficit?" *Facets of Dyslexia and its Remediation*, Elsevier Science Publishers B.V., pp. 33-49 (1993).

Tallal, P., "Auditory Temporal Perception, Phonics, and Reading Disabilities in Children," *Brain and Language*, vol. 9, Academic Press, Inc., pp. 182-198 (1980).

Lovegrove, W.J. and Williams, M.C., "Visual Temporal Processing Deficits in Specific Reading Disability," *Visual Processes in Reading and Reading Disabilities*, Lawrence Erlbaum, pp. 311-329 (1993).

Gibson, E.J., *Principles of Perceptual Learning and Development*, Meredith Corporation, copy of entire book submitted (1969).

Gibson, E.J., "Perceptual Development From the Ecological Approach," *Advances in Developmental Psychology*, vol. 3, Eribaum, pp. 243-285 (1984).

Shepard, R.N., "Ecological Constraints on Internal Representation: Resonant Kinematics of Perceiving, Imagining, Thinking, and Dreaming," *Psychological Review*, vol. 91, No. 4, The American Psychological Association, pp. 417-447 (Oct. 1984).

Koenderink, J.J., "Optic Flow," *Vision Research*, vol. 26, No. 1, Pergamon Press Ltd., pp. 161-179 (1986).

Wallach, H. and O'Connell, D.N., "The Kinetic Depth Effect," *Journal of Experimental Psychology*, vol. 45, No. 4, pp. 205-217 (Apr. 1953).

Raymond, J.E., "Attentional modulation of visual motion perception," *Trends in Cognitive Sciences*, vol. 4, No. 2, Elsevier Science Ltd., pp. 42-50 (Feb. 2000).

Culham, J.C. et al., "Cortical fMRI Activation Produced by Attentive Tracking of Moving Targets," *Journal of Neurophysiology*, vol. 80, The American Physiological Society, p. 2657-2670 (1998).

Treue, S. and Maunsell, J.H.R., "Effects of Attention on the Processing of Motion in Macaque Middle Temporal and Medial Superior Temporal Visual Cortical Areas," *The Journal of Neuroscience*, vol. 19, No. 17, Society for Neuroscience, pp. 7591-7602 (Sep. 1, 1999).

Treue, S. and Trujillo, J.C.M., "Feature-based attention influences motion processing gain in macaque visual cortex," *Nature*, vol. 399, pp. 575-579 (Jun. 10, 1999).

Bisley, J.W. and Pasternak, T., "The Multiple Roles of Visual Cortical Areas MT/MST in Remembering the Direction of Visual Motion," *Cerebral Cortex*, vol. 10, Oxford University Press, pp. 1053-1065 (Nov. 2000).

Bisley, J.W. et al., "Microstimulation of Cortical Area MT Affects Performance on a Visual Working Memory Task," *Journal of Neurophysiology*, vol. 85, The American Physiological Society, pp. 187-196 (2001).

Chun, M.M. and Jiang, Y., "Top-Down Attentional Guidance Based on Implicit Learning of Visual Covariation," *Psychological Science*, vol. 10, No. 4, American Psychological Society, pp. 360-365 (1999).

O'Keefe, J. and Nadel, L., *The Hippocampus as a Cognitive Map*, Oxford University Press, ISBN 0-19-857206-9, copy of entire book submitted (1978).

Muller, R.U. et al., "On the Directional Firing Properties of Hippocampal Place Cells," *The Journal of Neuroscience*, vol. 14, No. 12, Society for Neuroscience, pp. 7235-7251 (Dec. 1994).

Taube, J.S. et al., "Head-Direction Cells Recorded from the Postsubiculum in Freely Moving Rats. I. Description and Quantitative Analysis," *The Journal of Neuroscience*, vol. 10, No. 2, Society for Neuroscience, pp. 420-435 (Feb. 1990).

Taube, J.S., "Head Direction Cells Recorded in the Anterior Thalamic Nuclei of Freely Moving Rats," *The Journal of Neuroscience*, vol. 15, No. 1, Society for Neuroscience, pp. 70-86 (Jan. 1995).

Ivry, R.B. et al., "Dissociation of the lateral and medial cerebellum in movement timing and movement execution," *Experimental Brain Research*, vol. 73, Springer-Verlag, pp. 167-180 (1988).

Decety, J. et al., "The cerebellum participates in mental activity: topographic measurements of regional cerebral blood flow," *Brain Research*, vol. 535, Elsevier Science Publishers B.V. (Biomedical Division), pp. 313-317 (1990).

Ryding, E. et al., "Motor imagery activates the cerebellum regionally. A SPECT rCBF study with $^{99m}$Tc-HMPAO," *Cognitive Brain Research*, vol. 1, Elsevier Science Publishers B.V., pp. 94-99 (1993).

Jueptner, M. et al., "Localization of a cerebellar timing process using PET," *Neurology*, vol. 45, pp. 1540-1545 (1995).

Penhune, V.B. et al., "Cerebellar Contributions to Motor Timing: A PET Study of Auditory and Visual Rhythym Reproduction," *Journal of Cognitive Neuroscience*, vol. 10, No. 6, The Massachusetts Institute of Technology, pp. 752-765 (1998).

Andersen, R.A. et al., "Coordinate transformations in the representation of spatial information," *Current Opinion in Neurobiology*, vol. 3, Current Biology Ltd., pp. 171-176 (1993).

Andersen, R.A., "Coordinate Transformations and Motor Planning in Posterior Parietal Cortex," *The Cognitive Neurosciences*, The MIT Press, pp. 519-532 (1995).

Guariglia, C. et al., "Unilateral neglect restricted to visual imagery," *Nature*, vol. 364, pp. 235-237 (Jul. 15, 1993).

Snowden, R.J. et al., "The Response of Area MT and V1 Neurons to Transparent Motion," *The Journal of Neuroscience*, vol. 11, No. 9, Society for Neuroscience, pp. 2768-2785 (Sep. 1991).

Qian, N. et al., "Transparent Motion Perception as Detection of Unbalanced Motion Signals. I. Psychophysics," *The Journal of Neuroscience*, vol. 14, No. 12, Society for Neuroscience, pp. 7357-7366 (Dec. 1994).

Saito, H. et al., "Integration of Direction Signals of Image Motion in the Superior Temporal Sulcus of the Macaque Monkey," *The Journal of Neuroscience*, vol. 6, No. 1, Society for Neuroscience, pp. 145-157 (Jan. 1986).

Duffy, C.J. and Wurtz, R.H., "Sensitivity of MST Neurons to Optic Flow Stimuli. II. Mechanisms of Response Selectivity Revealed by Small-Field Stimuli," *Journal of Neurophysiology*, vol. 65, No. 6, pp. 1346-1359 (Jun. 1991).

Graziano, M.S.A. et al., "Tuning of MST Neurons to Spiral Motions," *The Journal of Neuroscience*, vol. 14, No. 1, Society for Neuroscience, pp. 54-67 (Jan. 1994).

Gibson, J.J. *The Perception of the Visual World*, The Riverside Press, copy of entire book submitted (1950).

Horn, B.K.P. and Schunck, B.G., "Determining Optical Flow," *Artificial Intelligence*, vol. 17, North-Holland, pp. 185-203 (1981).

Bradley, D.C. et al., "Mechanisms of Heading Perception in Primate Visual Cortex," *Science*, vol. 273, pp. 1544-1547 (Sep. 13, 1996).

Lee, D.N., "A theory of visual control of braking based on information about time-to-collision," *Perception*, vol. 5, pp. 437-459 (1976).

Royden, C.S. et al., "Estimating Heading During Eye Movements," *Vision Research*, vol. 34, No. 23, Elsevier Science Ltd., pp. 3197-3214 (1994).

Freeman, T.C.A. and Banks, M.S., "Rapid Communication: Perceived Head-centric Speed is Affected by Both Extra-retinal and Retinal Errors," *Vision Research*, vol. 38, No. 7, Elsevier Science Ltd., pp. 941-945 (1998).

Krapp, H.G. and Hengstenberg, R., "Estimation of self-motion by optic flow processing in single visual interneurons," *Nature*, vol. 384, pp. 463-466 (Dec. 5, 1996).

Cornilleau-Pérès, V. and Gielen, C.C.A.M., "Interactions between self-motion and depth perception in the processing of optic flow," *Trends in Neuroscience*, vol. 19, No. 5, Elsevier Science Ltd., pp. 196-202 (1996).

Rogers, B. and Graham, M., "Similarities Between Motion Parallax and Stereopsis in Human Depth Perception," *Vision Research*, vol. 22, Pergamon Press Ltd., pp. 261-270 (1982).

Tresilian, J.R., "Correcting some misperception of time-to-collision: a critical note," *Perception*, vol. 26, pp. 229-236 (1997).

Wang, Y., and Frost, B.J., "Time to collision is signaled by neurons in the nucleus rotundus of pigeons," *Nature*, vol. 356, pp. 236-238 (Mar. 19, 1992).

Albright, T.D. et al., "Columnar Organization of Directionally Selective Cells in Visual Area MT of the Macaque," *Journal of Neurophsyiology*, vol. 51, No. 1, pp. 16-31 (Jan. 1984).

Tanaka, K. et al., "Analysis of Local and Wide-Field Movements in the Superior Temporal Visual Areas of the Macaque Monkey," *The Journal of Neuroscience*, vol. 6, No. 1, Society for Neuroscience, pp. 134-144 (Jan. 1986).

Siegel, R.M. and Read, H.L., "Analysis of Optic Flow in the Monkey Parietal Area 7a," *Cerebral Cortex*, vol. 7, pp. 327-346 (Jun. 1997).

Regan, D. and Beverley, K.I., "Visually Guided Locomotion: Psychophysical Evidence for a Neural Mechanism Sensitive to Flow Patterns," *Science*, vol. 205, pp. 311-313 (Jul. 20, 1979).

Morrone, M.C. et al., "Two stages of visual processing for radial and circular motion," *Nature*, vol. 376, pp. 507-509 (Aug. 10, 1995).

Aslin, R. et al., "Computation of Conditional Probability Statistics By 8-Month-Old Infants," *Psychological Science*, vol. 9, No. 4, American Psychological Society, pp. 321-324 (Jul. 4, 1998).

Zeki, S.M., "Functional Organization of a Visual Area in the Posterior Bank of the Superior Temporal Sulcus of the Rhesus Monkey," *Journal of Physiology*, vol. 236, Cambridge University Press, pp. 549-573 (1974).

Zeki, S.M., "Functional specialization in the visual cortex of the rhesus monkey," *Nature*, vol. 274, Macmillan Journals Ltd., pp. 423-428 (Aug. 3, 1978).

Zeki, S., "Colour Coding in the Cerebral Cortex: The Reaction of Cells in Monkey Visual Cortex to Wavelengths and Colours," *Neuroscience*, vol. 9, No. 4, Pergamon Press Ltd., pp. 741-765 (1983).

Zeki, S., "Colour Coding in the Cerebral Cortex: The Responses of Wavelength-Selective and Colour-Coded Cells in Monkey Visual Cortex to Changes in Wavelength Composition," *Neuroscience*, vol. 9, No. 4, Pergamon Press Ltd., pp. 767-781 (1983).

Glickstein, M. and May, J.G., "Visual Control of Movement: The Circuits Which Link Visual to Motor Areas of the Brain with Special Reference to the Visual Input to the Pons and Cerebellum," *Contributions to Sensory Physiology*, vol. 7, Academic Press, Inc., pp. 103-145 (1982).

Cavada, C. and Goldman-Rakic, P.S., "Posterior Parietal Cortex in Rhesus Monkey: II. Evidence for Segregated Corticocortical Networks Linking Sensory and Limbic Areas With the Frontal Lobe," *The Journal of Comparative Neurology*, vol. 287, Alan R. Liss, Inc., pp. 422-445 (1989).

Boussaoud, D. et al., "Frontal lobe mechanisms subserving vision-for-action versus vision-for-perception," *Behavioural Brain Research*, vol. 72, Elsevier Science B.V., pp. 1-15 (1996).

Wise, S.P. et al., "Premotor and Parietal Cortex: Corticocortical Connectivity and Combinatorial Computations," *Annual Reviews in Neuroscience*, vol. 20, pp. 25-42 (1997).

Kling, A.S. and Brothers, L.A., "The Amygdala and Social Behaviour," *The Amygdala: Neurobiological Aspects of Emotion, Memory, and Mental Dysfunction*, Wiley-Liss, Inc., pp. 353-377 (1992).

Brothers, L. and Ring, B., "Mesial temporal neurons in the macaque monkey with responses selective for aspects for social stimuli," *Behavioural Brain Research*, vol. 57, Elsevier Science Publishers B.V., pp. 53-61 (1993).

Eden, G.F. et al., "Abnormal processing of visual motion in dyslexia revealed by functional brain imaging," *Nature*, vol. 382, pp. 66-69 (Jul. 4, 1996).

Carrasco, M. and McElree, B., "Covert attention accelerates the rate of visual information processing," *Proceedings of the National Academy of Sciences*, vol. 98, No. 9, pp. 5363-5367 (Apr. 24, 2001).

Bridgeman, B. et al., "Segregation of cognitive and motor aspects of visual function using induced motion," *Perception & Psychophysics*, vol. 29, No. 4, Psychonomic Society, pp. 336-342 (1981).

Howe, M.L. and Pasnak, R. (eds.), *Emerging Themes in Cognitive Development vol. I: Foundations*, Springer-Verlag, ISBN 0-387-97816-X, copy of entire book submitted (1993).

Diamond, A., "Developmental Time Course in Human Infants and Infant Monkeys, and the Neural Bases of, Inhibitory Control in Reaching," *Annals of the New York Academy of Sciences*, vol. 608, pp. 637-676 (1990).

Diamond, A. et al., "AB With Multiple Wells: 1. Why Are Multiple Wells Sometimes Easier Than Two Wells? 2. Memory or Memory + Inhibition?" *Developmental Psychology*, vol. 30. No. 2, The American Psychological Association, pp. 192-205 (1994).

Ridderinkhof, K.R. and van der Molen, W., "A Psychophysiological Analysis of Development Differences in the Ability to Resist Interference," *Child Development*, vol. 66, The Society for Research in Child Development, Inc., pp. 1040-1056 (1995).

Burack, J.A. and Enns, J.T. (Eds.), *Attention, Development, and Psychopathology*, The Guilford Press, ISBN 1-57230-198-8, copy of entire book submitted (1997).

Bjorklund, D.F. and Harnishfeger, K.K., "The Resources Construct in Cognitive Development: Diverse Sources of Evidence and a Theory of Inefficient Inhibition," *Developmental Review*, vol. 10, Academic Press, Inc., pp. 48-71 (1990).

Sokolov, Y.N., *Perception and the Conditioned Reflex*, Pergamon Press Ltd., Library of Congress Card No. 62-22210, copy of entire book submitted (1963).

Graham, F.K. and Clifton, R.K., "Heart-Rate Change as a Component of the Orienting Response," *Psychological Bulletin*, vol. 65, No. 5, pp. 305-320 (1966).

Lacey, J.I. et al., "The Visceral Level: Situational Determinants and Behavioral Correlates of Autonomic Response Patterns," *Expression of Emotions in Man*, International Universities of Press, pp. 161-196 (1960).

Weissler, A.M. et al., "Bedside Technics for the Evaluation of Ventricular Function in Man," *The American Journal of Cardiology*, vol. 23, pp. 577-583 (Apr. 1969).

Weissler, A.M. et al., "Systolic Time Intervals in Heart Failure in Man," *Circulation*, vol. XXXVII, No. 2, The American Heart Association, pp. 149-159 (Feb. 1968).

Turvey, M.T. et al., "Ecological laws of perceiving and acting: In reply to Fodor and Pylyshyn (1981)," *Cognition*, vol. 9, Elsevier Sequoia S.A., pp. 237-304 (1981).

Regan, D., "Orientation Discrimination For Objects Defined By Relative Motion And Objects Defined By Relative Motion And Objects Defined By Luminance Contrast," *Vision Research*, vol. 29, No. 10, Pergamon Press plc, pp. 1389-1400 (1989).

Stein, J. and Walsh, V., "To see but not to read: the magnocellular theory of dyslexia," *Trends in Neurosciences*, vol. 20, No. 4 (226), Elsevier Science Ltd., pp. 147-152 (Apr. 1997).

Wurtz, R.H. et al., "Brain Mechanisms of Visual Attention," *Scientific American*, vol. 246, No. 6, Scientific American, Inc., pp. 124-135 (Jun. 1982).

English-language Abstract for Japanese Patent Publication No. 02-031768, from http://www19.ipdl.jpo.go.jp, 2 pages (Date of publication of application—Feb. 1, 1990).

English-language Abstract for Japanese Patent Publication No. 11-164894, from http://www19.ipdl.jpo.go.jp, 2 pages (Date of publication of application—Jun. 22, 1999).

English-language Abstract for Japanese Patent Publication No. 2001-170089, from http://www19.ipdl.jpo.go.jp, 1 page (Date of publication of application—Jun. 26, 2001).

English-language Abstract for PCT Publication No. WO 00/11397, from Dialog File 349:PCT Fulltext, 2 pages (Date of publication of application—Mar. 2, 2000).

Berkeley, B., "An Essay Towards A New Theory of Vision," in Rhys, E. (ed.), *Everyman's Library: Theology and Philosophy*, No. 483, pp. vii-xxiv and 1-86 (1910).

Duffy, C.J. and Wurtz, R.H., "Sensitivity of MST Neurons to Optic Flow Stimuli. I. A Continuum of Response Selectivity to Large-Field Stimuli," *Journal of Neurophysiology*, vol. 65, No. 6, The American Physiological Society, pp. 1329-1345 (Jun. 1991).

International Search Report for Application No. PCT/IB 03/03671, mailed Dec. 17, 2003.

Diamond, A., "Close Interrelation of Motor Development and Cognitive Development and of the Cerebellum and Prefrontal Cortex," *Child Development* 71:1, pp. 44-56 (Jan./Feb. 2000).

| Library 1102 |
|---|
| Orientation — 1402 |
| Length — 1404 |
| Width — 1406 |
| Size — 1408 |
| Curvature — 1410 |
| Number — 1412 |
| Terminators — 1414 |
| Intersections — 1416 |
| Enclosure — 1418 |
| Color (hue) — 1420 |
| Intensity — 1422 |
| Flicker — 1424 |
| Direction of Motion — 1426 |
| Binocular lustre — 1428 |
| Stereoscopic depth — 1430 |
| 3-D depth cues — 1432 |
| Lightening direction — 1434 |
| Shape — 1436 |
| Collinearity — 1438 |
| Spatial Grouping — 1440 |
| Added Marks — 1442 |

FIG. 14

| Library 1104 |
|---|
| Promote stimuli detection in the peripheral visual field — 1502 |
| Select a perceptual motor activity for the subject to periodically engage his/her focus attention towards the central region of the displayed visual field where the optical events are taking place in game/entertainment program module 908 — 1504 |
| Use black-white visual field angular sectors alternance (frequency = angular degrees per each white-black alternance period) — 1506 |
| Introduce transient stimuli characterized by a temporal variability of brief durations in stimuli parameters and/or in the time interval between stimuli changes — 1508 |

FIG. 15

| Library 1106 |
|---|
| Time duration — 1602 |
| Graphic display (e.g., form, width, length, size, etc.) — 1604 |
| Color — 1606 |
| Intensity — 1608 |
| Number of changes in an optical event in time duration, graphic display, color and/or intensity — 1610 |
| Magnitude of changes in the number of changes in an optical event — 1612 |
| Sequential order of changes at the number of changes in an optical event and/or in the magnitude of changes in the number of changes in an optical event — 1614 |

FIG. 16

Main Subcycles of the Heart Cycle

|  | Temporal Variability Conditions or Values assigned to options (selected from a pull of options) |
|---|---|
| VC 2501 | Three options for the possible occurrence of an OE Photic Stimuli during: mechanical systole; mechanical systole and mechanical diastole; mechanical diastole |
| VC 2502 | One or more consecutive ground state OE, includes: (a) will be followed by photic change in one or more consecutive OE; and/or (b) Four options are provided for different a/b ratios S1, S2, S3, S4, which are assigned to four different sets of consecutive heart cycles $N_1$, $N_2$, $N_3$, $N_4$, respectively |
| VC 2503 | Two wave amplitude forms options (A&B) for 3 consecutive photic changes during an OE taking place in mechanical diastole |
| VC 2504 | Four options for the total duration of three successive photic OE changes in mechanical diastole |
| VC 2505 | Four options for the duration of an OE in mechanical systole |
| VC 2506 | Four options in time delays for OE in mechanical systole (In relation to a fiducial point in the ECG) |
| VC 2507 | Eight options in time delays for OE in diastole (In relation to a fiducial point in the ECG) |
| VC 2508 | Seven color options for each one of the three successive sub-intervals of OE changes in mechanical diastole |
| VC 2512 | To choose among 4 possible time periods during which icons will keep emerging from screen options zones previously selected at VC 2511 |
| VC 2513 | To choose among 4 possible options for the total time, given in number of heart cycle, an icon is allowed to move across the screen, since its emergence point in the screen zone till reaches the opposite side of the screen. |
| VC 2514 | To choose among 3 possible options for changing the velocity vectors of each icon, from the moment the icon emerges in the screen zone till the icon disappears on the other side of the screen altogether |

FIG. 26

|  | Spatial Variability Conditions or Values assigned to options (selected from a pull of options) |
|---|---|
| VC 2509 | Two different lengths for the OE icon form (given as a fraction of the screen's width) |
| VC 2510 | Choose among " N" options for the perceptual graphic form of the OE icon (refers to "terminators") |
| VC 2511 | The perceptual emergence of an icon in the screen is selected among four possible (screen) zones, for example, top left – bottom right – top right – bottom left. |
| VC 2515 | To choose among 4 possible screen sub-zones within each possible screen zone in VC11, from which an icon could perceptually emerge |
| VC 2516 | To choose among 8 possible perceptual emerging points in the screen that an icon could emerge within the already chosen sub-zone at VC 2515. |
| VC 2517 | To choose among 8 possible points on the opposite and respective sub-zone in the screen an icon could arrive. |
| VC 2518 | To choose among 4 possible changes in icon thickness (defined in number of pixels). Thickness changes takes place when the icon changes from its (default) ground state (1 pixel) to an active photic state (each time that the OE is changed during diastole). |

FIG. 27

APPARATUS, METHOD AND COMPUTER PROGRAM PRODUCT TO FACILITATE ORDINARY VISUAL PERCEPTION VIA AN EARLY PERCEPTUAL-MOTOR EXTRACTION OF RELATIONAL INFORMATION FROM A LIGHT STIMULI ARRAY TO TRIGGER AN OVERALL VISUAL-SENSORY MOTOR INTEGRATION IN A SUBJECT

BACKGROUND OF THE INVENTION

1. Field of the Invention

The present invention relates generally to addressing the need to facilitate and/or improve the potential for reciprocal interactions between visual perception and ballistic biomotoric performance in some human movements. More specifically, from the many possible embodiments of the invention, the usefulness of some of these embodiments is for the treatment of many human conditions concerning human vision, including learning disabilities in general and dyslexia in particular.

2. Related Art

Perception is a process that bridges between reality and knowledge. An enigmatic bridge is embedded in biological-activity, yet it is personally experienced in conscious awareness. In the development of the individual, perception is pivotal. Directly experiencing the physical world and learning social world and language, all people rely on the products of perception. In general, to the extent that perceptual ability is lacking in the beginning of life, these tasks (particularly sensory motor activity and some literacy skills) must be postponed or never accomplished by a person. Hence, its seems of critical importance to gain a clear understanding about perception concerning a rigorous analysis of the task of perception—what is to be perceived—and the ways in which environments make information available to accomplish that task.

Learning disabilities, in general, and dyslexia, in particular, are potential logical targets for a poor or mal-realization of visual perceptual-motor processes in early life. "Developmental Dyslexia" is an example of being a high profile candidate where early visual perceptual-motor deficits have disrupted functional capacities in the individual at the biological, perceptual and cognitive levels, respectively.

SUMMARY OF THE INVENTION

The present invention relates to an apparatus, method and computer program product to facilitate ordinary visual perception via an early perceptual extraction of relational information from a stimuli array to trigger an overall visual-sensory motor integration in a subject. The central tenet of our invention and key to ameliorating deficits that threaten learning disabilities in general and developmental dyslexia in particular, have to do with the method and apparatus of the present invention. The present invention has the ability to reinforce the tied reciprocal relationship between visual perception, and the potential for triggering imminent ballistic bio motoric activity in some human movements due to several reasons. These reasons include (but are not limited to): (1) producing and generating a visual intrinsic dynamical environment that comprises a simple optical flow field (e.g. translational motion), which effortlessly facilitates the direct attainment of early visual perception by displaying visual indicia, and which enables in the perceiver a pre-attentive and automatic pickup of information from the visual stimuli array (via the magnocellular retinocortical and retino-subcortical input principally to the visual dorsal stream but also to the ventral stream); (2) actualizing the potential for triggering imminent ballistic movements of distinct physically distributed body parts in the organism by reinforcing the reciprocal interactions between early visual perceptual processes and imminent bio-motoric activity occurring in reachable space of the subject; and (3) promoting in the subject an overall perceptual-motor integration to attain a dynamical balance among visual perceptual-motor processes in the subject.

Visual ordinary perception encompasses a dynamical equilibrium by finely regulating an existing variable ratio between motor quasi-stationary states (that various body parts assume at times) and motor imminent ballistic movements states (that body parts assume at other times) in the organism. A normal development of visual ordinary perception grants the subject the implicit and automatic capacity to guide and correct his or her own motor behavior at all levels of performance, that is, from implicitly triggering imminent ballistic movements in reachable egocentric space, to attaining fine motor coordination, and to being capable of deploying attention mechanism which cause the eyes to fixate on a particular visual scene (in allocentric space) and allow for the information processing of targets.

This invention is directed towards facilitating direct and implicit extractions of spatial-temporal information from kinematical attributes conveyed in a stimuli array(s). Likewise, this invention is directed towards actively fusing together imminent ballistic action and early perception in the subject's reachable space to facilitate normal early perceptual development of an egocentric space in which the perceiver effortlessly and implicitly and directly extracts information from the ambient as to effectively guide his/her own imminent motor behavior in reachable space.

The general scope and aspect of the teachings of this invention are consistent with many findings in a number of inter-correlated fields, as previously discussed and will be discussed further below. One objective of this invention is to provide the means and method to trigger motor fluency in reading in dyslexic subjects by facilitating the direct extraction of information from a stimuli array via visual early sensory perception.

Another feature of the invention (based on the above information) aims to influence reactivity of the magnocellular system. Triggering magnocellular neuronal firing at specific time intervals will impact the overall plasticity of the magnocellular system, such that it could be possible to retrain its neural networks as to facilitate the perceiver's direct pick up of information from transient stimuli. In other words, the invention aims to develop an enhanced early perceptual acuity to transient stimuli at specific time intervals in the perceiver, such that automatically and effortlessly will orient as to deploy its covert attention faculty towards directly extracting information related to timing sensory and motor events. In general, the information being extracted from the stimuli array relates to the timing of visual events, and in particular, to the motion of visual targets (motion detection).

Another aspect of the teachings and features of this invention is to perceptually provide the perceiver a spatial-temporal array of sensorial visual targets that fulfill basic criteria that enable the perceiver to implicitly pick up pre-attentive mechanisms.

Still, another scope of the teachings and features of this invention is to develop new informative, educative and leisure devices (e.g. computer software games, etc.) and visual dynamic environments displays (e.g. computers, television, films, signs, etc.) for facilitating a broad spectrum of required visual ordinary perceptual skills in human every day life, in normal and pathologic population alike.

Moreover, research in many correlated fields, some of them only outlined above, gives us a firm ground for hypothesizing the imminent need for the technological construction and subsequent frequent exposure of a subject to an intrinsic variable visual dynamic environment. In such a particular visual dynamical environment, the subject will possess at hand a higher probability for automatically engaging his or her early visual perceptual processes on kinematical indicia, such that implicitly triggering orienting towards salient stimuli (pre-attentively cuing). Such particular visual dynamical environment will effortlessly facilitate in the subject the implicit extraction of kinematical attributes of spatial-temporal targets. We are most certain that such an especial dynamical visual environment will trigger an enhanced functional synergism between the ventral and dorsal neuro-visual pathways in the organism.

The teachings of this invention indicate that the technological construction of such an intrinsic variable visual dynamic environment will pave the way for the converging of visual ordinary perception into a normal developmental track, such that the subject will meet the social literacy requirements of reading.

BRIEF DESCRIPTION OF THE DRAWINGS/FIGURES

The accompanying drawings, which are incorporated herein and form part of the specification, illustrate embodiments of the present invention and, together with the description, further serve to explain the principles of the invention and to enable a person skilled in the pertinent art to make and use the invention.

Figure 6:
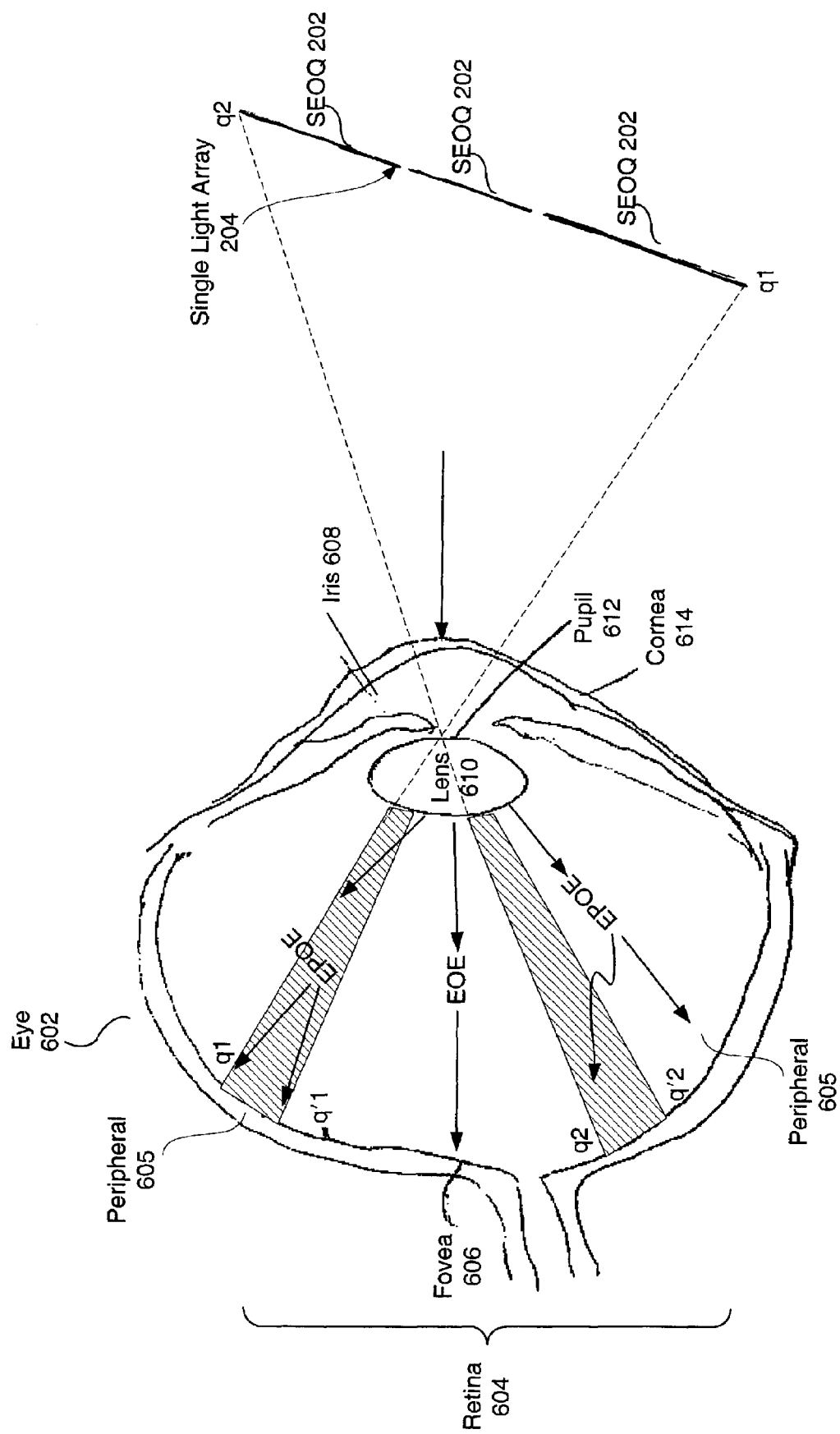

FIG. 6 describes the ocular level according to an embodiment of the present invention.

Figure 7:
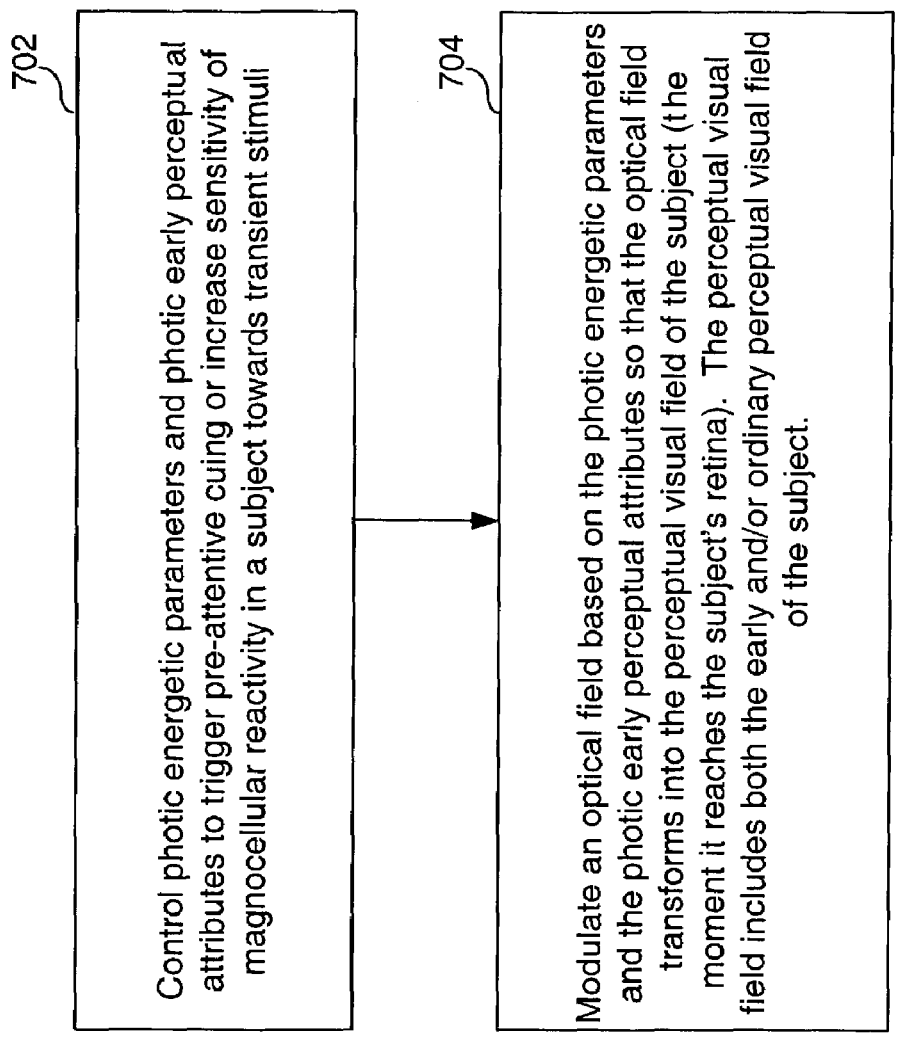

FIG. 7 is a high level flow chart illustrating how the invention shifts the egocentric/allocentric dynamic balance in a subject by controlling early perceptual optical events and energetic optical events in an optical field that is provided to the subject according to an embodiment of the present invention.

Figure 8:
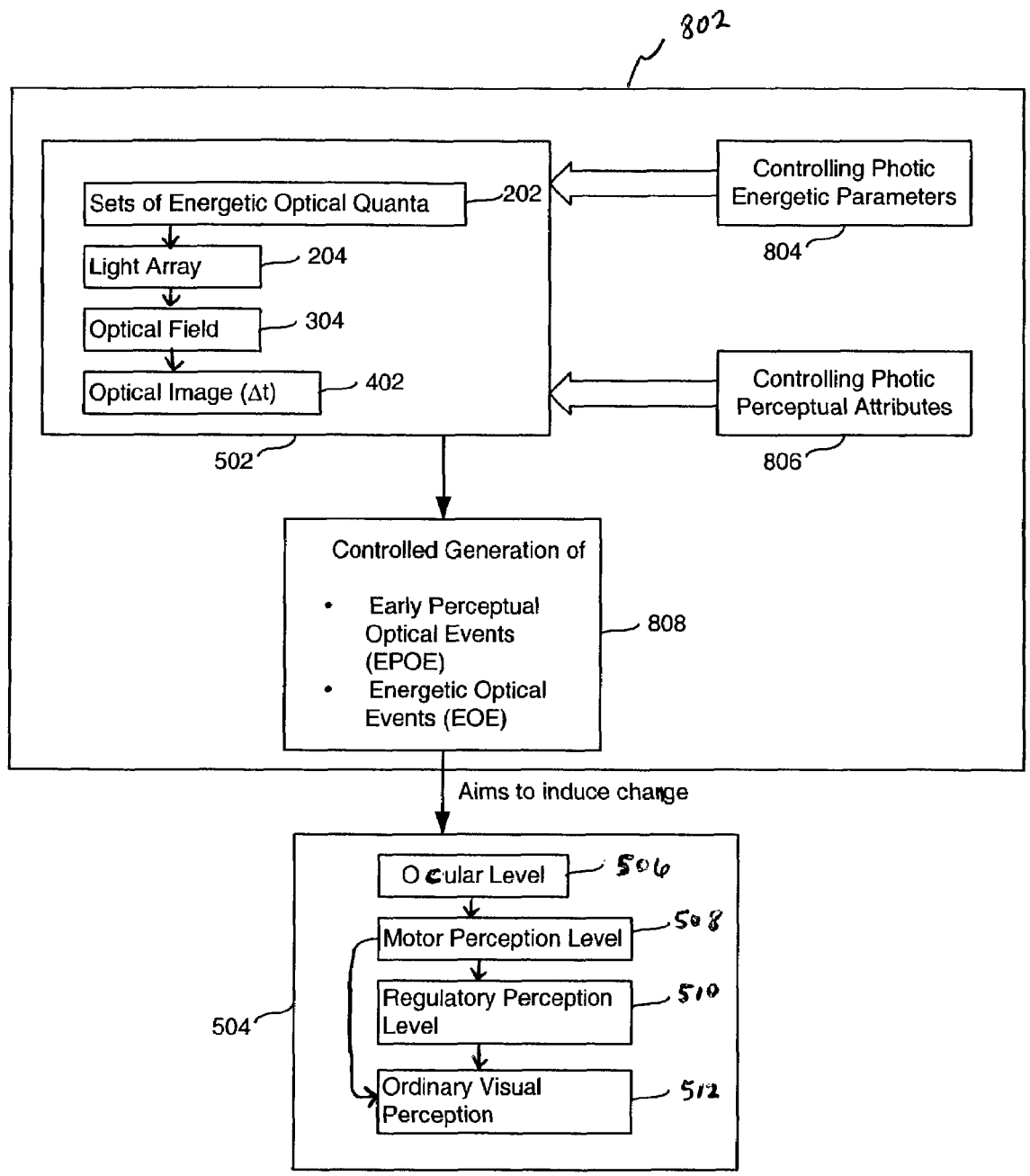

FIG. 8 illustrates how the present invention controls photic energetic parameters and photic early perceptual attributes of the light array to trigger pre-attentive cueing and/or increase sensitivity of magnocellular reactivity in a subject according to an embodiment of the present invention.

Figure 9:
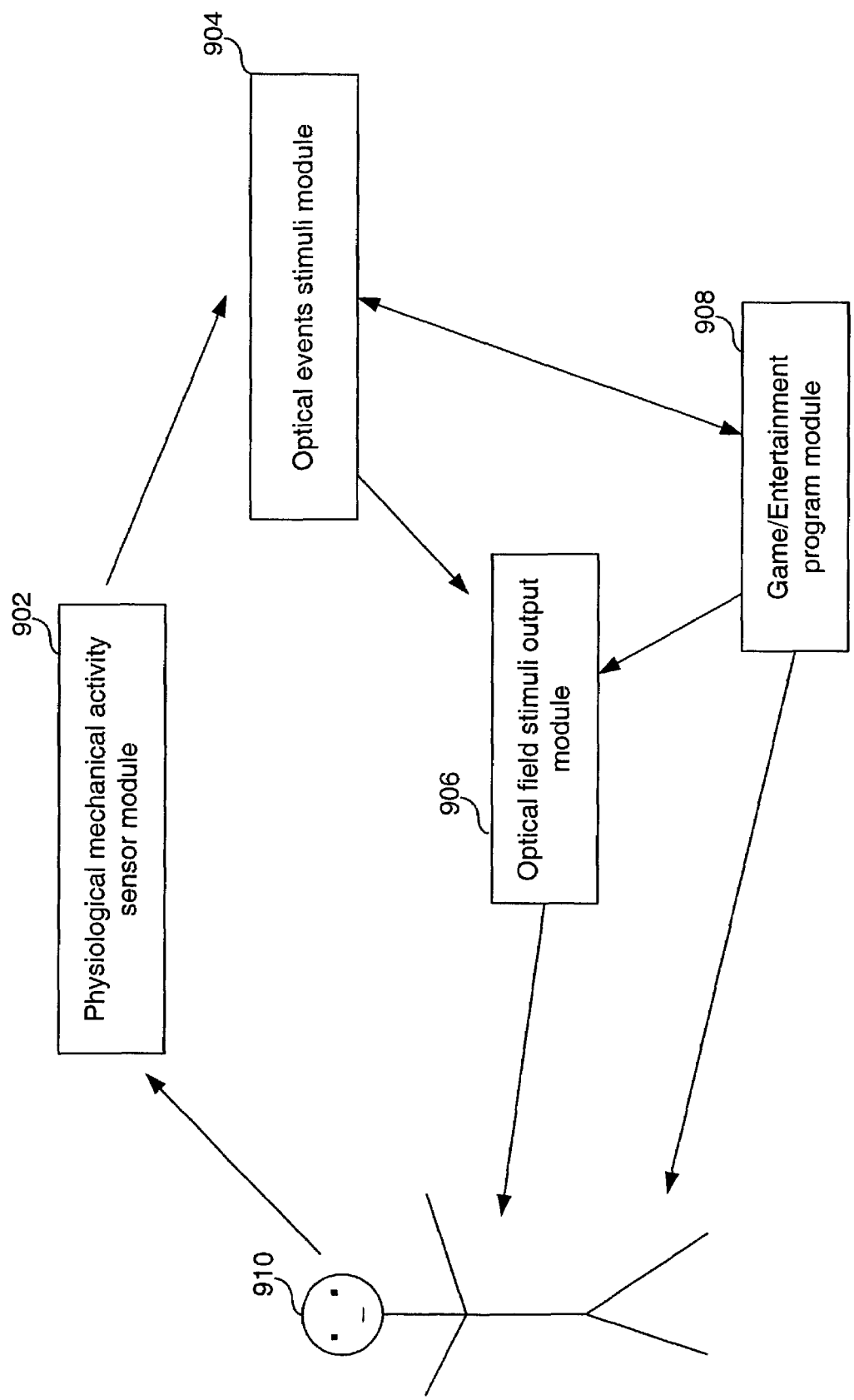

FIG. 9 is a block diagram representing an example system environment of the present invention according to an embodiment.

Figure 10:
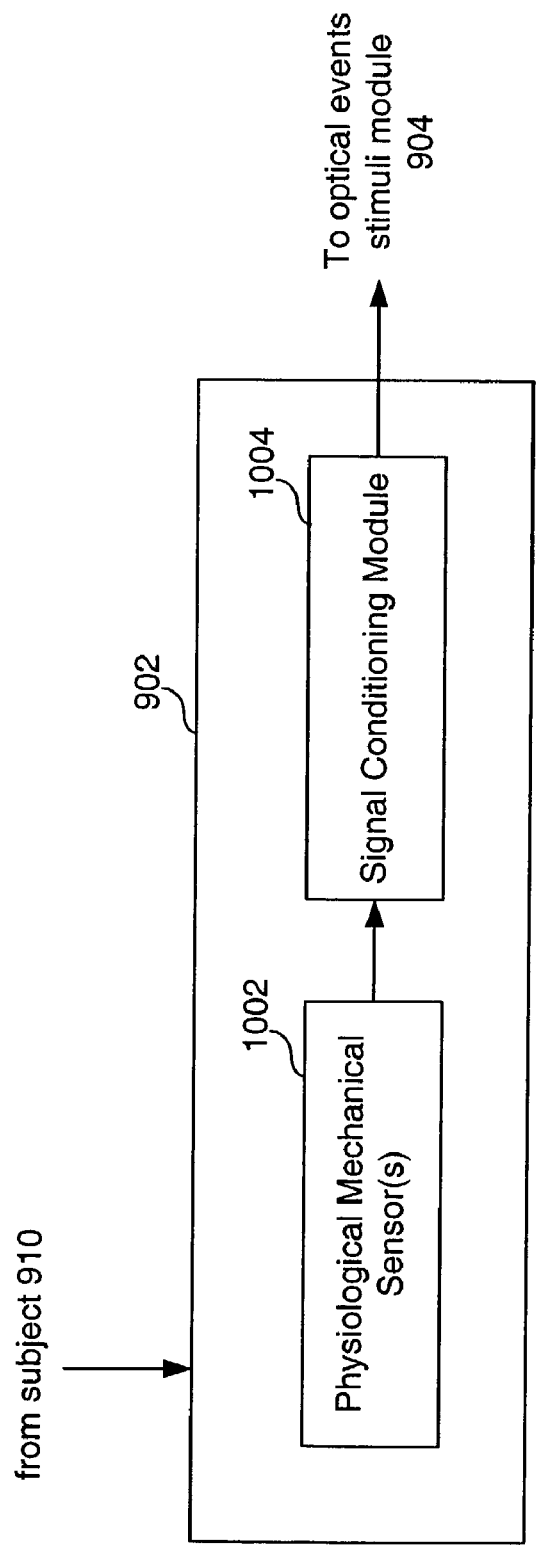

FIG. 10 illustrates that the sensor module is comprised of one or more physiological mechanical sensor(s) and a signal-conditioning module according to an embodiment of the present invention.

Figure 11:
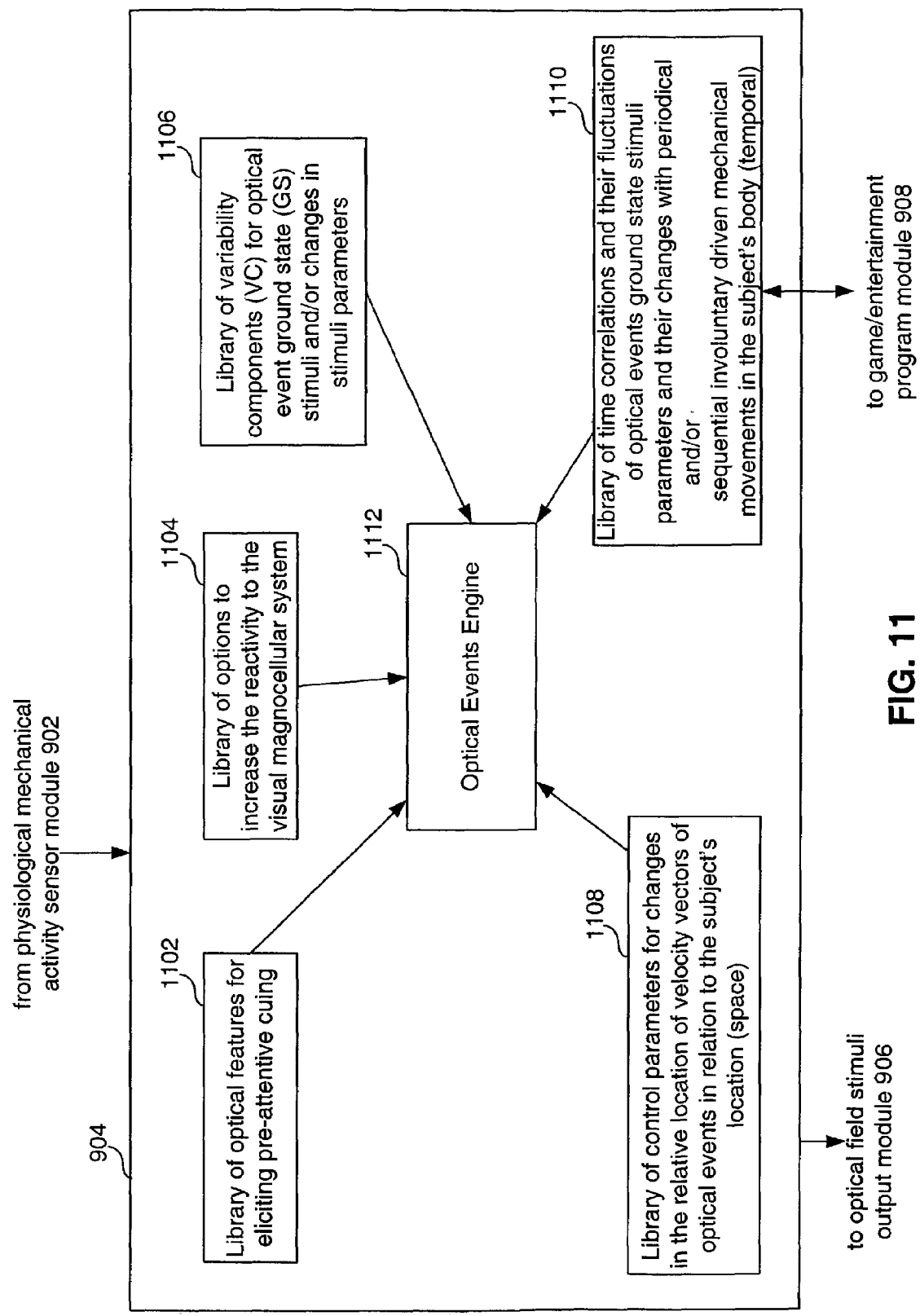

FIG. 11 illustrates the optical events module according to an embodiment of the present invention.

Figure 12:
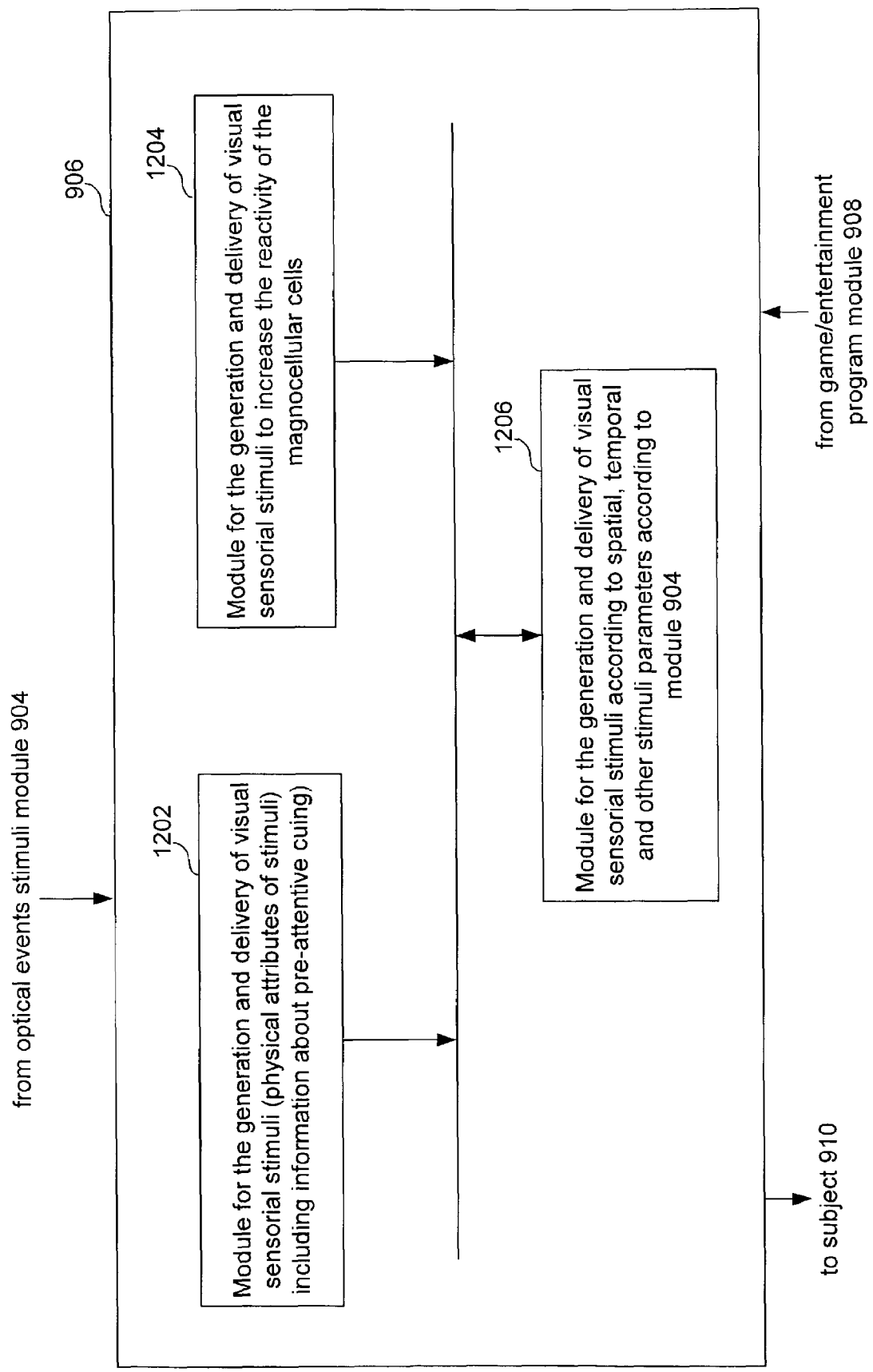

FIG. 12 illustrates that the optical field stimuli output module is comprised of three modules according to an embodiment of the present invention.

Figure 13:
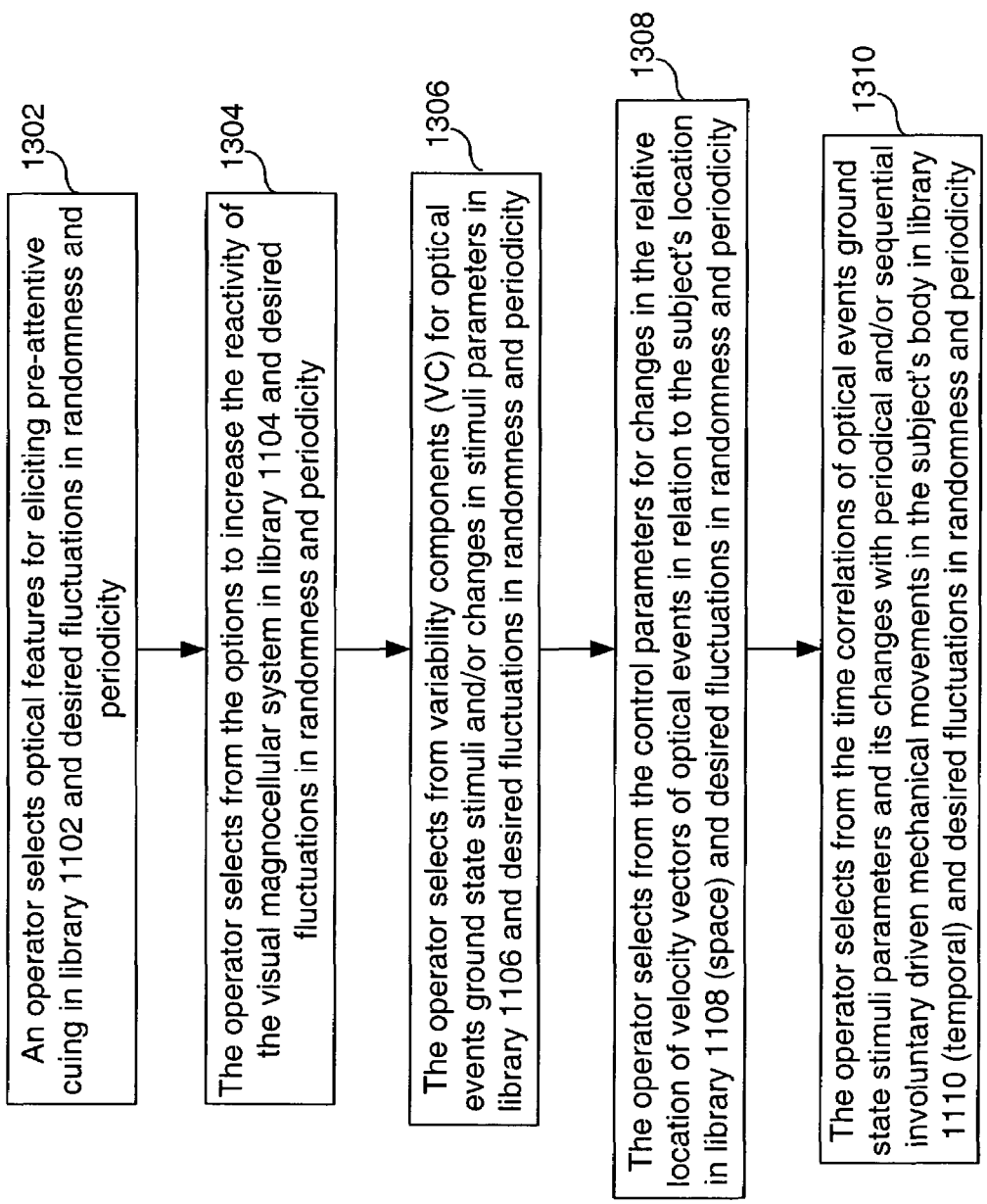

FIG. 13 illustrates the steps to be carried out by an administrator or operator to configure the variability components (VCs) according to an embodiment of the present invention.

FIG. 14 illustrates example optical features for eliciting pre-attentive cuing according to an embodiment of the present invention.

FIG. 15 illustrates example options to increase reactivity of the visual magnocellular system according to an embodiment of the present invention.

FIG. 16 illustrates example options of variability components (VC) for optical event ground state (Gs) stimuli and/or changes in stimuli parameters according to an embodiment of the present invention.

Figure 17:
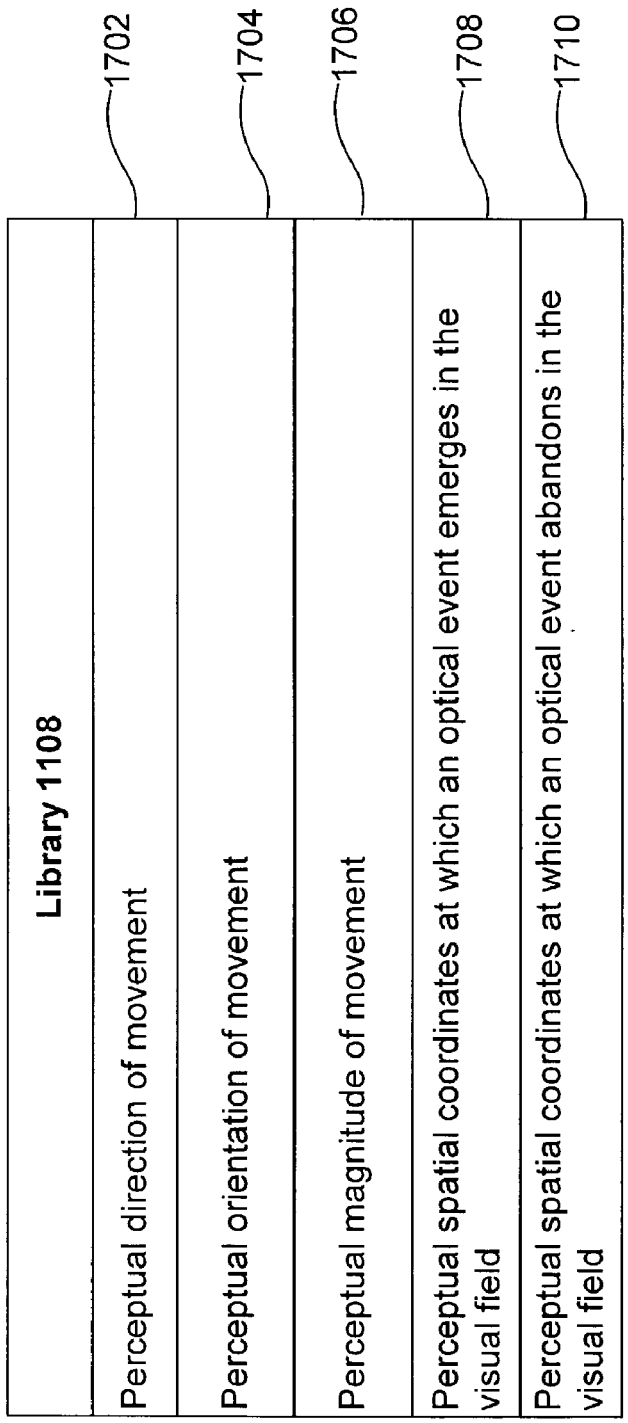

FIG. 17 illustrates example options of control parameters for changes in the relative location of velocity vectors of optical events in relation to the location of the subject according to an embodiment of the present invention.

Figure 18:
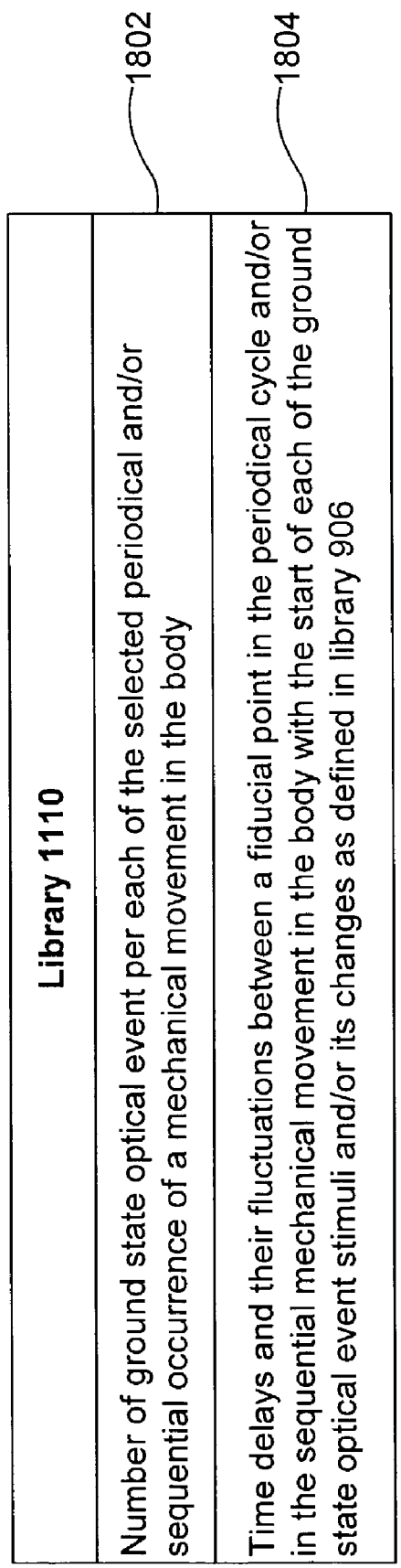

FIG. 18 illustrates example time correlations of optical events ground state stimuli parameters, their fluctuations and their changes with periodical and/or sequential involuntary driven mechanical movements in the body of the subject according to an embodiment of the present invention.

Figure 19:
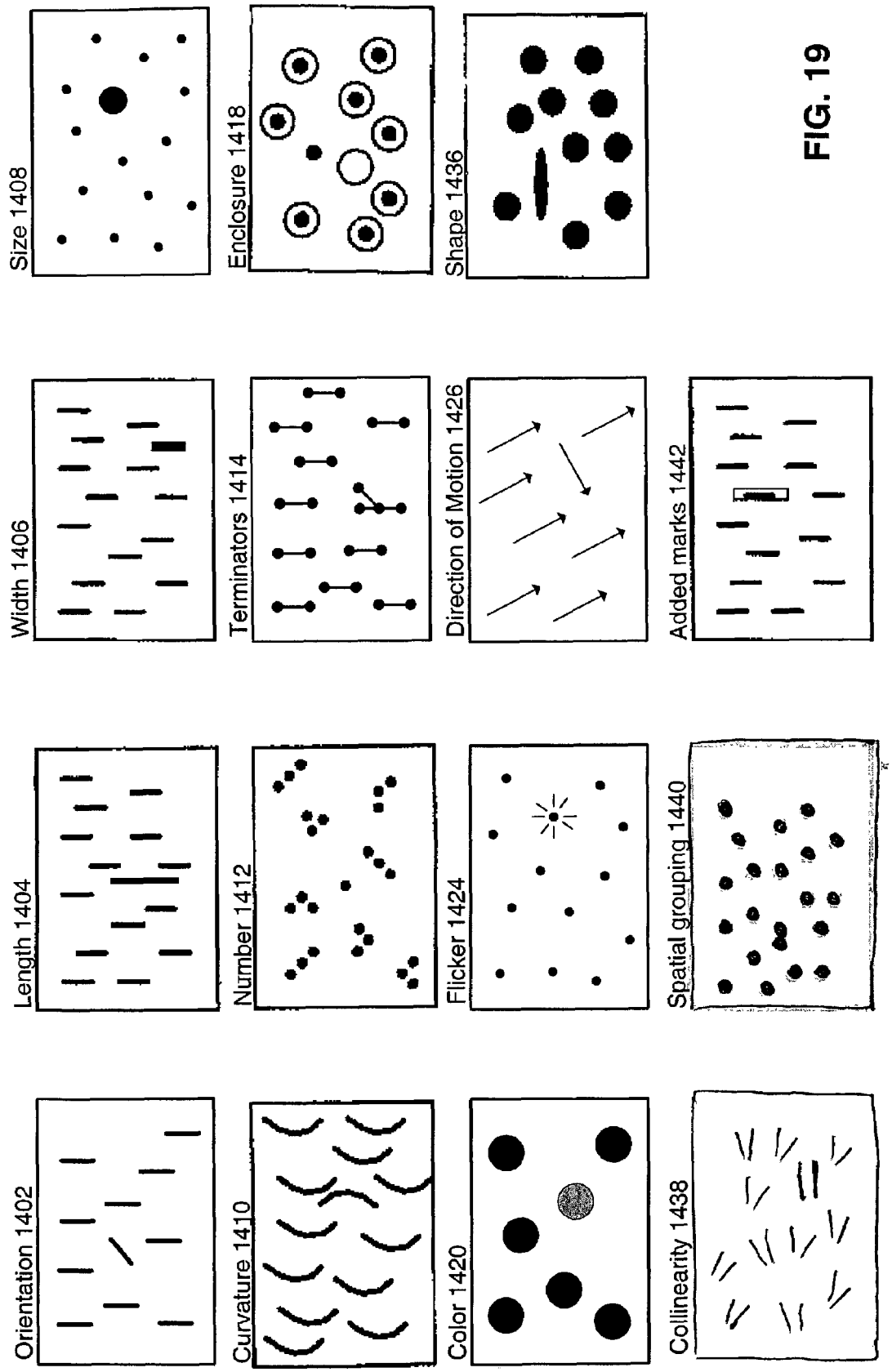

FIG. 19 illustrates various optical features with each feature showing a number of distractors with one target according to an embodiment of the present invention.

Figure 20:
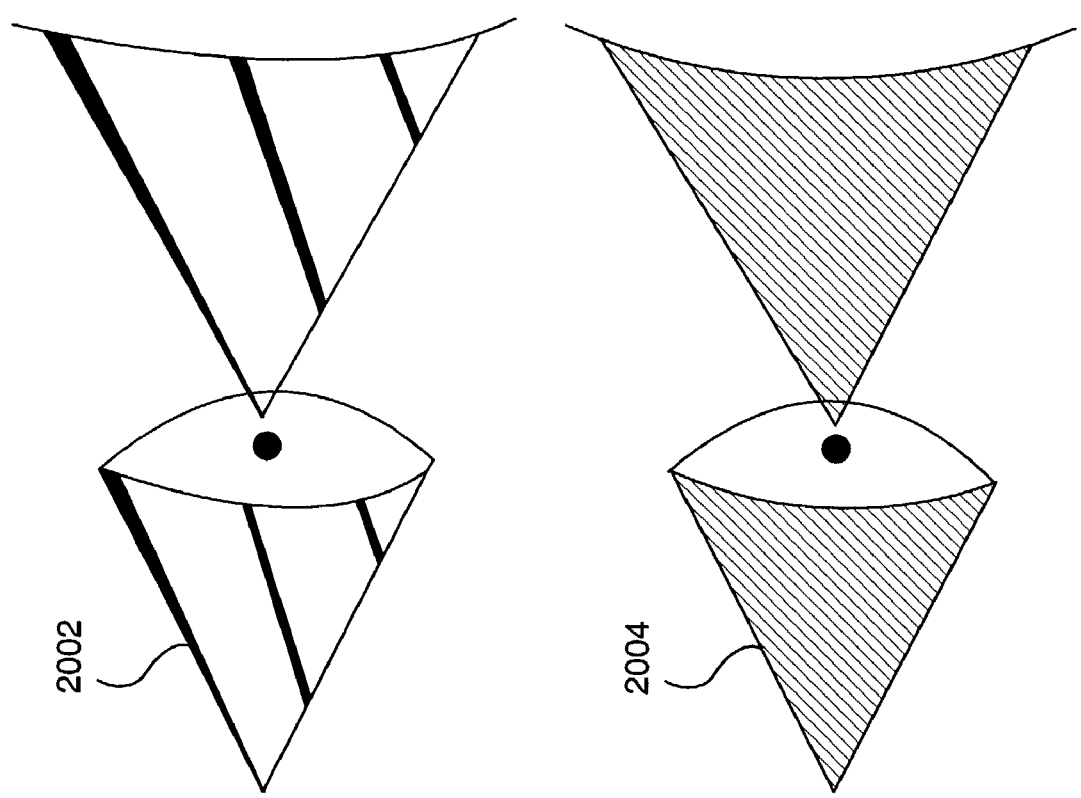

FIG. 20 illustrates frequency of alternance equals angular degrees per each white-black alternance period according to an embodiment of the present invention.

Figure 21:
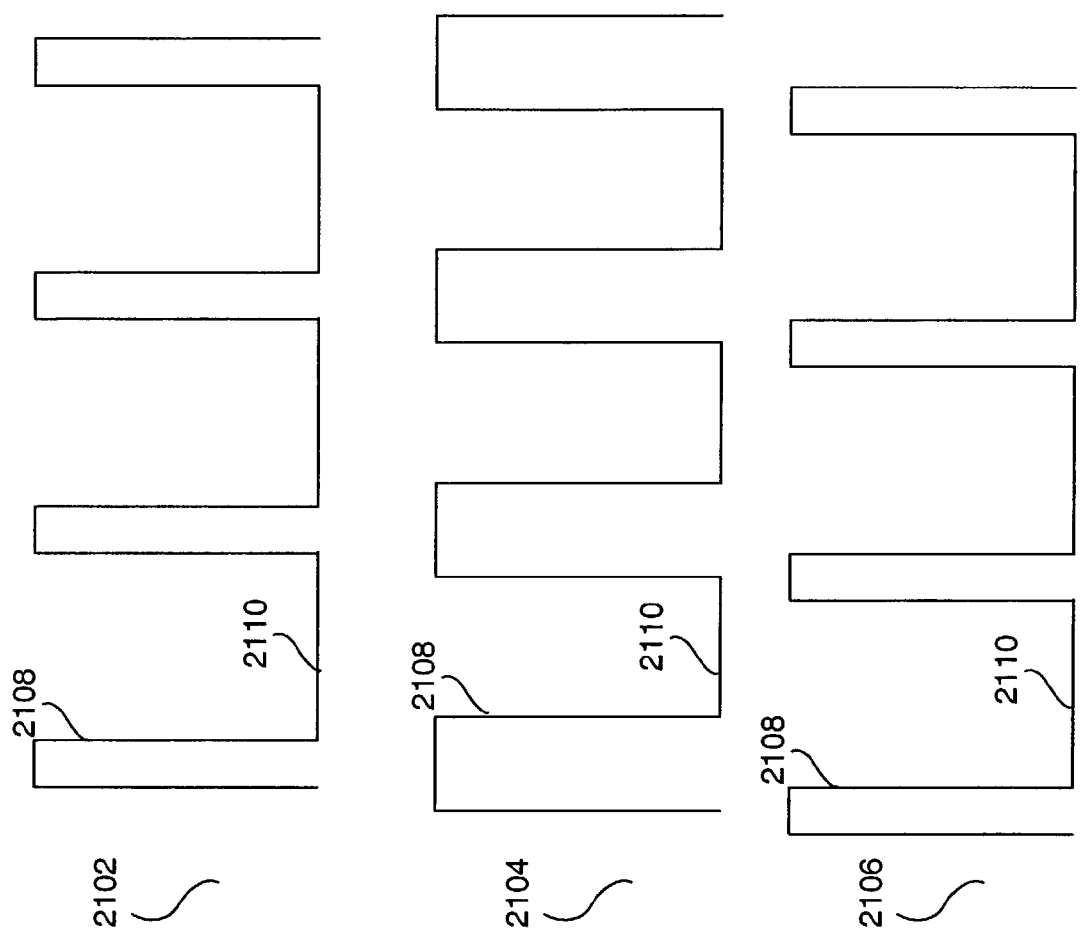

FIG. 21 illustrates transient stimuli that is characterized by a temporal variability of brief durations in stimuli parameters and/or in the time interval between stimuli changes according to an embodiment of the present invention.

Figure 22:
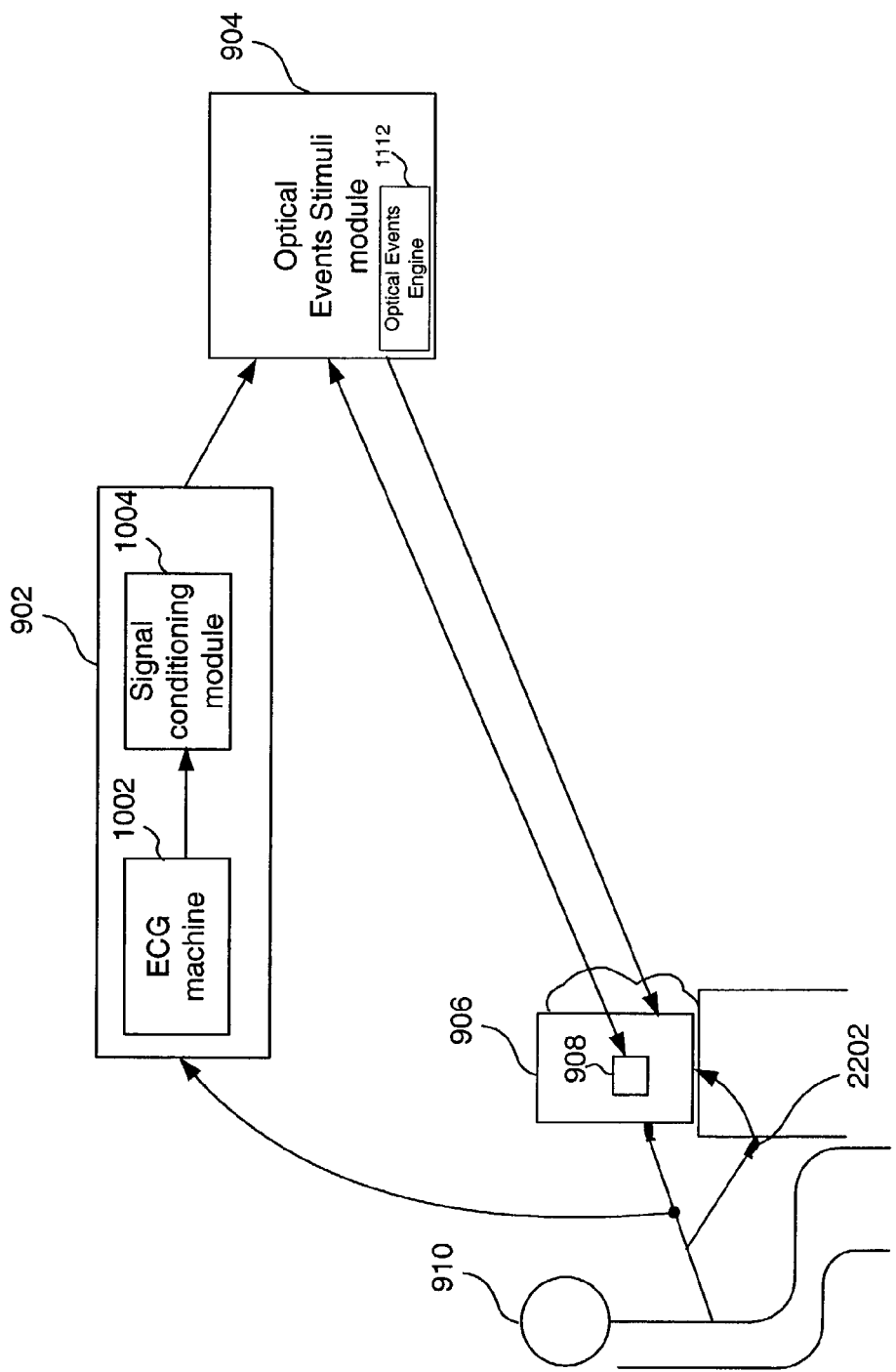

FIG. 22 illustrates one embodiment of the invention that could be used to ameliorate the condition of a dyslexic subject according to an embodiment of the present invention.

Figure 23:
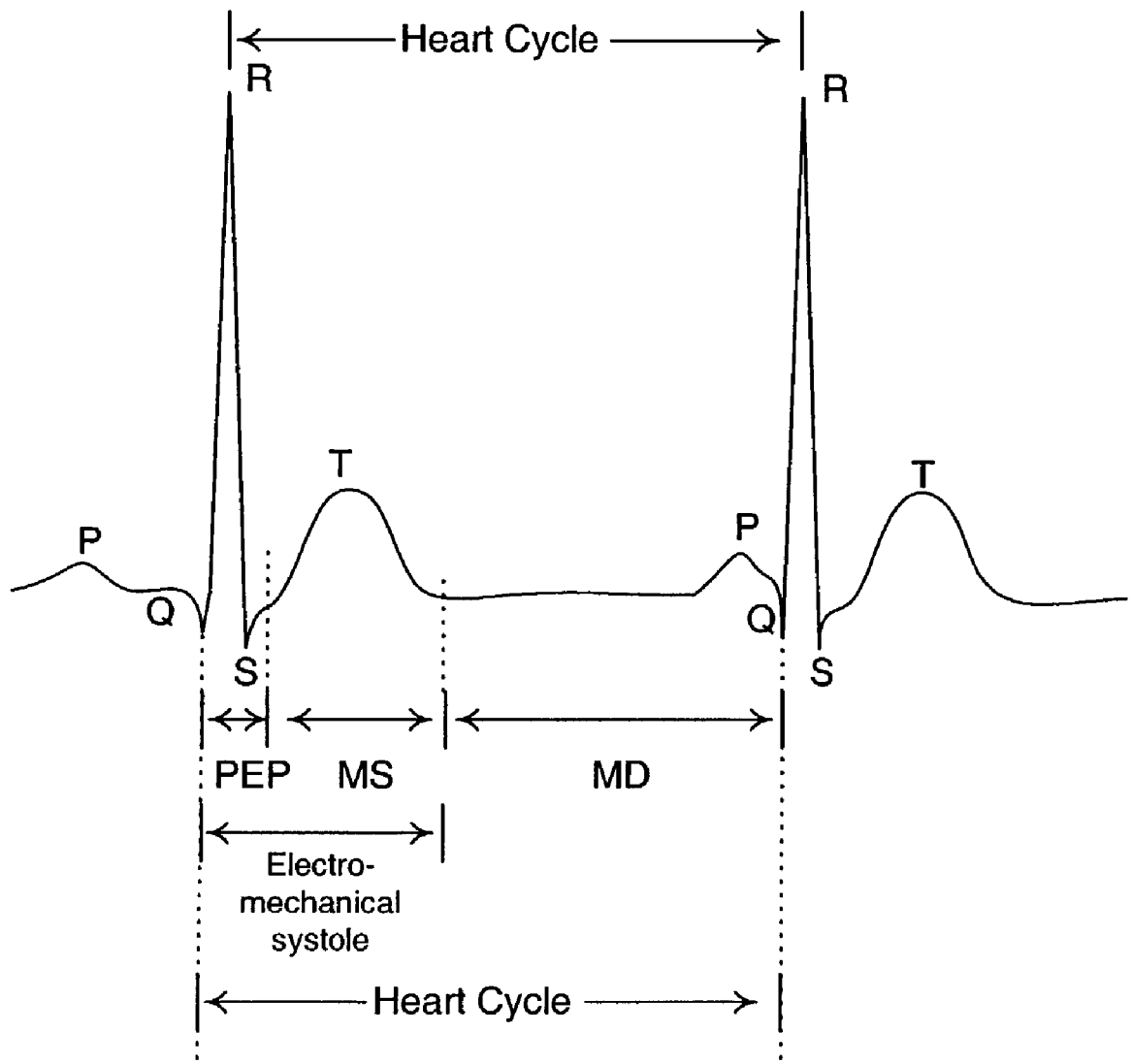

FIG. 23 illustrates the main electrical ECG events characterizing the heart function utilized in an embodiment of the present invention.

Figure 24:
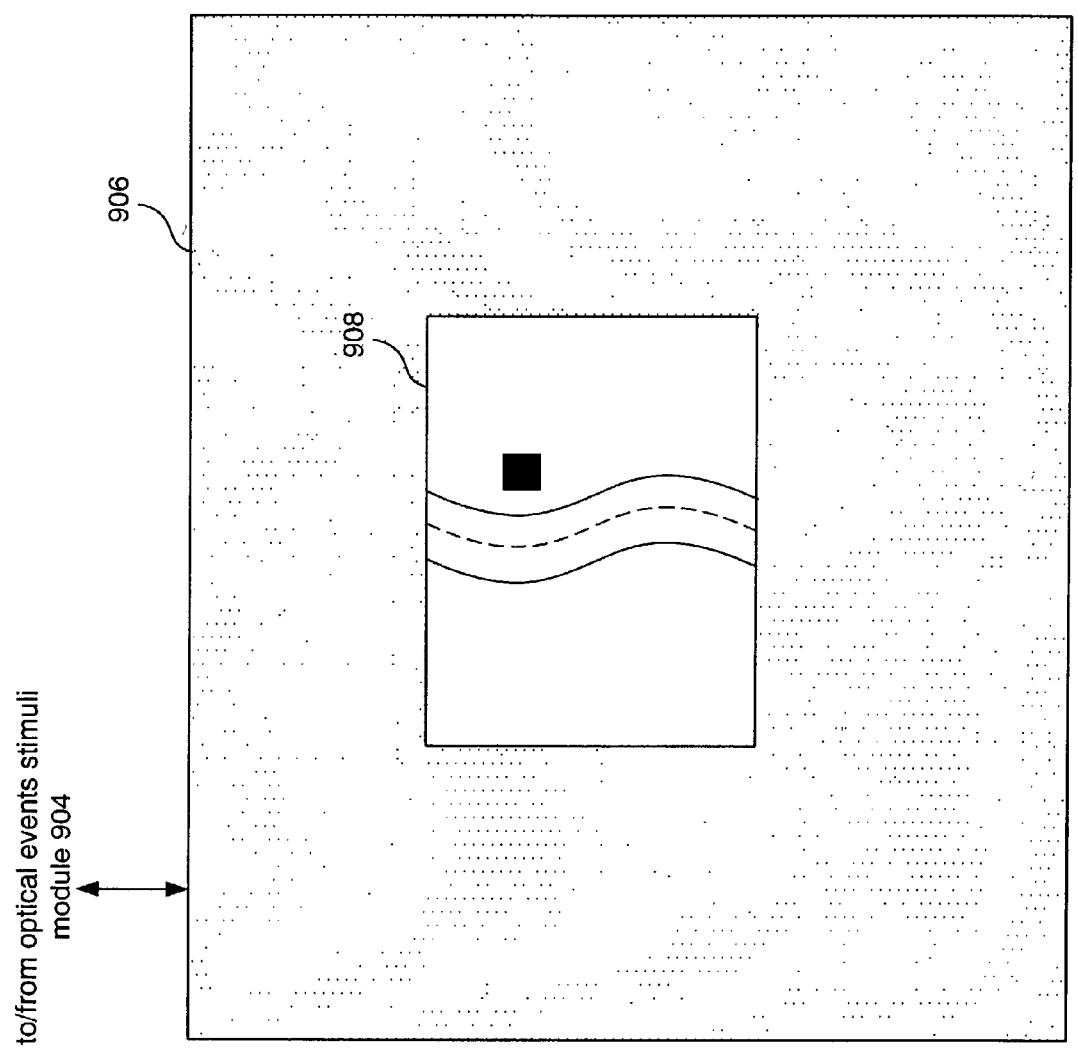

FIG. 24 illustrates an embodiment of the optical field stimuli output module and the game/entertainment program module according to an embodiment of the present invention.

Figure 25:
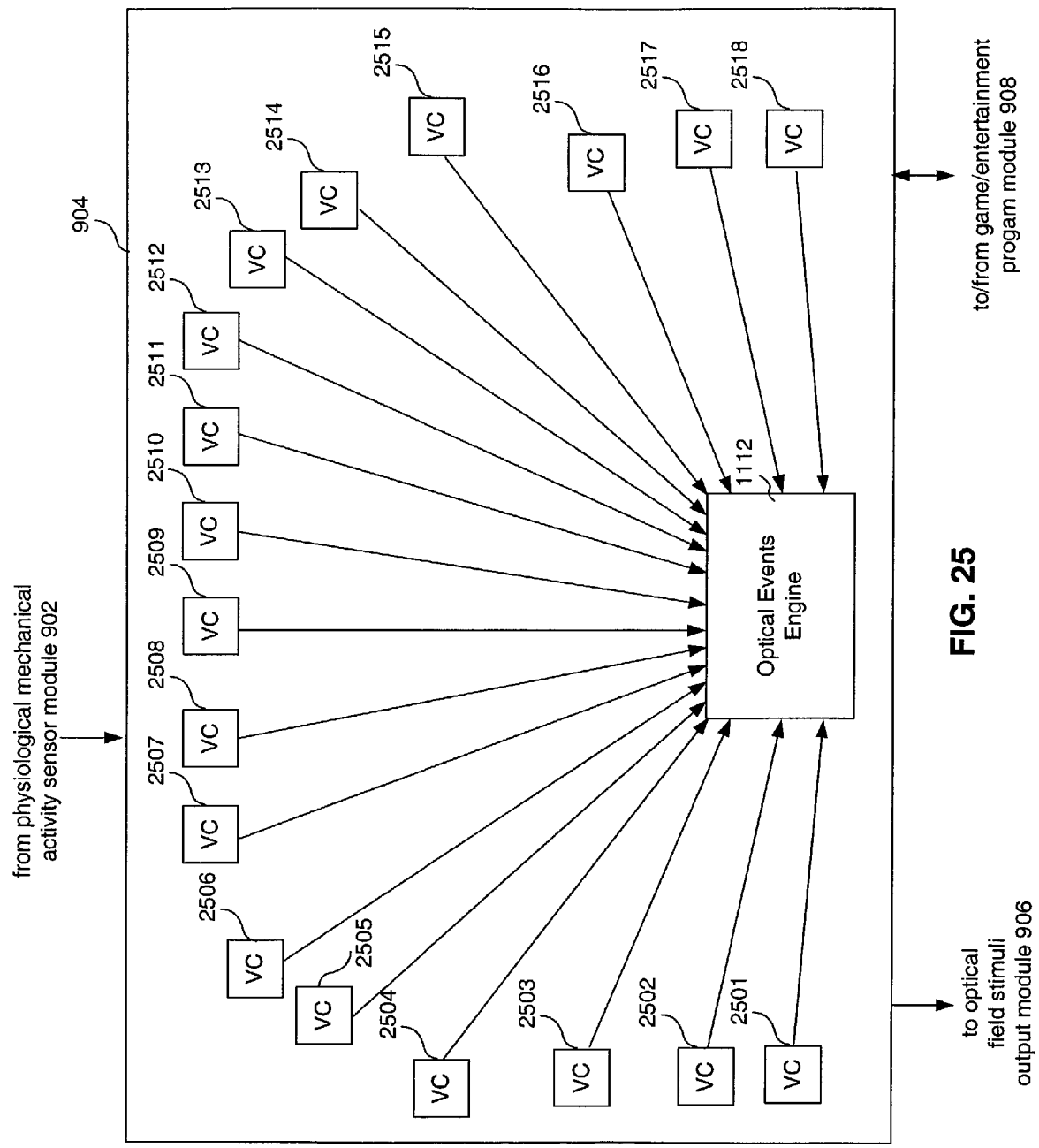

FIG. 25 illustrates example variability components (VC) used in an embodiment of the present invention.

FIG. 26 illustrates temporal variability components (VC) used in an embodiment of the present invention.

FIG. 27 illustrates spatial variability components (VC) used in an embodiment of the present invention.

Figure 28:
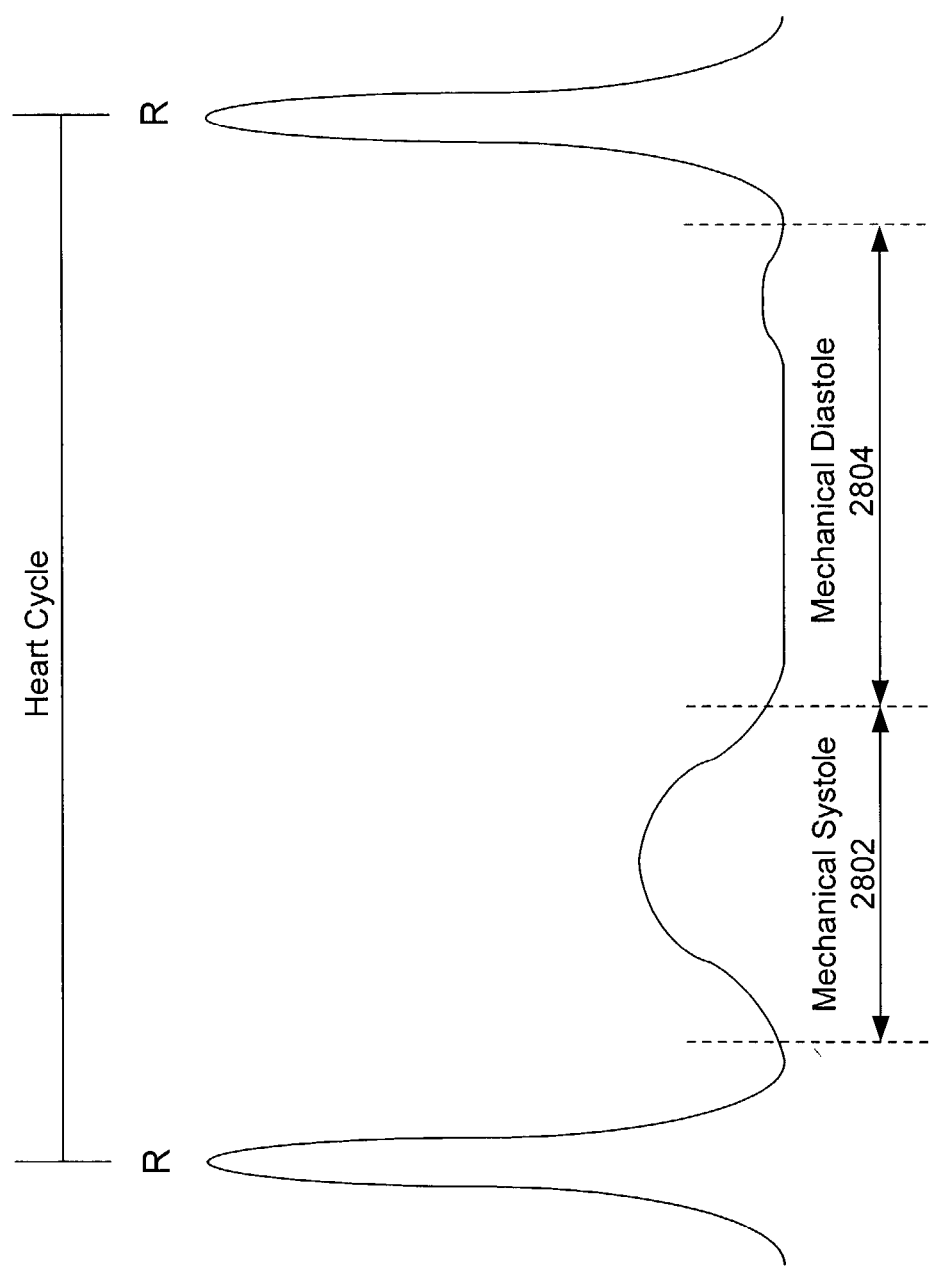

FIG. 28 illustrates the variability component where one ground state icon per cardiac cycle will perceptually enter the visual optical field of the subject according to an embodiment of the present invention.

Figure 29:
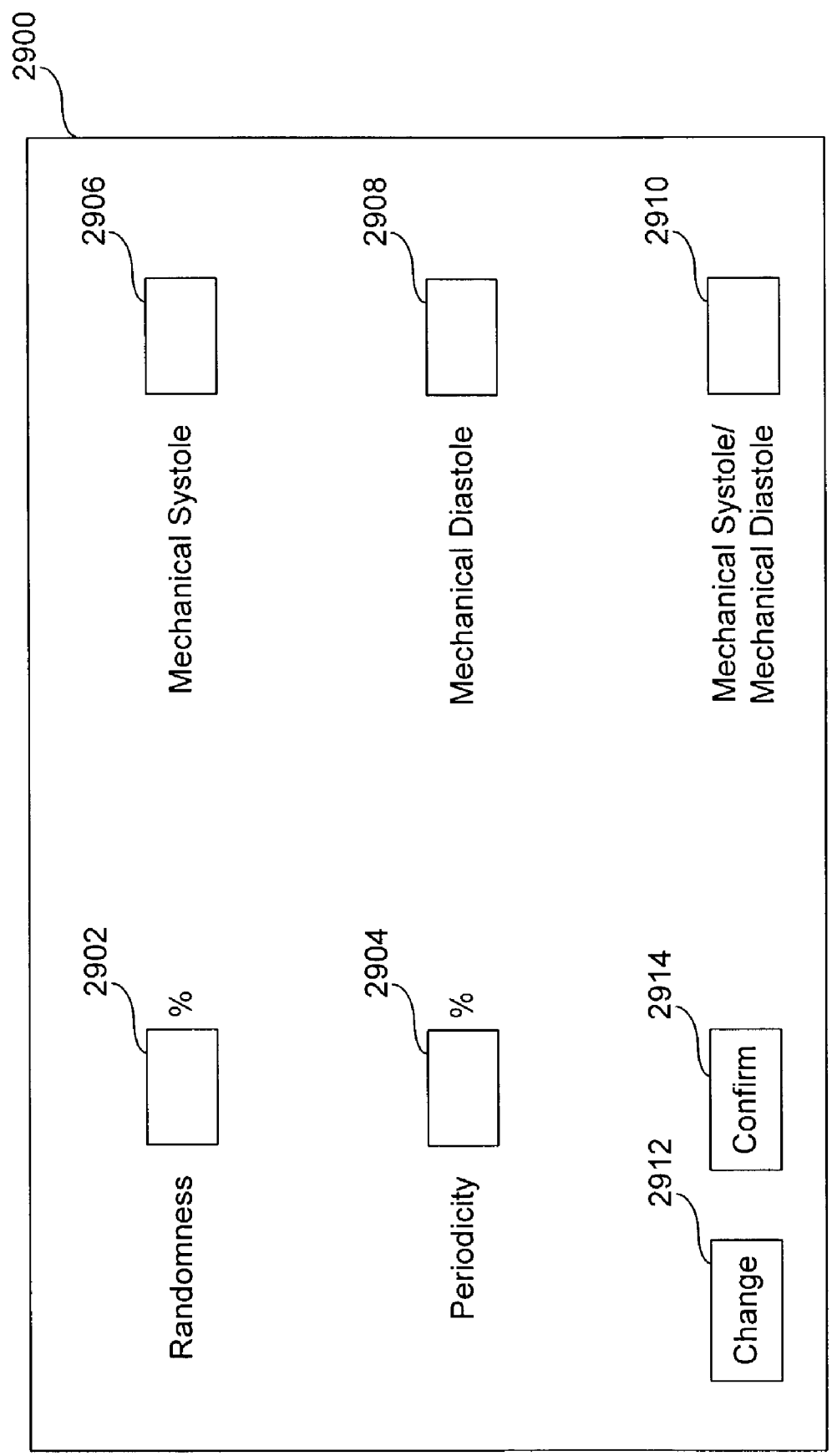

FIG. 29 illustrates an example user interface provided to the administrator of the invention to adjust the randomness and periodicity of the variability components according to an embodiment of the present invention.

Figure 30:
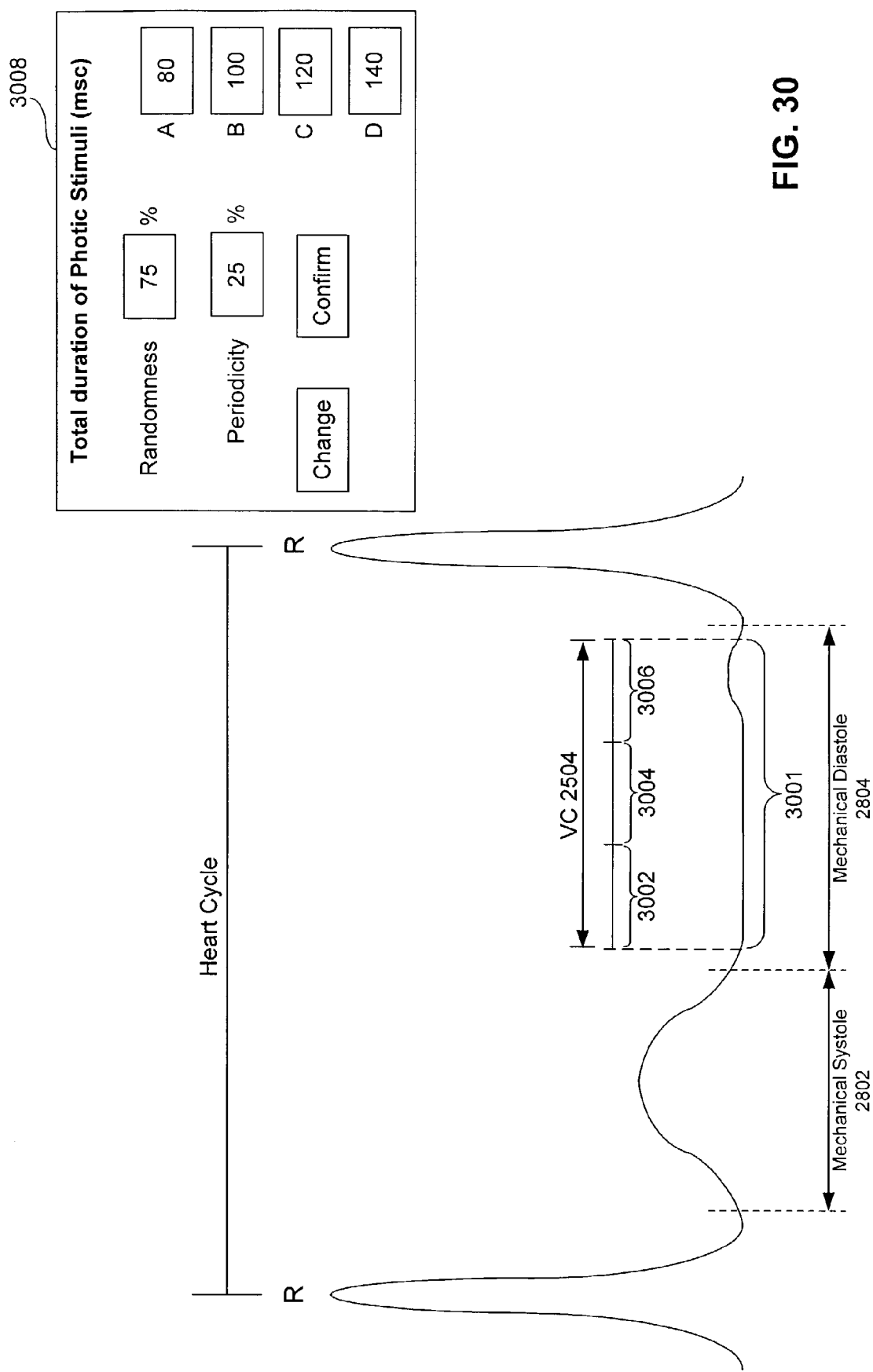

FIG. 30 illustrates the variability component that provides for four options for the total duration of three successive photic optical event changes in mechanical diastole according to an embodiment of the present invention.

Figure 31:
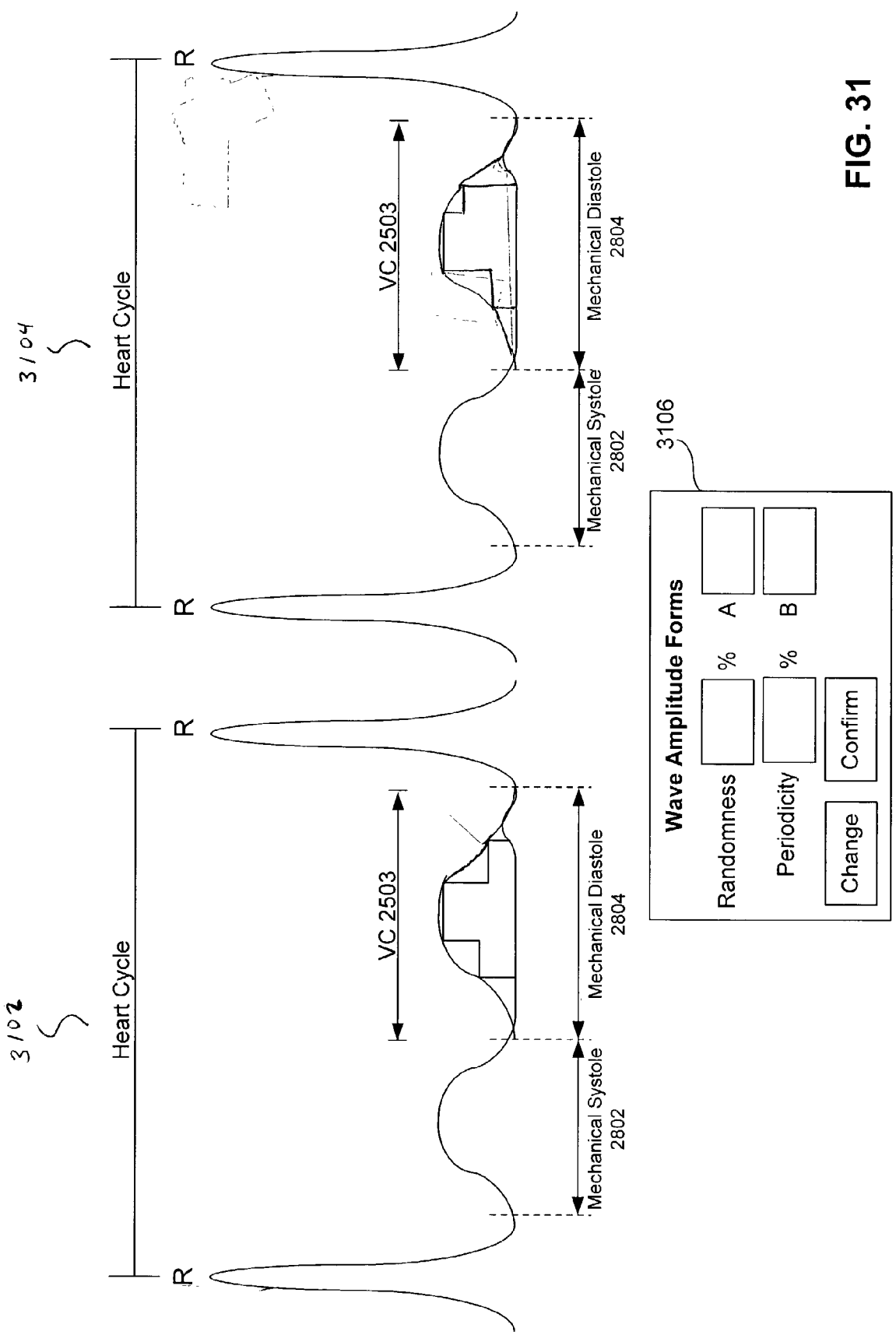

FIG. 31 illustrates the variability component that provides for two wave amplitude form options for the three consecutive photic changes during the optical event occurring in mechanical diastole according to an embodiment of the present invention.

Figure 32:
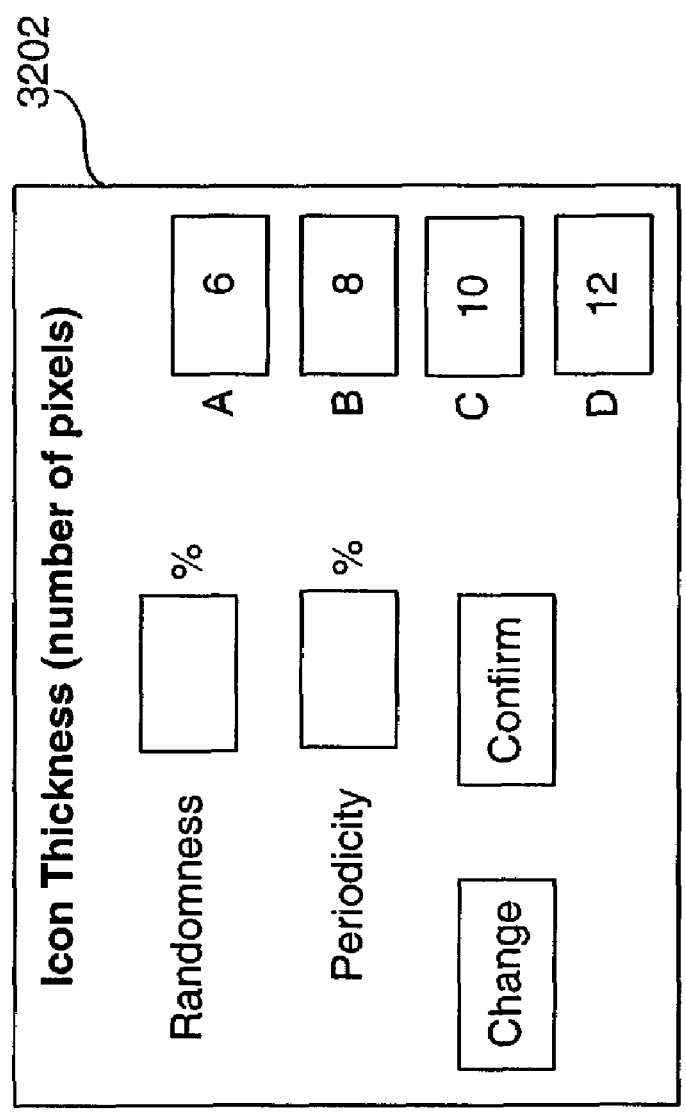

FIG. 32 illustrates the variability component that provides for a choice among four optical event icon thickness (defined as number of pixels) according to an embodiment.

Figure 33:
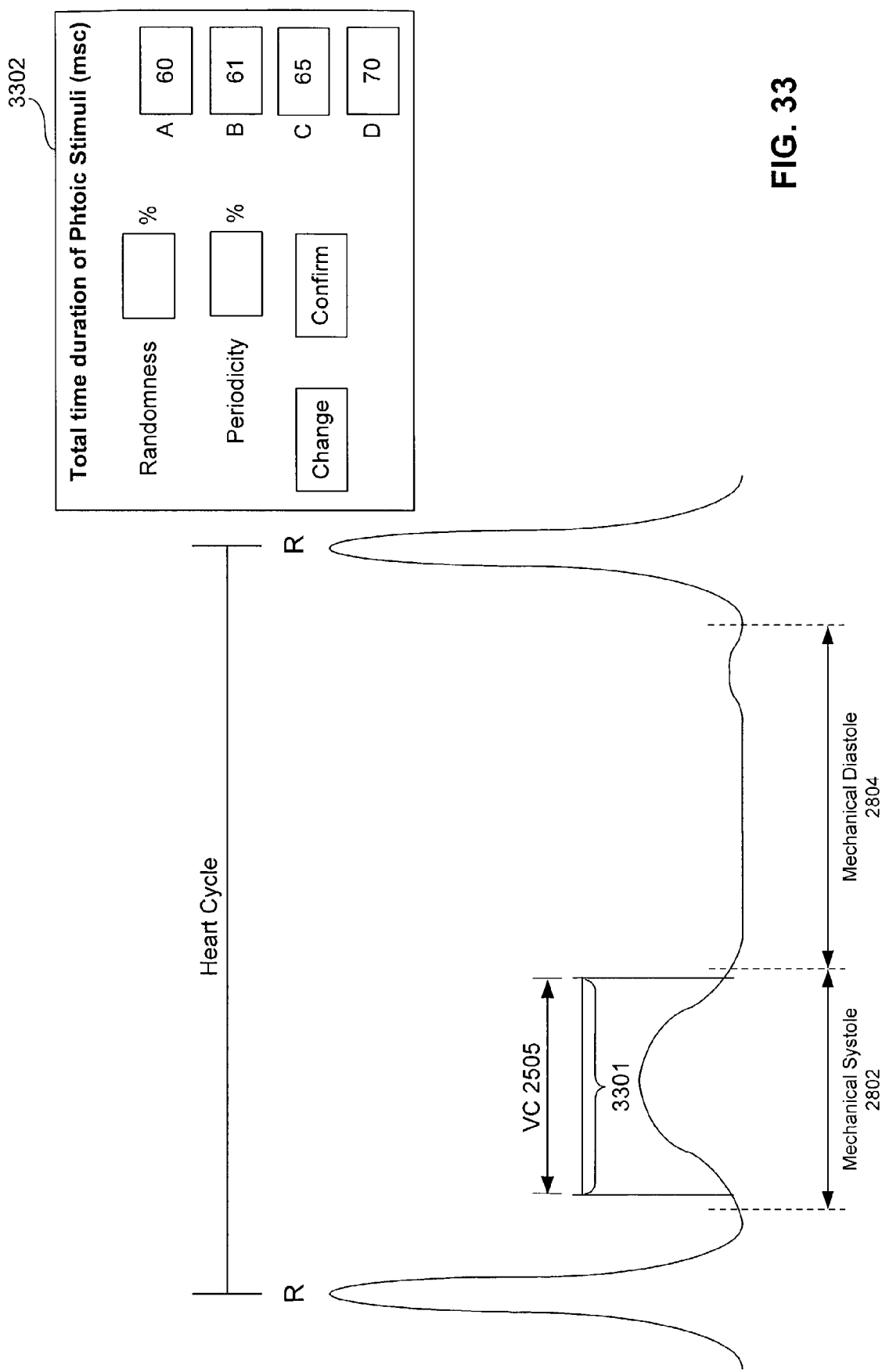

FIG. 33 illustrates the variability component that provides for four options for the total duration of the optical event icon (duration of the stimuli) in mechanical systole according to an embodiment of the present invention.

Figure 34:
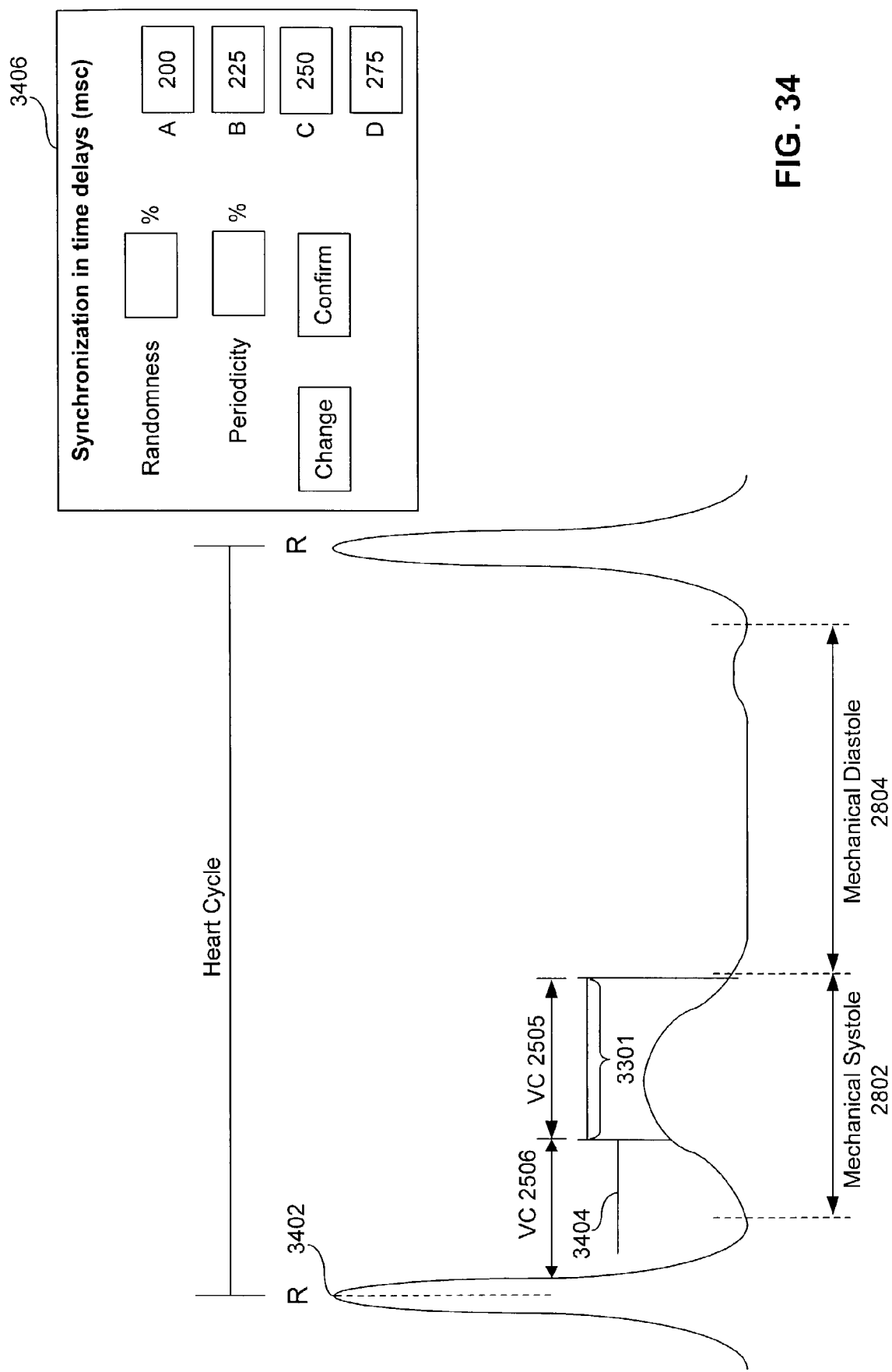

FIG. 34 illustrates the variability component that provides for four options for a time delay before the total duration of the optical event icon begins in mechanical systole according to an embodiment of the present invention.

Figure 35:
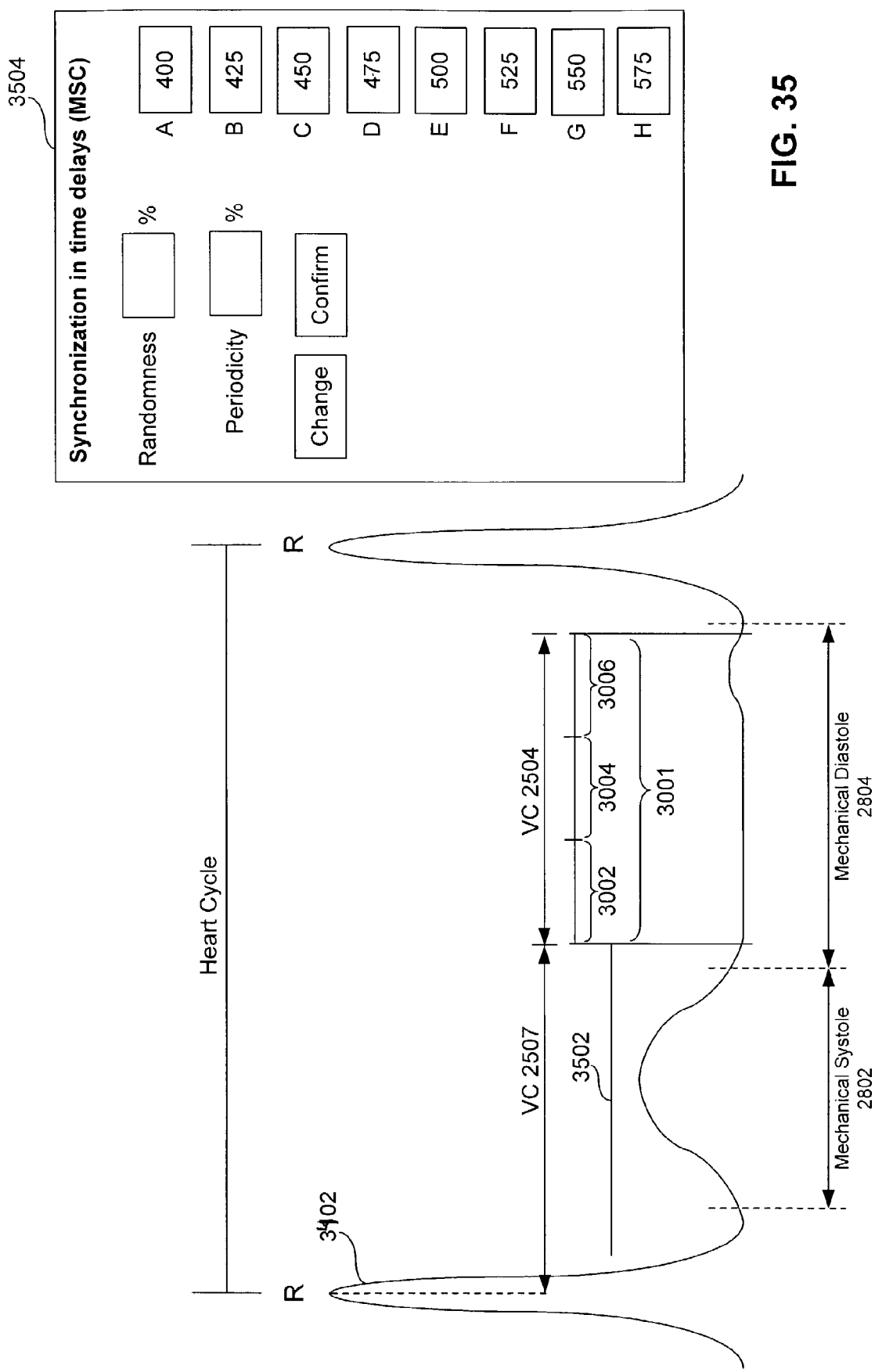

FIG. 35 illustrates the variability component that provides for eight options for a time delay before the total duration of the optical event icon begins in mechanical diastole according to an embodiment of the present invention.

Figure 36:
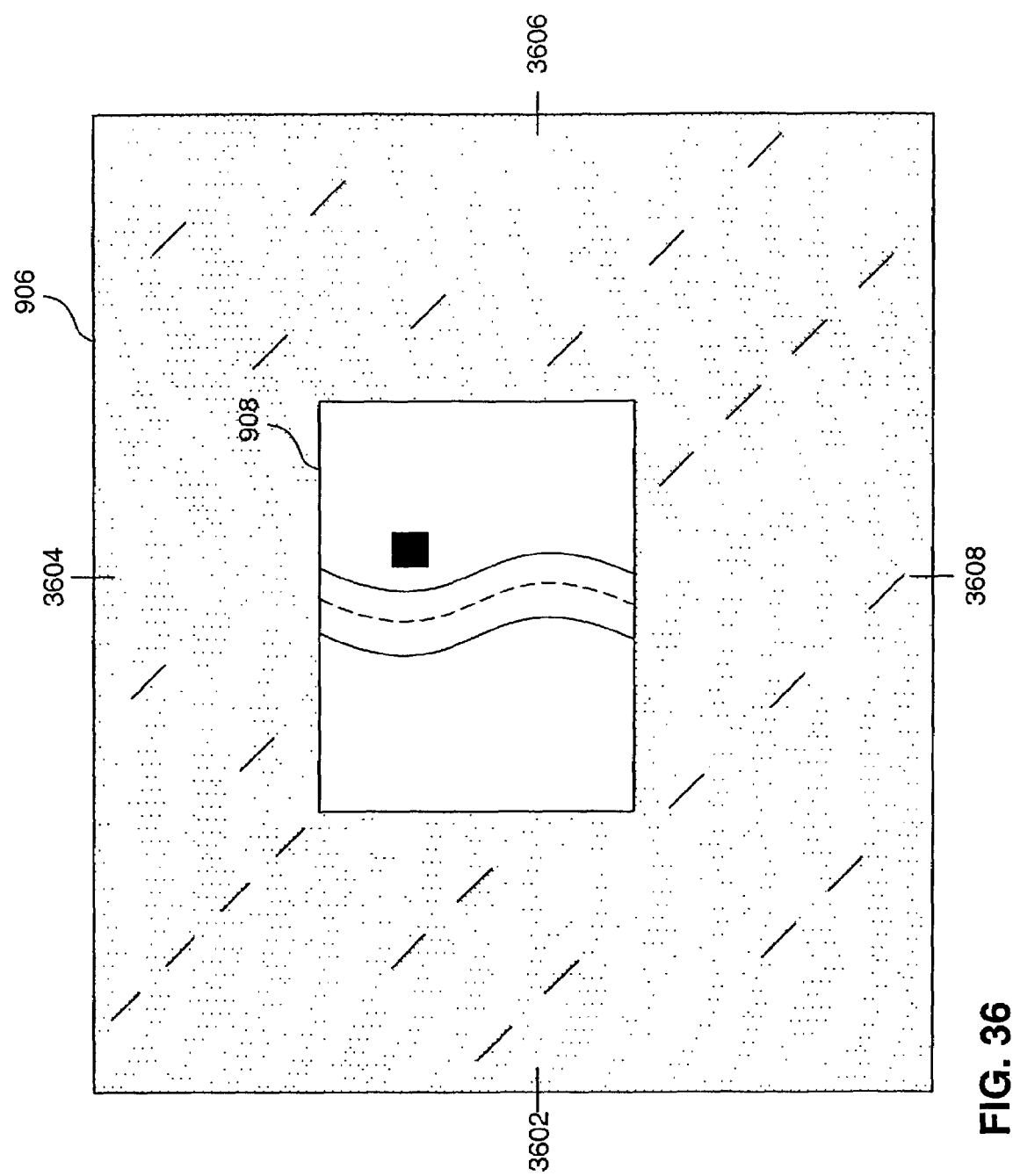

FIG. 36 illustrates the variability component that provides for four options of possible screen display zones that the optical event icon may perceptually emerge on the screen display of optical field output according to an embodiment of the present invention.

Figure 37:
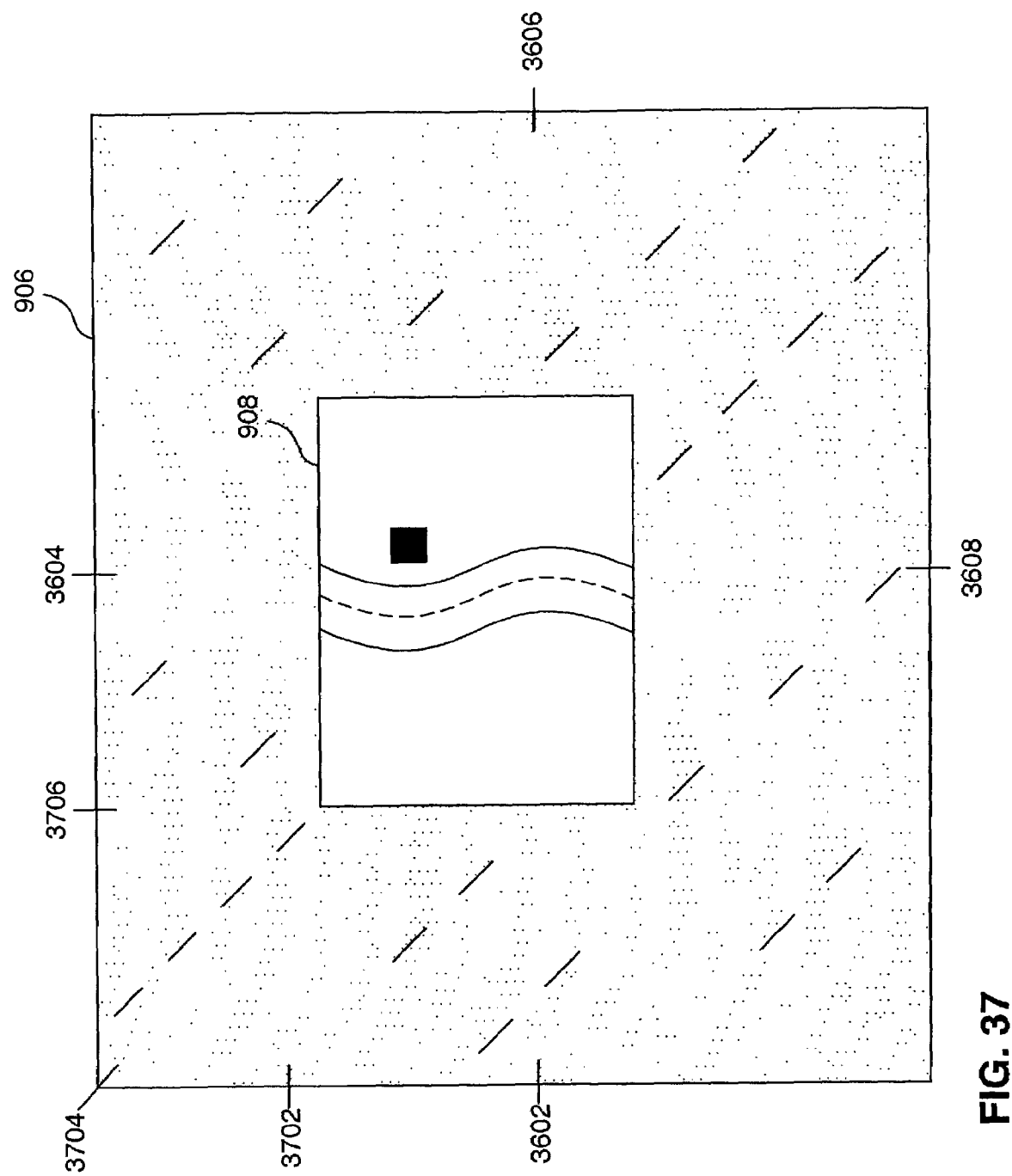

FIG. 37 illustrates the variability component that further sub-divides each of the four options of possible screen display zones into an additional four sub-zones according to an embodiment of the present invention.

Figure 38:
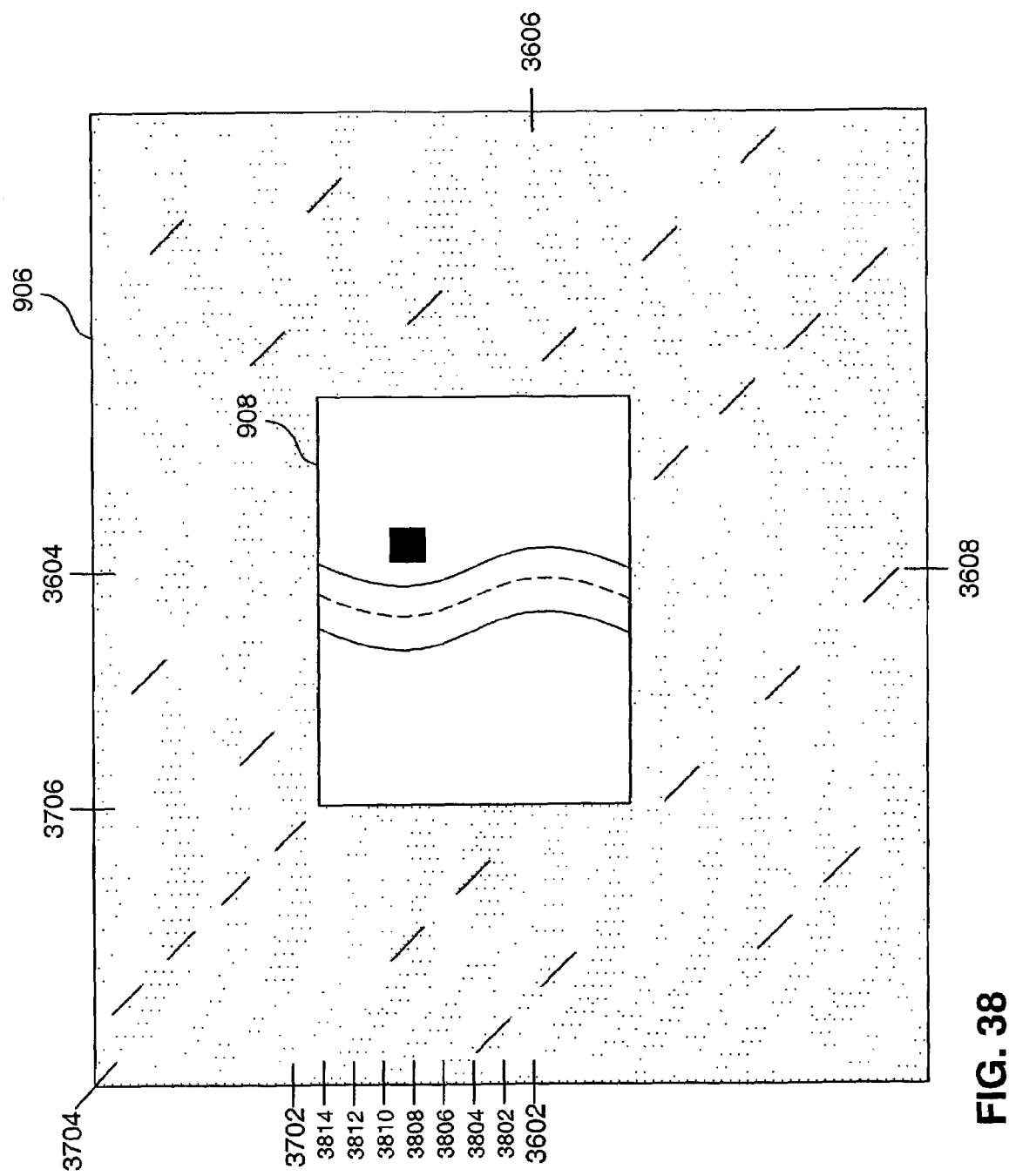

FIG. 38 illustrates the variability component that further sub-divides each of the sixteen sub-zones according to an embodiment of the present invention.

Figure 39:
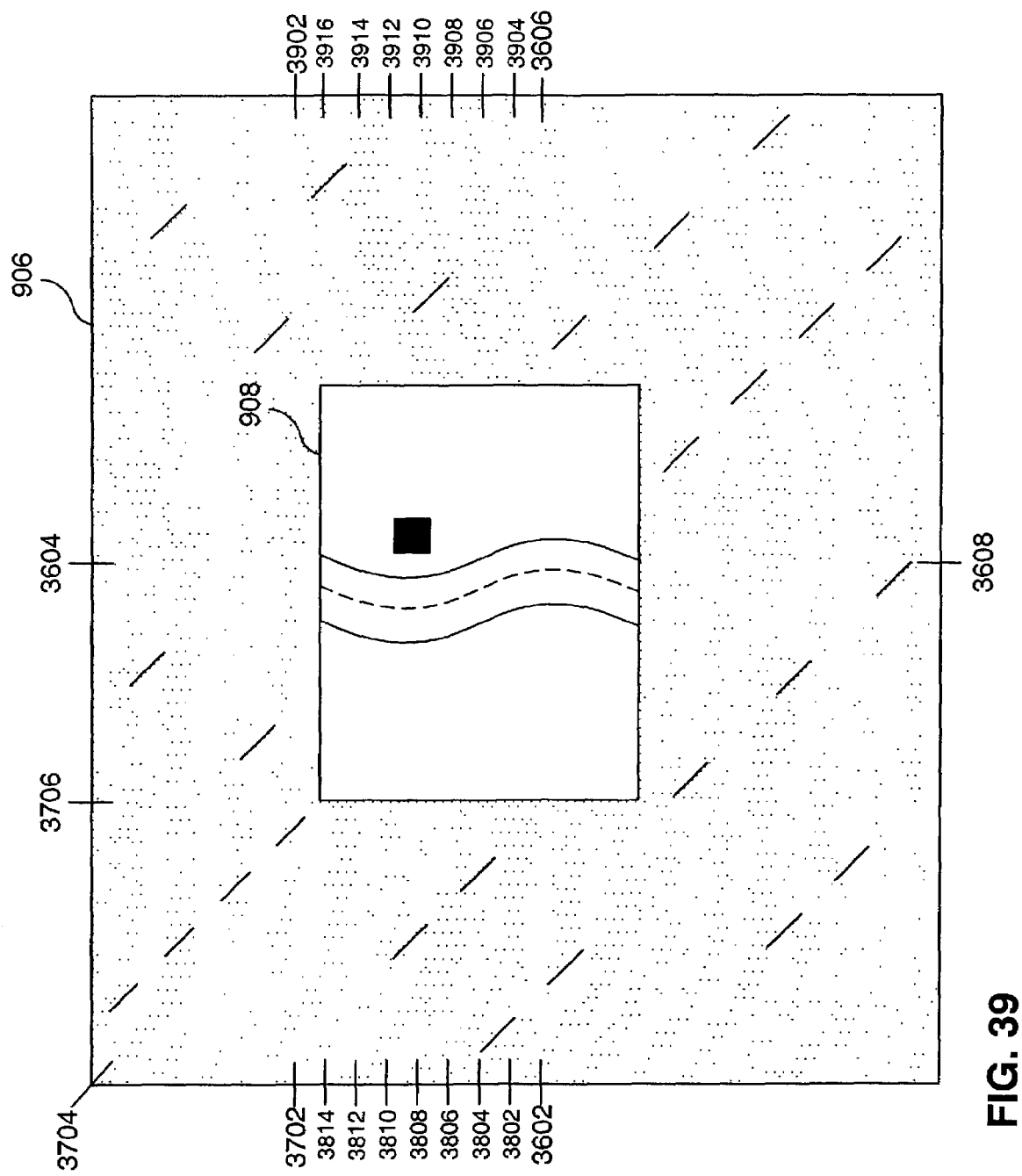

FIG. 39 illustrates the variability component that provides for eight different options for the optical event icon to perceptually terminate or arrive at the opposite and respective sub-zone from which it perceptually emerged according to an embodiment of the present invention.

Figure 40:
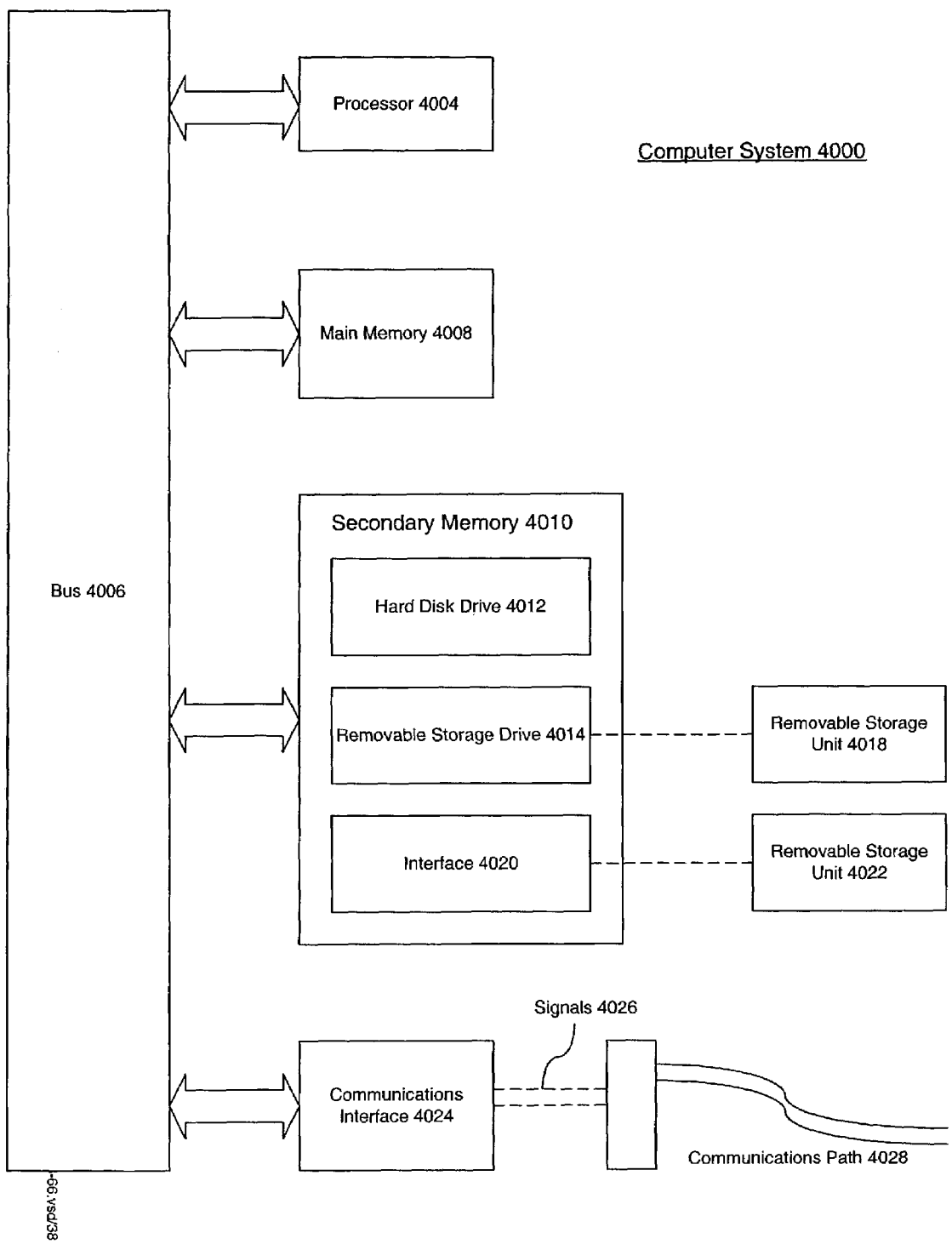

FIG. 40 illustrates a computer system that may be used to implement the optical events engine, as well as other modules, according to an embodiment of the invention.

Figure 41:
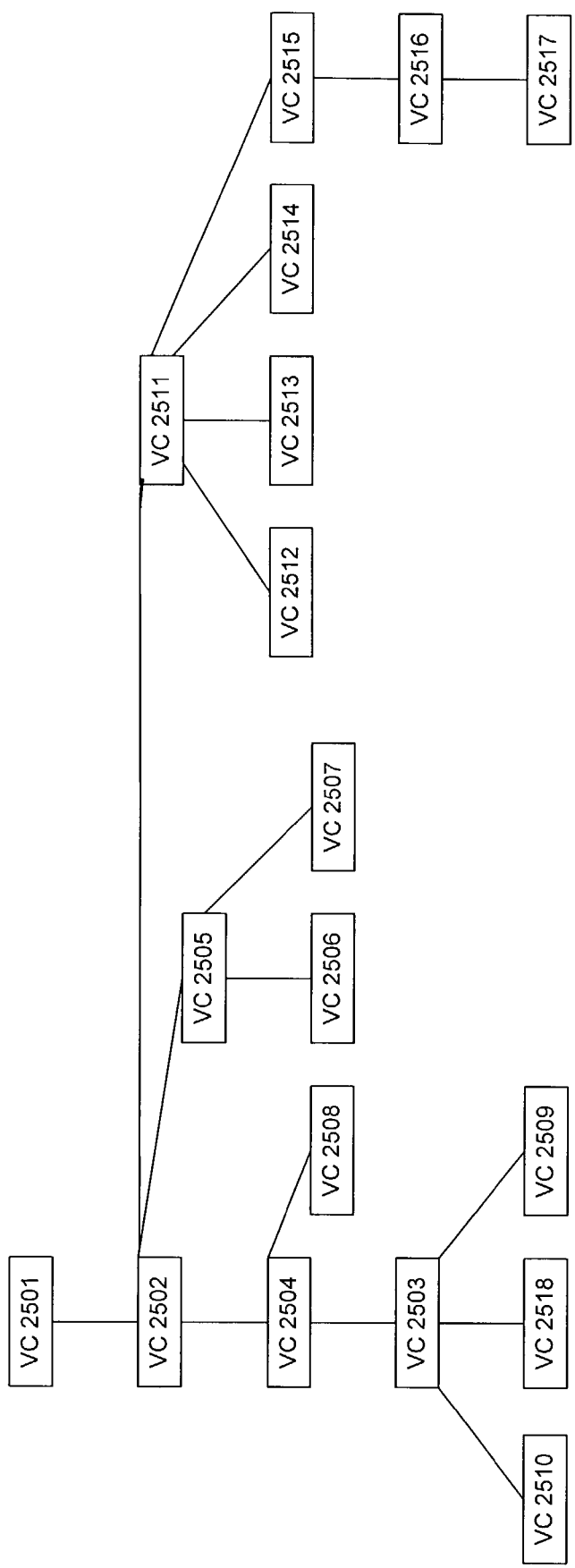

FIG. 41 illustrates an example variability component hierarchy tree according to an embodiment of the invention.

Figure 42:
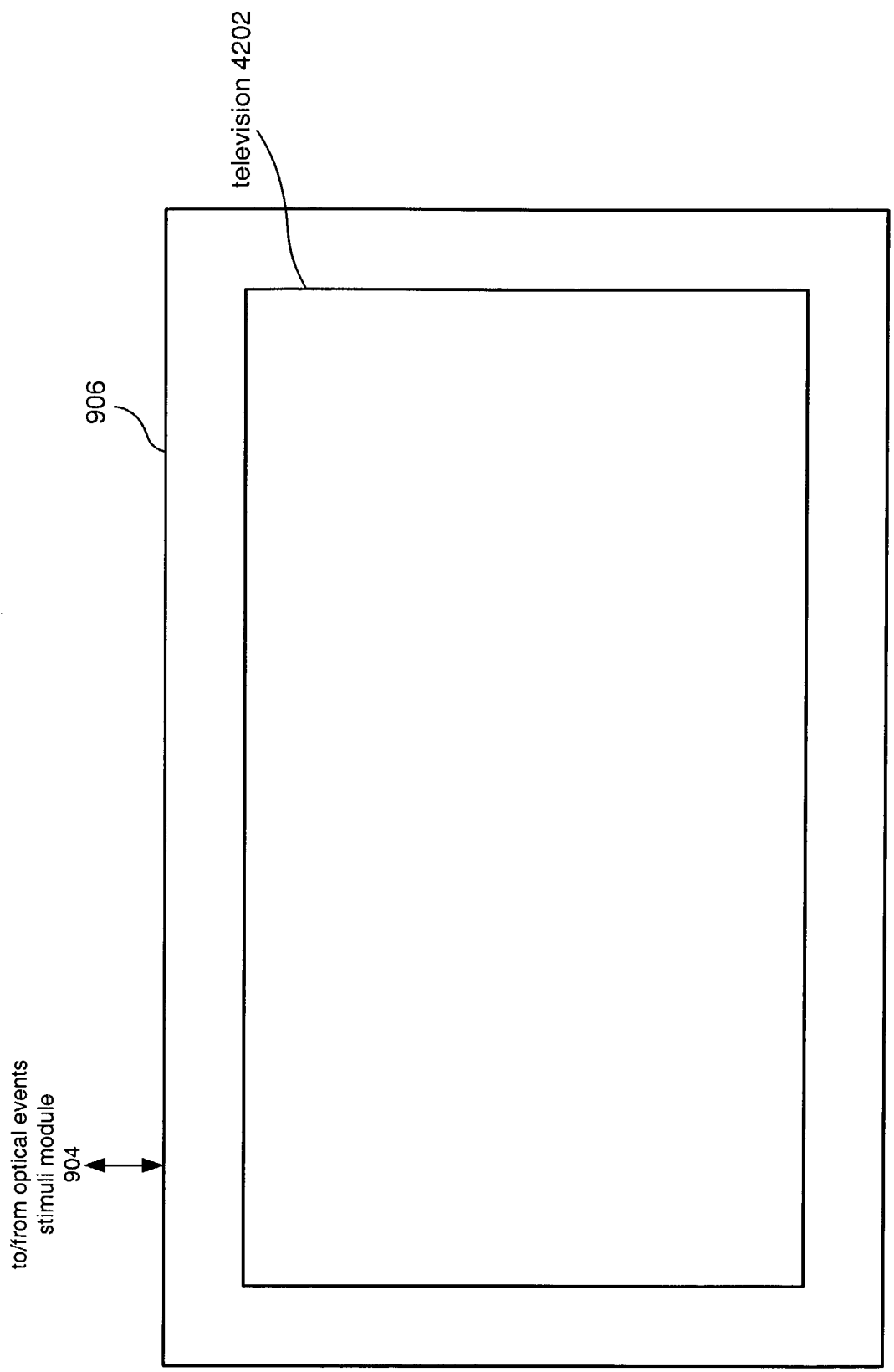

FIG. 42 illustrates an example embodiment of the invention as it relates to a television according to an embodiment.

Embodiments of the invention are described with reference to the figures where like reference numbers generally indicate identical or functionally similar elements. Also in the figures, generally, the left most digit(s) (either the first digit or first two digits) of each reference number identify the figure in which the reference number is first used.

DETAILED DESCRIPTION OF THE INVENTION

1. Introduction to the Invention

Perception is a process that bridges between reality and knowledge. An enigmatic bridge is embedded in biological activity, yet it is personally experienced in conscious awareness. In the development of the individual, perception is pivotal. Directly experiencing the physical world and learning social world and language, all people rely on the products of perception. In general, to the extent that perceptual ability is lacking in the beginning of life, these tasks (particularly sensory motor activity and some literacy skills) must be postponed or never accomplished by a person. Hence, its seems of critical importance to gain a clear understanding about perception concerning a rigorous analysis of the task of perception—what is to be perceived—and the ways in which environments make information available to accomplish that task.

J. Gibson (Gibson, J. J. (1966). The senses considered as perceptual systems. Boston: Houghton Mifflin & Gibson, J. J. (1979). The ecological approach to visual perception. Boston: Houghton Mifflin) pointed out the central importance of these questions around vision. Gibson stressed the importance of vision in guiding action, and also that vision cannot be divorced from the dimension of time. Gibson extensively studied the way environments interact with energy to provide information and accordingly he proceeded to make his central argument in visual perception and he called this enterprise "ecological optics." The term ecological designates facts at a level relevant to the perceiving organism. Not every fact about the spatiotemporal environment is relevant to the (survival) organism.

Perception in general begins with energy interactions at sensory receptors. Energy links the physical world of material structures and temporal events to the perceptual world in which objects and temporal events are represented. However, as Gibson pointed out, perceiving what is in the world is possible because interactions of energy with objects produce patterns across space and time. In fact, perception is not merely a response to local stimuli but is dependent on patterns in space and time. Accordingly, Gibson analyzed vision in terms of an informationally rich stimulus—the optic flow—that rendered redundant any requirement for internal representations of the world. He further, referred to the total pattern of light entering to the eye as the optic array, and the transformations of its informatically rich content often as a consequence of the observer's own movements, as the optic flow. Hence, a basic premise of ecological views is that the perceiving organism is awash not only in energy but also in information.

Ambient energy is structured by its interactions with objects, surfaces, and events. The attribute of patterning of energy by the physical layout makes the environment knowledgeable via direct (perceptual) detection of structure in the light array of energy (Gibson, J. J. (1966). The senses considered as perceptual systems. Boston: Houghton Mifflin). Gibson further argued that (biological) perceptual systems are geared to detect structure in ambient energy rather than properties of the energy itself (such as intensity and wavelength of light). In brief, biological visual perceptual systems may be specialized structures that take spatiotemporal patterns from ambient energy as inputs and generate meaningful, useful actions and descriptions (representations) of objects and events as outputs.

In addition, complex perceptual systems belong exclusively to mobile organisms. The ecology of any organism is conditioned by its capacities for action, just as it is conditioned by the information available for perception. Perception and action are so dramatically entwined that it's unimaginable that the evolution of the one without the other could occur. According to Gibson, human and animal behavior might be described in terms of "perception-action loops" (Gibson, J. J. (1966). The senses considered as perceptual systems. Boston: Houghton Mifflin). Here, the organism's (intrinsic) physiological activity triggers perpetual adjustments upon active perceptual systems facilitating the extraction of information, which is used in guiding motor action and additional seeking of information (Gibson, J. J. (1979). The ecological approach to visual perception. Boston: Houghton Mifflin; Mace, W. M. (1974). Ecologically stimulating cognitive psychology: Gibsonian perspectives. In W. B. Weimer & D. S. Palermo (Eds.), Cognition and the symbolic process (pp. 137-164). Hillsdale, N J: Erlbaum; Turvey, M. T., Shaw, R. E., Reed, E. S., & Mace, W. M. (1981). Ecological laws of perceiving and acting: In reply to Fodor and Pylyshyn. Cognition, 9, 237-304).

One such an example of unconscious and active perceptual adjustments taking place in the organism is provided by information for postural stability, which can be generated by proprioceptive, vestibular, and visual information. Much of our orienting and acting in the environment, however, depends on information we receive through vision. Gibson (Gibson, J. J. (1966). The senses considered as perceptual systems. Boston: Houghton Mifflin) drew attention to the crucial role played by vision, coining the phrase "visual kinesthesis." Hence, posture will be corrected every second or two accordingly without conscious awareness, based primarily on visual information. Optic flow alone can induce to a moving observer important property of his/her locomotion such as heading.

Coincidentally, the key tenet to the ecological approach has to do with an analysis of Berkeley's Essay Towards a New Theory of Vision (Berkeley, G. (1709/1910). London: Dutton). Berkeley pointed out that that the projection of an object onto the retina of a single eye is inherently ambiguous. In fact, an infinite number of variously sized and shaped objects in the world could give rise to the same retinal image. If visual patterns are ambiguous, then some nonvisual information is needed to disambiguate them. Berkeley suggested that the nonvisual information was provided by the oculomotor cues of accommodation and convergence. In each case, the muscular contractions required to accomplish a task would correlate with physical distance to the target and the muscle sensations could provide cues of depth.

Berkeley's analysis of ambiguity is technically correct if one considers only the information available in: (a) a momentary image—optical information remains invariant (temporally frozen) for a defined interval of time; and (b) information is projected to only a single eye. Human perception, however, does not work that way. Gibson argued that the best information available to perceivers is information that has expanded and has taken structure in time. Looking with a single eye through a peephole, a three-dimensional scene may be indistinguishable from a photograph or photorealistic painting. Assuming the environment to be at rest, when the perceiver views the scene or photograph while walking, the pattern of optical changes (optical flow) furnishes unequivocal information about the 3D spatial structure in the scene, with the relations between optical transformations and the real scene specified by the laws of projective geometry. Kinematical information, given by observer self-motion at all levels or by object motion, is fundamental to ordinary perception. Most importantly, the momentary (temporally frozen optical image) image considered by Berkeley may be a degenerative input (lacking in temporal and/or spatial structure) to biological perceptual systems (Gibson, J. J. (1966). The senses considered as perceptual systems. Boston: Houghton Mifflin & Gibson, J. J. (1979). The ecological approach to visual perception. Boston: Houghton Mifflin; Johansson, G. (1970). On theories for visual space perception: A letter to Gibson. Scandinavian Journal of Psychology, 11(2), 67-74).

The above arguments regarding ecological visual perception are especially fruitful for gaining an understanding about the pivotal role assigned to visual perceptual maturation in an individual's development. Especially since Gibson has incorporated the time dimension in perception, so that all perception becomes, in essence, motion perception.

According to Piaget's constructivist perceptual account, (Piaget, J. 1952. The origins of intelligence in children. New York: International Universities Press & Piaget, J. 1954. The construction of reality in the child. New York: Basic Books & Piaget, J. 1976. The psychology of intelligence. [Translated from French by Malcolm Piercy and D. E. Berlyne]. Totowa, N.J.: Littlefield, Adams.) but more so the Gibsonian ecological perceptual account, sensory motor activity and visual perception are both extremes of one and the same process. Hence, it shouldn't come as a surprise that sensory motor activity and literacy skills will suffer a common fate. Developmental impairments influencing visual perception will inevitably down play the potential of a subject to directly extract kinematical attributes from the environment. More so, visual perceptual deficiency at the biological level may well affect magnocellular detection of transient stimuli, resulting in a poor capacity for mapping spatial structure and locomotion, which in turn particularly manifest in a noisy guided sensory motor activity in the subject's reachable space. If motor fluency were compromised at many levels, then top-down processes and resources will shift their functional capacity away from accomplishing cognitive information processing of representations. Thus, affecting the subject's capacity for discriminating and categorizing spatiotemporal features in the environment such as size, color and shape of objects.

In short, an early dominant visual perceptual deficiency may hinder or delay the subject's capacity for making causal experiential associations (memories) among spatiotemporal structures in the environment and therefore, constraining his/her potential for subjectively inferring via language and thought about the habitat at large. Under such circumstances the potential for cognitive learning behavior in a subject surfaces out as a very implausible task to be accomplished.

Learning disabilities in general and dyslexia in particular are potential logical targets for a poor or mal-realization of visual perceptual-motor processes in early life. Hence, we herein introduce and discuss in length "Developmental Dyslexia" as an example of being a high profile candidate, where early visual perceptual-motor deficits have disrupted functional capacities in the individual at the biological, perceptual and cognitive levels respectively. This discussion of developmental dyslexia is for illustrations purposes only and is not meant to limit the invention.

Learning disabilities in general and developmental dyslexia in particular, sit on the crossroads of several scientific domains that overlap with each other. Developmental dyslexia is a topic that fuses together many distinct disciplines into one integrative whole, i.e., an original multidisciplinary topic. Along the presentation of the related art in developmental dyslexia, scientific evidence is provided herein that embraces several disciplines such as neurophysiology, visual processing and perception, cognitive psychology, ecological psychology, and physiological motor control. Although at prima face, the related art is well diversified, it is finally converging into a common and well-interconnected biological background, where the role of early perceptual-motor processes play a decisive role in solidifying a biological hypothesis for the causation of developmental dyslexia.

The word 'dyslexia' originates from Greek, meaning 'difficulty with words or language.' Developmental dyslexia is traditionally defined as:

'A disorder in children who, despite conventional classroom experience, fail to attain the language skills of reading, writing and spelling commensurate with their intellectual abilities.'

This definition is helpful in that it describes what all dyslexics have in common. But, it does not tell the whole story. Dyslexic children have problems in many other areas such as differentiating between left and right, tying shoe laces, learning to tell time, following instructions, math, organizational skills, memory and auditory processing (for example, confusing spoken sounds such as /v/, /th/ and /f/ in words like 'live', 'lithe' and 'life'). In short, no two dyslexics are alike—each dyslexic has his/her own set of weaknesses and strengths. Three to ten percent of the population is so affected.

During the early 1990's, the dominating view in dyslexia among international researchers was in terms of defining dyslexia as a phonological deficit account. Seminal research by Bradley and Bryant, Frith and Snowling viewed dyslexia in children as a core deficit attributable to brain abnormalities in the language areas. This deficit translated in children into having a greater difficulty at school age in hearing the individual sounds in spoken words. This difficulty consequently makes it more difficult for children to learn to read because of a poor awareness of phonological features such as rhyme. Phonological awareness is considered the corner stone when building up the rules of grapheme to phoneme translation rules.

The fact that dyslexia can show itself in so many ways, and can result from different causes, has created not only disagreement among researchers but also produced several definitions. Among such definitions we shall consider a definition (Augur, J. (1993) 'Guidelines for teachers, parents and learners' in Snowling, M. (Ed) (1993) Children's Written Language Difficulties, Assessment, and Management, London: Routledge 1) that defines dyslexia as:

'A specific difficulty in learning, in one or more of reading, spelling and written language which may be accompanied by difficulty in number work, short-term memory, sequencing, auditory and/or visual perception, and motor skills. It is particularly related to mastering and using written language—alphabetic, numeric and musical notation. In addition oral language is often affected to some degree.'

To make sense of the overall complicated picture, Frith (Frith U 1997. Brain, mind and behavior in dyslexia. In C Hulme, M Snowling (eds) Dyslexia: Biology, Cognnition and Intervention. London: Whurr) has provided a model that calls attention to three different levels at which one can talk about the phenomena of dyslexia: the biological level, the cognitive level and the behavioral level. The biological level attempts to identify the underlying brain mechanisms: disorganization in cerebral cortex in the language areas, abnormal magnocellular pathways, abnormal cerebellum, and so forth. The cognitive level attempts to provide an explanation in terms of theoretical models based in cognitive psychology: reduced working memory, poor phonological processing, incomplete automatization, slow central processing, and so forth. The behavioral level finds its expression in terms of symptoms: poor reading, difficulty with rhymes and writing. According to this model, there may be some biological abnormality—sometimes genetically determined.

At all of these levels, the influence of the environment is at work, causing the eventual outcome to be modified; this is true even of the environment in the womb before birth. In short, it is not that any one level of explanation is intrinsically 'better' than another; a complete explanation would involve all three.

Frith's model has widened the field of dyslexia into considering an integrative causal approach not only in terms of defining the syndrome itself, but also in the scope of its potential research. New theories have been suggested, both in terms of magnocellular deficit (Stein J, Walsh V 1997 To see but not to read; the magnocellular theory of dyslexia. Trends in Neurosciences 21: 590-612) and of cerebellar deficit (Fawcett A J, Nicolson R I, Dean P 1996 Impaired performance of children with dyslexia on a range of cerebellar tasks. Annals of Dyslexia 46: 259-83). Both theories provide a causal explanation at the biological level and can be interpreted as describing parallel mechanisms that converge into common trends at several points. Both theories also suggest that problems associated with dyslexia, as already briefly mentioned above, reflect a more widespread spectrum of difficulties than just a phonological deficit account.

The visual magnocellular deficit hypothesizes that dyslexic readers suffer from visual deficits (Lovegrove, W. J., Martin, F., and Slaghuis, W. 1986. A theoretical and experimental case for visual deficit in specific reading difficulty. Cog. Neuropsychol. 3:225-267; Lovegrove, W. J., Garzia, R. P. and Nicholson, S. B. (1990) Experimental evidence for a transient system deficit in specific reading disability. Journal of American Optometrists Association, 61, 137-146; Skottum, B. C. (2000). The magnocellular deficit theory of dyslexia: the evidence from contrast sensitivity. Vision Research, 40, 111-127; Wright, B. A., Bowen, R. W., & Zecker, S. G. (2000). Nonlinguistic perceptual deficits associated with reading and language disorders. Current Opinion in Neurobiology, 10 482-486) and attempts to establish a relationship that would define and also alter the degree of dyslexia by manipulating purely visual variables (O'Brien, B. A., Mansfield, J. S., & Legge, G. E. (2000). The effect of contrast on reading speed in dyslexia. Vision Research, 40, 1921-1935).

In a broad context, the magnocellular deficit supports the hypothesis that reading problems are a consequence of impaired sensory processing, caused by abnormal auditory and/or visual development of a system of large neurons in the brain (magnocells) that is responsible for timing sensory and motor events.

In the visual system, visual pathways have two major routes, including (1) the 'retinocalcarine' from the retina via the optic nerve, optic chiasm and the lateral geniculate nucleus (LGN) in the thalamus to the primary visual cortex, and (2) the 'tectal' pathway via the superior colliculus (SC) and the pulvinar (P) to the associative cortices.

More so, about 10% of retinal ganglion cells are much larger magnocellular M-cells that signal the timing of visual events, not their form. It has become widely accepted that visual transient processing is mainly mediated by M-cells that have rapid temporal dynamics in both the peripheral and central visual systems (Merigan, W. H and Maunsell, J. H. R. (1993) How parallel are the primate visual pathways? Annu. Rev. Neurosci. 16, 369-402).

Experiments in the visual cortical areas of monkeys have clearly demonstrated that moving stimuli are the most selective for this magnocellular transient system (Newsome, W. T. and Pare', E. B. (1988) A selective impairment of motion processing following lesions of the middle temporal visual area (MT). J. Neurosci. 8, 2201-2211). It has also been found that visual motion sensitivity in dyslexics is indeed reduced (Cornelissen, P. et al. (1995) contrast sensitivity and coherent motion detection measured at photopic luminance levels in dyslexics and controls. Vis Res. 35, 1483-1494) and therefore the degree of the individual's reduction in motion sensitivity correlates with his own visual impairment (Witton, C. et al. (1998) Sensitivity to dynamic auditory and visual stimuli predicts nonword reading ability in both dyslexic and normal readers. Curr. Biol. 8, 791-797).

The idea that many, if not most, developmental dyslexics have mildly to strongly impaired development of the visual magnocellular system is firmly rooted. Livingstone and Galaburda have demonstrated with strong and convincing evidence that in post-mortem dyslexic brains neurons in the magnocellular layers of the lateral geniculate nucleus (LNG) were smaller and more disorganized than in control brains (Livingstone, M. S et al. (1991) Physiological and anatomical evidence for a magnocellular defect in developmental dyslexia. Proc. Natl. Acad. Sci. U.S.A. 88, 7943-7947). Hence, M-cells are important for detecting visual motion (Enroth-Cugell C, Robson J G (1966). The contrast sensitivity of retinal ganglion cells in the cat. J. Physiol 187: 517-52; Shapley, R., and Perry, V. H. 1986. Cat and monkey retinal ganglion cells and their visual functional roles. Trends Neurosci. 9:229-235; Merigan, W. H and Maunsell, J. H. R. (1993) How parallel are the primate visual pathways? Annu. Rev. Neurosci. 16, 369-402).

In contrast, the parvo P-cells in the visual system is composed in its majority (about 90%) of retinal ganglion cells that are smaller in size and that signal fine detail and color of objects. Magno cells have a considerable dendritic area, hence their receptive fields' size is approximately 500 times that of parvo cells. Magno cells also have rapid membrane dynamics so that they can signal sharply the onset and offset of stimuli. Their heavily myelinated axons conduct signals to the cerebral cortex approximately 20 ms faster than parvo cells (Bullier, J., & Nowak, L. G. (1995). Parallel versus serial processing; new vistas on the distributed organization of the visual system. Current Opinion in Neurobiology, 5(4), 497-503). Signals project to the magnocellular layers of the thalamic visual relay nucleus (LGN) and from there onwards to layer IV-5 of the primary visual cortex in the calcarine fissure of the occipital lobe.

In the retinocalcarine pathway, despite the intermingling of parvo and magno pathways in the primary and in the other visual cortical areas, two main output streams of visual processing have been identified (Ungeleider, L. G., & Mishkin, M. (1982). Two cortical visual systems. In D. J. Ingle, M. A. Goodale, & R. J. W. Mansfield (Eds.), Analysis of visual behavior (pp. 549-586). Cambridge, Mass.: MIT Press). Both output streams originate from the visual cortical areas, but one passes dorsally to the posterior parietal areas of the cortex and the other passes ventrally to the inferotemporal cortex.

The dorsal stream analyses aspects of movement and depth in the pattern of stimulation, and since these signals provide information about the timing of visual events and of the motion of visual targets, the dorsal system is important for the guidance of both eye and limb movement (Milner, A. D., & Goodale, M. A. (1995). The visual brain in action. Oxford, England UK: Oxford University Press). Likewise, dorsal projections are linked to the motor structures (including the frontal eye fields, and the superior colliculus) and also provide a very large input to the cerebellum (Stein J F, Glickstein M (1992). The role of the cerebellum in the visual guidance of movement. Physiological reviews 72: 967-1018) via the pontine nucleus.

The dorsal stream in the retinocalcarine pathway receives its main (if not total) input from the magnocellular body cells (Merigan, W. H and Maunsell, J. H. R. (1993) How parallel are the primate visual pathways? Annu. Rev. Neurosci. 16, 369-402). The ventral stream extracts spatial detail and color and appears to receive its major input from the parvocellular retinocalcarine pathway, although it also receives considerable magnocellular input. In the one hand, the dorsal system appears not to have a long-term storage of information, but only a very short-term storage that allows the execution of the motor behavior in question. On the other hand, the ventral system is a memory-based system, utilizing stored representation to recognize and identify objects and events. Accordingly, perceiving the location of an object was attributed to the dorsal stream while the ventral stream determined its identity (the where and what dimension of vision) (Goldtein, E. B. (1999). Sensation and perception (5th ed.). Pacific Grove, Calif.: Brooks/Cole).

The magnocellular system is crucial for controlling eye movements and ensures the steady control of eye fixation to targets during the process of reading. The magnocellular/transient neural circuitry projects densely to the cerebellum, a brain structure that plays a decisive role not only in the reading process but also in 'inner speech.' Furthermore, the magnocellular pathway is highly implicated in the processing of motion information (Logothetis, N. K. (1994). Physiological studies of motion inputs. In A. T. Smith (Ed.), Visual detection of motion (pp.177-216). London: Academic Press). Accordingly, the bulk of motion analysis is carried out in the dorsal system, mainly in areas middle temporal (MT) and medial superior temporal (MST) (Logothetis, N. K. (1994). Physiological studies of motion inputs. In A. T. Smith (Ed.), Visual detection of motion (pp.177-216). London: Academic Press). In the macaques, the dorsal system inputs are from areas dealing with spatial or motion analysis and are from peripheral representations of the retina. The ventral system inputs are from areas dealing with form and color analysis (V4) from more central representations of the retina (the fovea) (Baizer, J. S., Ungerleider, L. G., & Desimone, R. (1991). Organization of visual inputs to the inferior temporal and posterior parietal cortex in macaques. Journal of Neuroscience, 11(1), 168-190).

Turning our attention to the common trends existing between the magnocellular and cerebellar hypothesis, we could safely say that reading difficulties in this context are a consequence of disturbed development of a generalized magnocellular system that is under common genetic control and responsible for timing sensory and motor events. Thus, we should expect that a wide set of functions which involve the cerebellum would be impaired in dyslexics. Our focus on the cerebellum is particularly significant because this structure is the recipient of heavy projections from all the magnocellular systems throughout the brain. More specifically, the largest output of the dorsal "where" visual magnocellular route is to the cerebellum via the pontine nuclei (Stein J F, Glickstein M (1992) The role of the cerebellum in the visual guidance of movement. Physiological reviews 72: 967-1018). Therefore, we can view the cerebellum itself as a quintessentially magnocellular structure.

The view that the cerebellum is involved in cognitive skills is relatively new and stands in contrast to the traditional role attributed to the cerebellum as a motor area. The cerebellum is being preferentially involved in controlling complex movements, multijoint movements, and movements that require visuomotor coordination or learned automatic movements (Stein J F, Glickstein M (1992) The role of the cerebellum in the visual guidance of movement. Physiological reviews 72: 967-1018; Thach W. T., H. P. Goodkin and J. G. Keating, (1992). The cerebellum and the adaptive coordination of movement. Ann Rev Neurosci 15: 403-442). However, the human cerebellum has evolved enormously, becoming linked with areas in the frontal cortex, including Broca's language area.

It has been proposed that the cerebellum is critically involved in the automatization of any skill, whether motor or cognitive. There is now overwhelming evidence of the importance of the cerebellum in language (Ackermann H, Hertrich I (2000). The contribution of the cerebellum to speech processing. Journal of Neurolinguistics, 13(2-3): 95-116) including specific cerebellar involvement in reading (Fulbright R K, Jenner A R, Mencl W E, Pugh K R, Shaywitz B A, Shaywitz S E, Frost S J, Skudlarski P, Constable R T, Lacadie C M, Marchione K E, Gore J C (1999). The cerebellum's role in reading: a functional MR imaging study. American Journal of Neuroradiology 20: 1925-30).

Nicolson and Fawcett (Nicolson R I, Fawcett A J (1990) Automaticity: a new framework for dyslexia research? Cognition 35(2): 159-82) originally hinted for a potential cerebellar dysfunction, by accumulating evidence showing that dyslexics have difficulty in acquiring automaticity, that is, require more practice than controls before learned skills become automatic. Indeed, Fawcett et al. (Fawcett A J, Nicolson R I, Dean P (1996) Impaired performance of children with dyslexia on a range of cerebellar tasks. Annals of Dyslexia 46: 259-83) have shown that dyslexics perform worse than normal on classic tests of cerebellar function, including balance and muscle tone.

In a study conducted by Nicolson et al. (Nicolson R I, Fawcett A J, Dean P (1995) Time-estimation deficits in developmental dyslexia-evidence for a cerebellar involvement. Proceedings of the Royal Society of London Series B-Biological Sciences 259: 43-7), evidence was provided for a time estimation task deficit in dyslexic subjects, which is believed to be an index of cerebellar functioning. In general, damage to the cerebellum disrupts performance on a range of tasks that require precise timing, including the production of skilled movements, eye blink conditioning, and perceptual tasks such as (temporal) duration discrimination.

It is hypothesized that such tasks that require precise timing involve event timing, a form of mental representation in which temporal goals are explicitly represented (Ivry, R. B., Spencer, R. M., Zelaznik, H. N., and Diedrichsen, J. (in press-2002). The cerebellum and event timing. To appear in S. M. Highstein and W. T. Thach (Eds.), New Directions in Cerebellar Research, Annala of the New York Academy of Sciences). The emphasis of this approach has been to describe mental operations in terms of the representation and transformation of information, being recruited whenever their specialized operations are required. Furthermore, temporal control of a repetitive series of discrete movements requires an explicit temporal representation. Psychologically, this representation specifies when particular events should occur or have occurred. Timing remains an explicit part of the representation of the task goal. For example, in finger tapping, the cerebellum signals when the next response should occur.

Moreover, in a similar context, the event-timing hypothesis is also likely to be relevant in evaluating the present trend of thought about the relationship of timing and prediction. Representing when the next finger tap should occur or when an air puff will be experienced are forms of prediction. It has been proposed that the fundamental property of cerebellar function is its operation as a predictive device. In sensorimotor control, this idea is captured by the formalism of internal, forward models (Wolpert, D. M., Ghahramani, Z., & Jordan, M. I. (1995). An internal model for sensorimotor integration. Science, 269, 1880-1882; Wolpert, D. M., Miall, R. C., & Kawato, M. (1998). Internal models in the cerebellum. Trends in Cognitive Science, 2, 313-321; Block R. A., & Zakay D. (1996). Models of psychological time revisited. In H. Helfrich (ed.), Time and Mind. Bern: Hogrefe and Huber Publishers. (pp. 171-195). For example, the cerebellum might contribute to problem solving by supporting internal simulations that test out possible solutions to see if the end result matches the goal.

Prediction is somehow ubiquitous in timing, and research in the functional domain linking the cerebellum to cognition has provided substantial evidence that the cerebellum plays a critical role in situations that required real-time predictions. In short, the cerebellum operates an internal timing system which can be used in various tasks and may be a vital component of skilled movement behaviors (Lundy-Ekman, L., Ivry, R., Keele, S. and Woollacott, M. (1991) 'Timing and force control deficits in clumsy children', Journal of Cognitive Neuroscience, 3, 367-376).

What about the cerebellum's role in phonological processes? It was suggested that a weakness in the cerebellum leads to articulation problems, and articulation expertise assists the process of becoming phonemically aware; then deficits here may translate into deficits on tasks that require precise phonological coding, such as reading. For example, patients with bilateral cerebellar degeneration are unable to discriminate between speech contrasts that involve purely temporal cues (Ackermann, H, Graeber, S, Hertrich, I, & Daum, I. (1997). Categorical speech perception in cerebellar disorders. Brain & Language, 60, 323-331).

For example, words such as "BIDDEN" and BITTEN" can solely be distinguished on the basis of a temporal cue, the period of silence at the time of occlusion. A recent functional imaging study has found that such sounds produce increased activation in only the cerebellum and inferior left frontal gyrus compared to speech perception conditions in which similar words contrast required the analysis of spectral cues (Mathiak, K. et al. (in press). fMRI of Cerebellar Speech Perception. Journal of Cognitive Nueroscience). Therefore, even speech perception considered to be a specialized task appears to engage a population of spatially distributed processors. Presumably, these processors are invoked when their specialized computations, such as timing, are required.

It follows that if skilled reading/writing requires sub-skills (such as word decoding) to become automatic, then the literacy abilities of the dyslexic subject will be further hindered. Concrete and direct evidence of cerebellar involvement is now available as a result of a study of motor learning using PET-scan (Nicolson, R. I., Fawcett, A. J., Berry, E. L. and Dean, P. 1997 Dyslexia: direct evidence of cerebellar impairment. Poster at Orton Dyslexia Society International Conference, Minneapolis, Minn., November). This study shows severe reductions in the levels of activation of the cerebellum in dyslexic adults in comparison with controls.

So far, we have discussed developmental dyslexia as a plausible neurological disorder originating at the biological level, whilst strongly emphasizing the magnocellular and cerebellum structures and their intimate correlation in the causation of the syndrome. However, impaired sensory processing of information has a detrimental effect among most learning disabilities. It is specifically detrimental to the next level of causation in developmental dyslexia, namely, in sensory perception.

We specifically herein refer to the ability of dyslexic subjects to integrate different streams of sensorial information into a single self-organized spatial-temporal percept in order to namely accomplish visual perception to recognize letters and guide motor behavior in order to principally accomplish reading, but also various imminent bio-motoric (e.g., visuomotor) performances in reachable space. Before continuing any further with the discussion on perception, we must generally define perception. "Perception is an act that encompasses both conscious and unconscious effects of sensory stimulation on behavior". Such a broad definition about perception derives from the need of including into a single framework the perceptual activities of both visual pathways, that of the ventral stream with that of the dorsal stream.

Low-level visual processing disorder in transient channels (reduced sensitivity in the magnocellular system) is likely to affect visual tasks such as the perception of brightness discrimination, motion, depth, and in many visual integration tasks (Lovegrove, W. J., Bowling, A., Badcock, D., & Blackwood, M. (1980). Specific reading disability: differences in contrast sensitivity as a function of spatial frequency. Science, 210, 439-440). Furthermore, a disorder in transient channels is likely to affect the localization of objects in visual space (e.g., the direction of visual attention), (Lennie, P. (1993). Roles of M and P pathways. In R. Shapley, D. Man-kit Lam, Contrast sensitivity, proceedings of the retina research foundation symposia, Vol.5. The MIT Press, Cambridge (Massachusetts), 201-213; Steinman, B. A., Steinman, S. B., & Garzia, R. P. (1996). Reading with an M neurone: how defective magnocellular pathway interferes with normal reading. In R. Garzia, Vision and reading. New York: GB Putnam's Sons), the control of eye movement (Eden, G. F., Stein, J. F., Wood, H. M., & Wood, F. B. (1994). Differences in eye movements and reading problems in dyslexia and normal children. Vision Research, 34, 1345-1358) and various kinds of visuomotor reaching actions. Transient channels are considered to have a temporal precedence in order to accomplish an initial global analysis of the visual scene.

Moreover, experimental findings have provided clear evidence for a high threshold for the perception of coherent motion, or alternatively, there was a significant reduction in sensitivity to coherent motion discrimination in dyslexic subjects (Cornelissen, P., Richardson, A., Mason, A., Fowler, S., & Stein, J. (1995). Contrast sensitivity and coherent motion detection measured at photopic luminance levels in dyslexics and controls. Vision Research, 35, 1483-1494). It has also been reported that dyslexic subjects have longer durations of visible persistence. This means that a longer duration of visible persistence in dyslexics may serve to lock visual stimuli in place over a longer time period and signal their immobility to the movement system. One consequence of this is a reduction in temporal resolution (Slaghuis, W. L., Twell, A. J., & Kingston, K. R. (1996). Visual and language processing disorders are concurrent in dyslexia and continue into adulthood. Cortex, 32, 413-438).

Lovegrove (Lovegrove W. (1993). Do dyslexics have a visual deficit? In: Wright S. and Groner R. Facets of dyslexia and its remediation. (pp. 33-49) Amsterdam: North-Holland) has argued that both phonological processing and deficits in visual processing in dyslexia may reflect a common underlying process. He suggests that the evidence for differences in processing rapidly presented stimuli in more than one sensory modality (Tallal, P. (1985). Auditory temporal perception, phonics and reading disabilities in children. Brain and Language, 9, 182-198), and the relationship between rapid visual processing that engages the transient system and phonological coding, may reflect a general sensory timing problem in dyslexia (Lovegrove W. and Williams M. (1993). Visual temporal processing deficits in specific learning disability. In: Willows D., Kruk R. and Corcos E. (Eds.) Visual processes in reading and reading disabilities. (pp. 311-330) Hillsdale, N.J.: Lawrence Erlbaum).

Still, how may impairment in sensorial perception in general and visual perception in particular distort or affect the self-organization of spatial-temporal percepts in the mind of a dyslexic subject? Or, differently phrased, dyslexia could well fit in an ontological parallel causation model, including (a) a net information-processing deficit, due to genetically biological factors; and also (b) an early visual perceptual deficit in attaining a global and direct extraction of sensorial information originating from the environment (as manifested in the non-conscious and automatic ability a subject possesses in collapsing sensorial information into a congruent spatial-temporal perceptual setting).

Indeed, developmental evidence claims for a multiple and parallel causation approach to dyslexia. Therefore, neurological deficits in the cerebellum or in the magnocellular system will sometimes hinder early sensory perception in general and early visual perception in particular by depriving it from the implicit and pre-attentive mechanisms that account for directly extracting sensorial information from the stimuli array. Thus, early perceptual deficits should be considered a "second core deficit" in developmental dyslexia.

Aside from the already discussed primary core deficit at the biological level in dyslexia, we should now turn our attention to an early perceptual deficit centered on a abnormal magnocellular development, principally affecting the dorsal visual pathway, but also the ventral functional visual system, as a parallel and plausible second core deficit responsible for causing dyslexia. Such second core deficit makes us to closely consider the nature of early perceptual processes in general, and the role of ecological perceptual processes in particular.

Furthermore, if perception is considered to be a modular and integrative approach, a deficit in early sensorial perception mainly caused by the visual dorsal pathway parallels well with the ecological view on perception (Gibson, J. J. (1966). The senses considered as perceptual systems. Boston: Houghton Mifflin; Gibson, J. J. (1979). The ecological approach to visual perception. Boston: Houghton Mifflin; Gibson, E. J. (1969). Principles of perceptual learning and development. New York: Appleton-Century-Crofts; Gibson, E. J. (1984). Perceptual development from an ecological approach. In M. Lamb, A. Brown, & B. Rogoff (Ed.), Advances in developmental psychology (Vol.3, pp 243-285). Hillsdale, N.J.: Erlbaum; Johansson, G. (1970). On theories for visual space perception: A letter to Gibson. Scandinavian Journal of Psychology, 11(2), 67-74; Shepard, R. N. (1984). Ecological constrains on internal representation: Resonant kinematics of perceiving, imagining, thinking, and dreaming. Psychological Review, 91(4), 417-447). The ecological account has shed new light on early sensorial perception by strongly linking an early perceptual deficit with the biological hypothesis, which centers on magnocellular and cerebellar deficits for being the causation of developmental dyslexia. The ecological account posits the assumption that visual direct extractions of information from the ambient, results in a particular perceptual construct that contains by far more information than the summations of its optical arrays parts if added together. Accordingly, perception once assembled cannot be broken into single percepts, that is, a direct and active perceptual act cannot be reduced to any of its spatiotemporal isolated informative components.

Additionally, the ecological account acknowledges that early sensorial perception possesses a kind of special "qualia" where information is being picked up or extracted mainly by the dorsal visual stream (but also by the ventral stream via considerable magnocellular input) from ambient energy in order of being self-organized into a perceptual wholeness in a non-cognitive, pre-attentive (automatic) and implicit manner by the perceiver. The ecological theory basically views a perceiving organism as not only awash in energy, but also in information. Importantly, the organism is considered to be actively involved in the pursuit of information. According to Gibson, these interactions are of a universal character, resulting in a detailed correspondence between patterns in ambient energy and the structure of the environment. Thus, the perceiver and the environment have a reciprocal relationship, namely, they form a whole. The ecological approach argues that the information in the ambient suffices and is not equivocal and thus, no "mental processes" are needed to enable the extraction of meaningful information. The ecological approach views perception as a single-stage process, that is direct and immediate.

Furthermore, the focus is on the perceiving organism as an integrated system for information extraction rather than on activity at single receptors (in the nervous system) or even simple summing of such activity in multiple locations. Receptive elements and individual nerve fibers are parts of larger devices whose circuitry is set up to extract useful information. In short, the organism's sensorimotor behavior allows it to actively extract information, and this information in turn guides ongoing behavior (Gibson, J. J. (1966). The senses considered as perceptual systems. Boston: Houghton Mifflin). In this view, early perceptual development begins in meaningful contact with the world.

Gibson strongly emphasized that early perceptual processes are geared to detect and extract structure in ambient energy rather than properties of the energy itself (such as intensity or wavelength of light), and that early perceptual processes effortlessly, automatically and actively extract higher-order information from incoming stimulation. Gibson also explained higher-order information as structure already contained in the sensorial stimuli array of information, that is, relational information self-emerging from distinctive features and patterns concerning relationships among parts in the array (and not to bits and isolated pieces of information).

Moreover, perceptual extraction of information at this early developmental phase has come to exploit enduring regularities in the physical world, meaning that as a sign of economy in information extraction, the organism only extracts invariants (from the stimulation array) in the search for relations that remain constant over change. As Gibson further explained, information extends over time and space as people and objects move. That is, stimulation is not static and frozen in space and time. Thus, the best information available to human perceivers is extended in time, and perceptual systems are equipped to utilize such information. Gibson, like Johansson (Johansson, G. (1950) Configurations in event perception. Uppsala, Sweden: Almkvist and Wiksell), calls attention to the fact that perception consists of perceiving events, that is, perceiving changes over time and space in the optic array.

Stimulation carries many levels of information. Looking with a single eye through a peephole, a three-dimensional scene may be undistinguishable from a photograph or photorealistic painting. However, when the observer views a scene or photograph while moving (e.g. walking), the optical transformations across time differ drastically. Motion affords potentially powerful information about the 3-dimensional shapes of moving objects as well as about an observer's own movements within the environment populated by those objects. In particular, the movements of objects within the environment create spatiotemporal changes in the light distribution on the retina of a stationary observer. Likewise, an observer's own movement through a stationary environment changes his or her retinal image. Such spatiotemporal changes, whatever their origin, are termed "optic flow", and they constitute significant sources for visual information. For example, optic flow provides information about speed, direction and path of an observer's movements. Optic flow can also provide information about the three-dimensional structure of the environment (Koenderink, J. J. (1986) Optic flow. Vision Research, 26, 161-180).

Assuming the environment is at rest, the pattern of optical changes (optical flow) furnishes unequivocal information about the three-dimensional spatial relationships in the scene, with the relations between optical transformations and the real scene specified by the laws of projective geometry. It is well established that this kinematic information (optical flow) given by the observer or the object motion is the fundamental spatiotemporal information being extracted by the organism in early visual sensorial perception.

In experimental settings, motion is a potent specifier of shape. This potency was demonstrated in studies by D. Regan (Regan, D. (1989) Orientation discrimination for objects defined by relative motion and objects defined by luminance contrast, 29, 1389-1400) who created displays in which alphanumeric characters were defined by clusters of dots moving in different directions. People readily see a figure defined by those common dot motion vectors, and they judge with excellent accuracy the shape of that figure. This is called "kinetic form perception" and this ability is conserved in the face of substantial amounts of random motion noise.

Furthermore, the visual perception of biological motion provides another compelling example of vision's ability to extract object information from motion. Because normal biological motion involves deformation of the body, biological motion is classified as 'non-rigid motion.' Perception of a biological organism that is engaged in an activity requires global integration of motion signals over space and time. As a result, the perception of such animation sequences is literally the creation of motion information (in the same sense that perception of an object in a random-point stereogram is the creation of binocular disparity information).

Optic flow also translates to what is denominated 'kinetic depth', which consists of motion information conveyed by three dimensional spatial structures of surfaces. A single view of a stationary two-dimensional object affords little unambiguous depth information. But when the object is set into motion, its projection can produce a clear impression of the object's depth and spatial structure. Wallach and O'Connell (Wallach, H., & O'Connell, D. N. (1953) The kinetic depth effect. Journal of experimental Psychology, 45, 205-217) provided an early report of this phenomenon, which they dubbed "the kinetic depth effect." Today, the accepted term to describe the phenomena is "structure-from-motion", which encompasses not only the emergence of depth from motion, but also the generation of surfaces and other object-related properties.

We have so far presented arguments for a biological causation to developmental dyslexia in deficits originating from the magnocellular and cerebellar systems in the brain. We have also provided evidence that call for a parallel deficit in early self-organization of visual sensory perception in dyslexic subjects. Both levels of causation hint towards a neurophysiological disorder that manifests itself in at least: (a) a lack in motor control; (b) a lack in guiding motor behavior; and/or (c) poor early visual sensory perception due to a lack in relational information extraction from the stimuli array. Yet the latest conceptual extensions of both accounts call for a complementary view that fuses perception and action into a single domain.

In Gibson own words, "We must perceive in order to move, but we must also move in order to perceive." Perception and action are so interdependent that it is hard to imagine the evolution of either without the other already in place. Furthermore, the ecology of any organism is conditioned by its capacities for action, just as it is conditioned by the information available for perception.

Human and animal behavior might in general be described in terms of perception-action loops (Gibson, J. J. (1966) The senses considered as perceptual systems. Boston: Houghton Mifflin). Adjustment of active perceptual systems facilitates the extraction of information, which is used in guiding action and additional seeking of information (Gibson, J. J. (1979). The ecological approach to visual perception. Boston: Houghton Mifflin; Mace, W. M. (1974). Ecologically stimulating cognitive psychology: Gibsonian perspectives. In W. B. Weimer & D. S. Palermo (Eds.), Cognition and the symbolic process (pp. 137-164). Hillsdale, N J: Erlbaum; Turvey, M. T., Shaw, R. E., Reed, E. S., & Mace, W. M. (1981). Ecological laws of perceiving and acting: In reply to Fodor and Pylyshyn. Cognition, 9, 237-304).

Within the context of perception-action loops and their relevant connection to a magnocellular deficit particularly in the dorsal stream of visual perception in developmental dyslexia, a recent revision by Milner and Goodale (Milner, A. D., & Goodale, M. A. (1995) The visual brain in action. Oxford, England UK: Oxford University Press) of the functions served by the two separate visual streams is now available. The dorsal and ventral streams' pathways for processing visual information are now reconsidered in terms of "action" and "perception."

While the visual ventral stream functions have in principle remained almost the same from that of Ungerleider and Mishkin (Ungeleider, L. G., & Mishkin, M. (1982) Two cortical visual systems. In D. J. Ingle, M. A. Goodale, & R. J. W. Mansfield (Eds.), Analysis of visual behaviour (pp. 549-586). Cambridge, Mass.: MIT Press), their main innovation is the function they attribute to the dorsal stream. Rather than mapping the location of objects, the visual dorsal stream is concerned with the visual control and guidance of motor behavior. According to Milner and Goodale, the major difference between the two streams doesn't rest upon the way both pathways process visual information, but in the kind of transformation they perform with the available visual information. On one hand, the ventral stream transforms visual information into an "exocentric" (allocentric) mapping of space, allowing the perception of the objects as it relates to the visual world. On the other hand, the dorsal stream transforms the available visual information into an "egocentric" mapping of space, allowing the actor to grasp or otherwise bodily manipulate the object.

Milner and Goodale (Milner, A. D., & Goodale, M. A. (1995) The visual brain in action. Oxford, England UK: Oxford University Press) have argued that the representation and conscious awareness of external objects and contextual information is a consequence of processing in the ventral stream. The control of our actions, in contrast, is said to be due to the dorsal stream, which operates implicitly without our conscious awareness.

Thus, it now becomes clearer why the influence of illusions, which often arise from misinterpreting the context, can be considered critical for the specialization found in the visual neural pathways. Many studies have compared information processing in the dorsal and ventral pathway by comparing the influence of illusions in perceptual and motor tasks. In perceptual tasks, which are assumed to be processed by the ventral system, illusions obviously show an influence on the measured variables (e.g. size, position illusions, etc.). In motor tasks, which are assumed to be processed by the dorsal system, often no influence is found. Thus, we might be able to fool the eye, but not the fingers!

Extraction of spatiotemporal relational information from motion perception emerges from a synergic cooperation between exogenous influences (represented by stimulus attribute) and endogenous influences (including expectation, attention, memory, and learning). Hence, it is critically important to understand what role endogenous influences play in the circular causation of action-perception loops. Central to the visual motion perception issue, is the following question: how can the cognitive machinery benefit from information, which has been automatically picked up by early visual sensory perception, while providing for normal or even excelled cognitive processing?

The scientific literature provides a number of clues as to how direct information extraction about motion stimuli gets picked up by early visual perception and subsequently gets manipulated into by cognitive resources. Attention, for example, promotes preferential processing of stimuli or of stimuli characteristics that are relevant to a particular task, and inhibit processing of task-irrelevant stimuli characteristics (Raymond, J. E. 2000 Attentional modulation of visual motion perception. Trends in Cognitive Science, 4, 42-50). Pioneering neurophysiological experiments in the parietal lobe in primates have revealed that neurons, at earlier stages in the visual pathway, respond in a stereotyped manner to the pattern of light falling on the retina, irrespective of the behavioral significance of the stimuli. However, Wurtz's (Wurtz R, Goldberg M, Robinson D. 1982 Brain mechanisms of visual attention. Sci Amer 246:124-135) clinical work suggested that attention acts as a "regulator" of the visual information flow from "low" to "high" levels of the cerebral cortex, ensuring that only the most relevant information reaches the highest processing levels of the system. In short, the most valuable processing stages are allocated into action only for the most significant stimuli appearing in the visual field. Accordingly, attention modulates the behavioral impact of any moving stimulus in accordance with the observer's task and goals.

Furthermore, attention has enormous influence in tasks such as tracking multiple objects due to the brain exploiting neural circuits which shift attention from one location in space to another. In an fMRI study conducted by Culham et al. (Culham, J. C., Brandt, S. A., Cavanagh, P., Kanwisher, N. G., Dale, A. M., & Tootell, R. B. (1998) Cortical fMRI activation produced by attentive tracking of moving targets. Journal of Neurophysiology, 80, 2657-2670), attentive tracking of multiple, independently moving objects is mediated by a network of areas that includes parietal and frontal regions known to be responsible for shifts of attention between locations for eye movements, area MT and related regions. These are central regions for processing motion information.

Moreover, the selectivity or preferential processing of stimuli attributes by attention mechanisms is significantly affected by uncertainty concerning direction of motion, which impairs detection performance. Ambiguity about direction of motion should basically be understood as if the observer possesses prior knowledge about stimulus direction. Thus, uncertainty diminishes the detectability of motion, as indexed by elevated thresholds or lengthened reaction times.

Presumably, prior information about the direction of motion temporarily boots the signals of MT neurons that are particularly responsive to that direction of motion (Treue, S., & Maunsell, J. H. R. (1999) Effects of attention on the processing of motion in macaque middle temporal and medial superior temporal visual cortical areas. Journal of Neuroscience, 19, 7591-7602; Treuce, S., & Trujillo, J. C. (1999) Featured-based attention influences motion processing gain in macaque visual cortex. Nature, 339, 575-579). Still on the direction of motion, Pasternak has studied the visual area MT's role in remembering the direction of visual motion (Bisley, J. W., & Pasternak, T. (2000) The multiple roles of visual cortical areas MT/MST in remembering the direction of visual motion. Cerebral Cortex, 10, 1053-1065 and Bisley, J. W., Zaksas, D., & Pasternak, T. (2001) Microstimulation of cortical area MT affects performance on a visual working memory task. Journal of Neurophysiology, 85, 187-196) in monkeys. Pasternak's results point toward the notion that MT is involved in short-term retention and/or retrieval of information regarding the direction of visual motion. In most general terms, visual memory is an important guide for behavior. Memory of visual past events enables us to prepare appropriate responses toward situations where our actions are executed in a timely fashion.

In particular, visual movement preparation of suitable behavior requires some degree of discrimination that some motion, which is being experienced now, has in fact been seen before. Indeed, Chum and Jiang (Chun, M. M., & Jiang, Y. (1999) Top-down attentional guidance based on implicit learning of visual covariation. Psychological Science, 10, 360-365) have shown that repeated exposure to particular complex movement sequences remains at the implicit level, that is, motion sequence is being registered in some kind of implicit memory storage. This finding supports the notion that subjects can pick up and somehow encode kinematical invariance from stimuli and that they can do so without explicitly recognizing those repeating features.

Another cognitive resource, that is worth mentioning in order to have accomplished a brief survey on cognitive functions which affect visual perception, is expectations. We do not see the world the way it actually is. Instead, our ordinary perception is distorted in numerous ways. People's reports of size, shape, distance, color space and other percepts are highly influenced by context and expectations. Expectations partially determine ordinary perception and in cognitive science are considered to be a top-bottom process, which is highly dependent on context. In short, expectations are a by-product of our past experiences and act as an endogenous filter on ordinary perceptual information reaching us via our senses.

To summarize the herein presented related art, we have provided scientific evidence to substantiate a parallel biological visual perceptual multiple causation hypothesis for the neurological disorder called "developmental dyslexia."

We have also reviewed plausible biological systems that are thought to negatively contribute to the syndrome, such as the cerebellum and the visual magnocellular system. Additionally, we have identified a parallel mechanism responsible for: (a) visual information processing deficits; and (b) early global sensory perception deficits. In general, we have carefully outlined scientific evidence in favor of a developmental dyslexia approach along cerebellar deficits translating into a lack of: (a) motor control; (b) motor guided behavior; (c) timing for effective motor control; and (d) cognitive prediction as instrumented in feedforward motor plans for the self-organization of real time (imminent) movements. In particular, cerebellar deficits hinder motor control of key muscles in the organism that impair both oculomotor control (fixation) of the eyes and fine motor coordination between hand-eye movements, which in turn impair handwriting, handgrip and aperture as well.

We have also briefly discussed how endogenous top-bottom processes influence visual perception as manifested in our verbal reporting about attributes of space and time. Such perceptual distortions have lately emerged in the psychophysical laboratory as exposing an existing underlying dichotomy among perceptual processes in general. On the one hand, there are percepts that guide our actions and consequently our verbal reports about those actions in relation to the world at large (allocentric space). On the other hand, there are percepts that guide our most imminent motor actions only in relation to our egocentric space. Most importantly, it is under the light of the later kind of perceptual processes, that we have extensively shown that motor deficits should be considered as a contra fit of an early visual sensorial perceptual deficit, namely, that action and perception are inseparable.

Finally, we have strongly emphasized that both alternative hypotheses underlying developmental dyslexia, that of a magnocellular deficit and that of a cerebellar deficit, strongly converge together into a similar and highly interconnected causal biological background. This interconnected causal biological background demonstrates that dyslexics have lower sensitivity for transient stimuli in the visual system. In other words, dyslexic children show a lower sensitivity to 'temporal processing' in general, and they indeed struggle perceptually, with the extraction of information necessary for the perceptual internalization of the arrow of time in their every day life.

2. Theoretical Overview

In an embodiment, the apparatus and method of the present invention are utilized to produce and generate an optical field, which transforms into a perceptual simple optical flow field once it reaches the eye of the subject. Such perceptual simple optical flow field conveys kinematical relational information from an optical stimuli array(s), for the direct and implicit extraction of the information, via a subject's early (visual) perception. Preferably, facilitating an implicit and direct extraction of relational information from early motion perception (a simple optical flow field) from a visual stimuli array(s), by constructing a visual intrinsic variable environment specifically encompassing various dimensions of pre-attentive features, the apparatus comprising a physiological mechanical activity sensor module, a optical events stimuli module, a optical field stimuli output module and a game/entertainment program module.

The present invention also provides a method for time correlating and fluctuating early perceptual kinematical attributes of a produced and generated simple optical flow field, with physiological mechanical activity. In embodiments of the invention, as a result of such time correlation and fluctuations, the subject will experienced an improvement in a condition. One goal of the invention is to improve motor fluency in order to ameliorate symptoms of dyslexia in reading.

For illustrative purposes, the invention is described herein as correlating perceptual kinematical attributes of a produced and generated simple optical flow field during an early visual perceptual phase with physiological mechanical activity in a target organ and/or in a physiological mechanical system in a time varying fashion. More generally, the invention is directed to correlating perceptual kinematical attributes produced and generated by a simple optical flow field with a physiological mechanical activity in some varying fashion, where time is an example of a variable that may be varied. It should be noted that the invention is not limited to this example embodiment involving time only, but may also involve some other kind of correlations.

The apparatus and methods of the present invention utilize a multidimensional approach to, generally, facilitate ordinary visual perception, and more specifically, to ameliorate deficits in visual perception in general and symptoms in developmental dyslexia in particular, not taught or suggested prior the invention, namely:

(a) Producing and generating an intrinsic and variable visual dynamic environment such that the kinematical freedom of the generated and comprised velocity vectors will be constrained to follow only kinematical trajectories in a single dimension or plane (e.g., simple motion translation—some forms of planar motion. Hence, the generated perceptual kinematical attributes will be restricted such that to satisfy a perceptual simple optical flow field. Kinematical trajectories conveying a complex optical flow field to the subject such as: radial (expansion/contraction), circular, radial-rotational (spiral motion), radial-circular and some forms of planar motions generating possible complex flow fields are not allowed.

(b) Reinforcing the potential for implicit awareness in a subject, for mapping and transforming information about multiple egocentric sources, for successfully guiding imminent motor behavior in reachable space, and also, facilitating a normal discriminatory development (verbal, cognitive and sensory motor) of allocentric space (the environment at large) via visual ordinary perception;

(c) Facilitating the pickup of relational information implicitly and effortlessly from perceptual kinematical attributes produced and generated by a simple optic flow field, such that to enable temporal processing discrimination of an explicit representation of event timing (among sequential movements—time discreetness). Thus, the subject becoming capable of predicting time durations in sequential movements e.g. finger tapping, etc.; and (d) Maximizes the orienting of covert attention towards an intrinsic variable visual dynamic environment by:
  (i) Populating and embedding multiple pre-attentive dimensions into one intrinsic and variable dynamic visual scene, thus reducing attention involvement to distractive features;
  (ii) Optimizing early visual perceptual resources to enable the fast pickup of salient (novel) stimulus;
  (iii) Optimizing early visual perceptual resources such that to enable a more efficacious processing of information from any visual scene via ordinary perception.
  (iv) Quasi-randomization of the spatial-temporal distribution of perceptual kinematical attributes in the intrinsic variable visual dynamic environment such that minimizing attentional deployment towards the visual scene as to strongly restrict associative learning from the visual scene by the subject.

A controlled, experimental clinical study was conducted by the University of Nottingham between November 2001 and March 2002 that involved a prototype of the present invention as it relates to ameliorating deficits in visual perception, in general, and deficits in visual perception in developmental dyslexia, in particular. Two documents were provided by the University of Nottingham in 2002 after completion of and as a result of this clinical study. These two documents entitled "Synopsis of the Nottingham Dyslexia Study" and "Nottingham Dyslexia Study for ALS: Report for Investors" are both incorporated herein by reference in their entities.

2.1. Definitions

This section provides definitions of terms used herein. Such definitions are provided in this section for the convenience of the reader, although it is noted that these terms are further described in other sections contained herein. Variations and/or extensions of the following definitions applicable to the present invention will be apparent to persons skilled in the relevant art(s) based at least on the teachings contained herein.

In the following, the definitions are discussed in the context of the present invention, such that the theoretical overview of the invention is continued in this section.

"Actions" refer herein to coordinated set of movements, which explicitly or implicitly convey a message to another perceiver. Preferably, actions are intentional and therefore should be considered to be a communicational act. In particular, perceived set of actions not only can be parceled but also can be express in language by a perceiver. Normal cognitive development principally depends on the subject's ability to delay or inhibit altogether, moment to moment actions (re-actions) over to changing selective attentional demands. Hence, the ordinary perceptual experience of allocentric space is compressible to a semantic report and therefore (mostly) conscious. Accordingly, action control and planning in allocentric space are to a degree distorted due to strong endogenous influences including expectations, short-term memory, attention, intention and learning.

"Allocentric space" often called absolute space perception, refers herein to spatial perception that gives detailed information about object features (e.g. size, form, color etc,) including the location of objects with respect to each other. Allocentric perception in contrast to egocentric perception activates different cerebral areas, such as the hippocampus (O'Keefe, J. and Nadel, L. 1978 The hippocampus as a cognitive map. Clarendon Press, Oxford; Muller, R. U. Bostock, E. M., Taube, J. S., and Kubie, J. L 1994 On the directional firing properties of hippocampal place cells. Journal of Neuroscience, 4: 7235-7251). In particular, executed actions towards an allocentric space are guided by the cells that encode the location of the perceiver in relation to the geometric properties of the enclosure and the cells that encode the movements of the body, particularly the head, when the perceiver moves in the environment (Taube, J. S., Muller, R. U., and Ranck, J. B. 1990 Head direction cells recorded from the postsubiculum in freely moving rats. Description and qualitative analysis. Journal of Neurosciences, 10: 420-435; Taube, J. S. 1995 Head direction cells recorded in the anterior thalamic nuclei in freely moving rats. Journal of Neuroscience, 15: 70-86). Accordingly, the visual ventral stream is responsible for the recognition of objects, position in absolute space, remembering spatial location and producing verbal reports about the results of its analysis.

"Cerebellum" is a large brain mass located behind the mesencephalon and above the pons, forming the roof of the IVth ventricle. It has a well-developed cortex of three layers in most vertebrates. In mammals, this cortex and its underlying tract system are extensively folded into folia, lobules and lobes together, known as the arbor vitae, because of its resemblance to the leaf form of those junipers. Buried deep in the axon mass of the tracts are several pairs of deep cerebellar nuclei. In humans, it accounts for (10) to (15) percent of brain weight, (40) percent of brain surface area and (50) percent of the brain's neurons. It is involved in the control of independent limb movements and especially in rapid, skilled movements. Injury to this area in general leads to motor or movements difficulties and in particular, resulting in slow and uncoordinated movements. Damage to the cerebellum can lead to: 1) loss of coordination of motor movement (asynergia), 2) the inability to judge distance and when to stop (dysmetria), 3) the inability to perform rapid alternating movements (adiadochokinesia), 4) movement tremors (intention tremor), 5) staggering, wide based walking (ataxia gait), 6) tendency towards falling, 7) weak muscles (hypotonia), 8) slurred speech (ataxic dysarthria) and 9) abnormal eye movements (nystagmus). Particularly, the cerebellum has traditionally been seen as a motor area. However, the cerebellum has recently emerged as a cerebral area also involved in cognitive processes, that is, this brain area is critically involved in the automatization of any skill, whether motor or cognitive. Preferably, it has been argued that the cerebellum is preferentially involved in controlling complex movements, multijoint movements and movements that require visuomotor coordination or learned automatic movements (Stein J F, Glickstein M (1992) The role of the cerebellum in the visual guidance of movement. Physiological reviews 72: 967-1018; Thach, W. T. Goodkin H. P. and Keating J. G. 1992 The cerebellum and the adaptive coordination of movement. Ann Rev Neurosci 15: 403-442), although one of the mayor functional roles of the cerebellum is the control of motor timing (Ivry, R B, Keele, S W & Diener, H C. 1988 Dissociation of the lateral and medial cerebellum in movement timing and movement execution. Experimental Brain Research, 73, 167-180). Robust findings have shown that the lateral cerebellum participates in temporal processing as well as in silent mental counting, which requires chronometric counting (Decety, J., Sjoholm, H., Ryding, E., Stenberg, G., & Ingvar, D. (1990). The cerebellum participates in cognitive activity: Tomographic measurements of regional cerebral blood flow. Brain Research, 535, 313-317; Ryding, E., Decety, J., Sjoholm, H., Stenberg, G. & Ingvar, D. H. (1993). Motor imagery activates the cerebellum regionally. A SPECT rCBF study with 99 mTc-HMPAO. Cognitive Brain Research, 1, 94-99). In particular, recent neuroimaging studies, have provided evidence for activation of the anterior lobe of the cerebellum of both sides, when subjects estimated time differences by comparing a test time with a standard interval (Jueptner, M., Rijntjes, M., Weiller, C., Faiss, J. H., and et al., 1995 Localization of a cerebellar timing process using PET, Neurology 45 (8), 1540-1545), and when subjects reproduced rhythms of increasing complexity (Penhune, V. B., Zatorre, R. J., & Evans, A. E. (1998). Cerebellar contributions to motor timing: A PET study of auditory and visual rhythm reproduction. Journal of Cognitive Neuroscience, 10(6): 752-765), indicating the involvement of the cerebellum in motor timing and perceptual timing, respectively. Within the context of how a cerebellar impairment will affect learning difficulties, it is suggested that cerebellar deficits translates into articulation fluency problems and then one indirect effect is that it takes up more conscious resources, leaving fewer resources to process the ensuing sensory feedback. Moreover, reduced articulation speed leads to a less effective "working memory' as reflected in the phonological loop, resulting in difficulties in language acquisition. Furthermore, poor articulatory representation might lead to impair sensitivity to onset, rhyme and the phonemic structure of language.

"Dorsal" in anatomy referring to of, on, or relating to the upper side or back (Oxford Dictionary, 1999)

"Dyslexia" refers to a neuro-developmental disorder characterized by deficits at the biological, cognitive and behavioral levels. Dyslexia is associated with a difficulty in learning, on one or amore of reading, spelling and written language which may be accompanied by difficulty in number work, short-term memory, sequencing, auditory and/or visual perception and motor skills. It is particularly related to mastering and using written language—alphabetic, numeric and musical notation. In addition oral language is often affected to some degree. Dyslexia directly afflicts around (5) percent of the general population. However, its comorbidity with other learning difficulties afflicts up to (20) percent of the general population.

"ECG" is a display of electrocardiographic events. See FIG. (23). An ECG monitor can provide either a visual (e.g., digital) or a printed display.

"Egocentric space" refers herein to a sensorimotor perception of space, (centered) with respect to the perceiver's body. The brain must figure out the position of the object with respect to the body, so that it is unaffected by an eye, body and/or hand movement. In particular cell recordings during space perception shows neuronal activity in several cortical and subcortical areas such as the parietal lobe, the prefrontal cortex and the superior colliculus. These spatially selective cells respond to visual events coded according to retinal, head or body centered coordinates (Andersen, R. A., Snyder, L. H., LI, C. S., and Stricanne, B. 1993 Coordinate transformations in the representations of spatial information. Current Opinion in Neurobiology, 3: 171-176; Andersen, R. A. 1995 Coordinate transformations and motor planning in the posterior parietal cortex. In M. S. Gazzaniga (Ed.), The Cognitive Neurosciences. Cambridge, Mass.: The MIT Press, pp 519-548; Galletti, C., Padovani, A., Pantano, P., and Pizzamiglio, L. 1993 Unilateral neglect restricted to visual imagery. Nature, 364: 235-237). Accordingly, the visual dorsal stream is specialized for egocentric space perception and for the on-line visual control of movement, namely perceptually guiding imminent ballistic movement in the perceiver's reachable space.

"Event timing" refers herein to performance on a range of movements that require precise timing, including the production of skilled movements and perceptual movement duration discrimination. Preferably, event timing is a mental operation a form of representation, in which the temporal goals (information) are explicitly represented. Psychologically, such representation specifies when particular events should occur or have occurred. In particular, event timing refers to sequential repetitive movements that are either performed in a continuous or segmented manner. It is also implied that a mental representation judging the duration of an empty interval, requires that the interval be explicitly represented and eventually, compared with a representation of an internalized standard interval. It is further hypothesize that the cerebellum is the neural platform specialized for providing this explicit form of temporal duration representation.

"Heart cycle" refers to the ejection of blood into the arterial tree from the left ventricle of the heart. In the systolic or initial phase of the heart cycle the heart contraction takes place and arterial blood is ejected form the left ventricle into the aorta, by which the aorta and its arterial branches distend to accommodate to an increase in the demand of blood flow. The diastolic phase follows to the systolic phase to complete the heart cycle. More, precisely, it occurs when the ventricle walls expand to receive back approximately the same amount of blood emptied during the previous mechanical systole.

"Inferior-temporal cortex" (ITC) refers to a cerebral area generally involved in visual recognition. In particular, facial and color recognition. It contains cells, which respond preferentially to complex stimulus features (shapes) of a specific nature regardless of size or position on the retina. This division of the visual system tells us to identify what we see namely recognizing separate objects, faces and people. ITC neurophysiological stream of information begins with parvocellurar-interblob system of V1 sending information to V2 and then to V4. V4 preferably has a topographic map of the retina, but deals with form and color, primarily. V4 sends information to ITC, which is involved in the recognition of form. In the ITC, some cells are specifically activated by faces (some cells respond best to a frontal view of the face, others to a side view) while some other cells are activated by phase and hand expressions.

"Intrinsically varying physiological activity" refers broadly to any cyclical physiological event that is under autonomous and automatic control and that is characterized by intrinsic variability. Indeed, one characteristic of physiological activity so to exhibit intrinsic temporal variability, i.e., a varying frequency of occurrence over time. In general, physiological activity is regulated by the dynamic balance between sympathetic and parasympathetic neurophysiological control mechanisms. Still more preferably, the term physiological activity refers herein to at least one of the breathing cycle, heart cycle, blood pressure wave, pulse wave, hormonal cycle and brain wave activity. Although the invention is illustrated herein as using physiological mechanical activity, the invention is not limited to this.

A "Cycle" of a physiological activity is the completion of one occurrence of the physiological activity. For example, a cycle of a heart is one heart contraction and expansion (or heart beat), i.e., mechanical systole and mechanical diastole. Occurrence of a respiratory cycle is one inspiration and (one) expiration. A cycle of a brain wave is one wave (e.g., alpha, beta, etc.) or any other periodical process in the electrocortical activity.

"Lateral geniculate nucleus" LGN—The major input to the visual cortex is from the LGN. Axons from retinal ganglion cells continue beyond the optic chiasm as the optic tract, and they form a synaptic connection in the thalamus, in a subcortical structure called LGN. The LGN is composed of six layers, the fibers from the contralateral eye project to layers 1, 4 and 6, and those form the ipsolateral eye to layers 2,3 and 5. Cell bodies in layers 1 and 2 are larger than cell bodies in layers 3-6; the former are called magnocellular layers and the latter parvocellular layers. Magnocellular cell receptive fields are 2-3 times larger than parvocellular cell receptive fields, and magnocellular cells have better sensitivity and respond well to moving stimuli, whereas parvocellular cells have better acuity, resolution and respond well to color stimuli. Axons from LGN cells project to the visual cortex, which is situated in the back of the brain. In short, LGN projects to the primary visual cortex (striate cortex), also called V1. Preferably, all cells project to layer IV of V1; however, those from the magnocellular layers project to higher subdivisions in layers IV in V1. In conclusion, the large and small cells that were intermingled in the optic tract project to separate sites in the LGN. The LGN possible functions should be considered to be: a) enhances information about contrast; b) organizes information (e.g., eye of origin, color, motion, form); c) modulates levels of processing with arousal (via the reticular activating system); receives feedback from higher areas (V1).

"Middle temporal area" (MT)/V5 refers herein to a cortical area in the dorsal visual pathway, which deals with visual-motion transformations, namely, motion perception. Area MT is characterized by strong motion-directionally sensitive neurons with large receptive fields organized into columns. Along a column, axons respond to motion in a preferred direction. However, preferred direction varies systematically along columns. In general implicated in the analysis of movement, and stereoscopic depth and particularly sensitive to small moving objects or the moving edge of large objects. Receives input from layer 4*b* in V1 and thick stripes in V2. Area MT projects to MTS. play a direct role in motion perception, particularly as it applies to the perception of surfaces in motion. It has been shown that a population of MT neurons integrates the orthogonal components of motion from various edges in an object and codes the true directions of the objects motion. More so, a fascinating perceptual attribute of the motion system is the ability to represent the 3-D shape of objects purely from motion signals. It has been shown that MT neurons activity indicates that they can segregate order from depth of surfaces in structure-from-motion displays. Additionally, MT neurons are strongly suppressed in responding to a motion stimulus in their preferred direction if a second motion of a different direction is also present (Snowden, R. J., Treue, S., Erickson, R. G., & Andersen, R. A. 1991 The response of area MT an V1 neurons to transparent motion. The Journal of Neuroscience, 11, 2768-2785; Qian, N., Andersen, R. A. & Adelson, E. H. 1994 Transparent motion perception as detection of unbalanced motion signals. I. Psychophysics. The Journal of Neuroscience, 14, 7357-7366). Such neuronal suppression plays a significant role in removing and thus, reducing noise from movement perception. Projects along with MTS to the dorsolateral pontine nuclei in the brain stem.

"Medial superior temporal dorsal area" (MSTd) refers herein to a cortical area in the dorsal visual pathway that processes complex visual motion patterns. Cells in this area have larger receptive fields that respond selectively to expansion, contraction, planar translation, rotation and spiral motion stimuli that are generated during observer motion (Saito, H. et al. 1986 Integration of direction motion signals of image motion in the superior temporal sulcus of the macaque monkey J. Neurosci. 6, 145-157; Duffy, C. J., and Wurtz, R. H. 1991a. Sensitivity of MST neurons to optic flow stimuli. I. A continuum of response selectivity to large-field stimuli. J. Neurophysiol. 65, 1329-1345; Graziano, M. S. A., Andersen, R. A., and Snowden, R. J. 1994 Tunning of MST neurons to spiral motions. J. Neurosci. 14, 54-67). This kind of stimulation is called optic flow, and it can be used to observer navigation thorough the world (Gibson, J. J. 1950. The perception of a visual world. New York: Appleton-Century-Crofts) namely, self-motion. MST cells having larger receptive fields can see even larger motion patterns composed of many local motions detected by the MT cells. Such a global motion pattern may reflect the global optic flow of the scene and can be represented by an array of arrows each representing the velocity, both direction and speed, of a local motion. If we are moving forward while walking or driving, and not making eyes movements, then the optical flow field has a radial expansion, that is, what we see appear to expand. The center of the focus of the expansion indicates the direction in which we are heading or our self-motion. In area MSTd, many neurons are selective for expansion stimuli. More so, when we translate through the environment, we often make smooth gaze shifts with eye or head movements. These gaze movements complicate the motion on the retinas because they add a laminar motion due to observer translation. In short, the dorsal portion of MSTd supports the view that MST is suited for the analysis of wide-field egomotion induced by head and body movements. Projects along with MT to the dorsolateral pontine nuclei in the brain stem.

"Microsaccades" are herein defined as much smaller movements constantly occurring in the oculomotor system, with amplitude of around 5 minutes. Microsaccades occur within a background of high frequency oscillation of the eye, known as tremor. These two types of movements probably reflect instability or noise, which is naturally intrinsically inherent in the nerves and muscles that assist in controlling the positions of the eye. For the later reason eye fixations should be better understood as if the eyes attaining a quasi-stationary states.

"Movements" are herein defined as imminent real-time actions that the perceiver executes, within its own reachable space. In particular, early perception of stimuli attributes within egocentric space triggers in the perceiver imminent action. Preferably, stimuli attributes are implicitly and unconsciously encoded as movements. Within the particular context of action-perception loops, it is understood that "movements in egocentric space, are not a communicative act in them selves. In other words, the executer of movements in egocentric space never intended implicitly or explicitly to convey a (any kind of) message to another perceiver/observer via the execution of its own movements. Movements in egocentric space, once underway, cannot be consciously aborted, delayed or inhibited.

"Optical flow" refers in general to the description of the motion field associated with a sequence of perceptual images. In particular, it refers as the total pattern of light entering the eye (optic array) and the transformation of it, often as a consequence of the observer's own movements (Gibson, J. J. (1979). The ecological approach to visual perception. Boston: Houghton Mifflin; Horn, B. K. P. and Schunck, B. G. (1981). "Determining optical flow". *Artificial Intelligence*, 17:185-203). When a viewer moves relative to the environment, the visual image projected onto the retina changes accordingly, and can be decomposed into several basic components, including redial, circular, translation and sheer motion. Within small regions of the retina and for short time durations, this motion approximates a two-dimensional translation. The field of velocity vectors associate with each such region is referred as 'optic flow'. Preferably, optic flow refers to transformations of the pattern of stimulation over time, that is, characteristic fluctuations in the spatial pattern of light are encoded within the optic flow field. Hence, optical flow introduces the time dimension into perception, so that all perception becomes motion perception. More so, in support of defining perception, in terms of "motion perception", J. J. Gibson rejected the equation of the eye with a camera, and the consequent analysis of vision in terms of processing static images. He argued that vision provides an informational rich stimulus that rendered redundant any requirement for internal representations of the world. Consequently, the optic flow is an integral part of perception and contains information regarding heading (Bradley, D. C., Maxwell, M., Andersen, R. A., Banks, M. S., and Shenoy, K. V. 1996. Neural mechanisms of heading perception in primate visual cortex. Science 273, 1544-1547; Lee, D. N. (1976). A theory of visual control of braking based on information about time-to-collision. *Perception*, 5, 437-457; Royden, C. S., Crowell, J. A., and Banks, M. K. S. 1994. Estimating heading during eye movements. Vision Res. 34, 3197-3214), self-motion (Freeman, T. C. A., & Banks, M. S. (1998). Perceived Head-centric Speed is Affected by Both Extra-retinal and Retinal Errors. *Vision Research*, 38, 941-945; Gibson, J. J. (1979). The ecological approach to visual perception. Boston: Houghton Mifflin; Krapp, H. G., & Hengstenberg, R. (1996). Estimation of self-motion by optic flow processing in single visual interneurons. *Nature*, 384, 463-466), depth (Cornilleau-Peres, V., & Gielen, C. C. A. M. (1996). Interactions between self-motion and depth perception in the processing of optic flow. *Trends in the neurosciences*, 19, 196-202; Rogers, B. J., & Graham, M. (1982). Similarities between motion parallax and stereopsis in human depth perception. *Vision Research*, 22, 261-270) and time collision (Lee, D. N. (1976). A theory of visual control of braking based on information about time-to-collision. *Perception*, 5, 437-457; Tresilian, J. R. (1997). Correcting some misconceptions of time-to-collision: a critical note. *Perception*, 26, 229-236; Wang, Y., & Frost, B. J. (1992). Time to collision is signalled by neurons in the nucleus rotundus of pigeons. *Nature*, 356, 236-238). During the past two decades, special attention has being given to the recognition of shape/form from motion. Physiological studies have recognized in the macaque monkeys that the neural circuitry underlying motion discrimination passes through striate cortex, to the middle temporal motion area (MT/V5). In cerebral area MT/V5 it's hypothesize to be, a representation of the velocity of the image for different regions of the visual field (Albright, T. D., Desimone, R., and Gross, C. G 1984. Columnar organization of directionally selective cells in visual area MT of the macaque. J. Neurophysiol, 51, 16-31) and additionally neurons in this area are highly directional selective. This motion representation is further processed in the medial superior temporal dorsal area (MSTd) in which neurons are found to respond to global environmental optic flow for spatial vision (Tanaka, K. K., Hikosaka, H., Saito, M., Yukie, F., and Iwai, E. 1986. Analysis of local and wide-field movements in the superior temporal visual areas of the macaque monkey. J. Neurosci. 6, 134-144; Duffy, C. J., and Wurtz, R. H. 1991a. Sensitivity of MST neurons to optic flow stimuli. I. A continuum of response selectivity to large-field stimuli. J. Neurophysiol. 65, 1329-1345; Duffy, C. J., and Wurtz, R. H. 1991b. Sensitivity of MST neurons to optic flow stimuli. II. Mechanisms of response selectivity revealed by small-field stimuli. J. Neurophysiol. 15, 1346-1359). Beyond MST, the motion signal passes to the parietal cortex (Siegel, R. M., and Read H. L. 1997. Analysis of optic flow in the monkey parietal area 7a. Cereb. Cortex 7: 327-346) in which optic flow signals are further processed and combined with eye position information. The above neurophysiological findings have gained momentum from studies demonstrating the existence of analogous neural units in humans that integrate local-motion signals along complex flow trajectories (Regan, D. & Beverley, K. I. 1979. Visually guided locomotion: Psychophysical evidence for a neural mechanism sensitive to flow patterns. Science 205, 311-313; Morrone, M. C., Burr, D. C. & Vaina, L. 1995. Two stages of visual processing for radial and circular motion. Nature 376, 507-509). Additionally, there is some emerging evidence in humans for selectivity along the 'cardinal directions' of optic flow (radial and circular).

"Pick up/extraction of relational information" refers herein to a natural capacity of most organisms to implicitly extract relations and/or correlations (statistical significance or invariance's) from a stimuli array, namely, focusing on the direct extraction of environmental structure. Preferably, Statistical probability theory posits that we learn (unconsciously) about regularly occurring events in the perceptual environment by determining the likelihood of each event's occurrence (Aslin, R. N., Saffran, J. R., & Newport, E. L. 1998. Computational of conditional probability statistics by 8-month-old infants. Psychological Science, 9, 321-324). In particular, our sensory world is, statistically speaking, a highly predictable place. It should not come as a surprise that early perception is well tuned to this statistical structure. Moreover, events in the environment tend to follow quasi-regular patterns. For example, in sensory perception neighboring regions in the perceptual space are highly correlated; a property that in the visual domain is relevant for detecting edges in visual scenes. In human language, picking up the frequency with which syllables co-occur may be helpful in discovering word boundaries, just as learning about the statistics of word co-occurrences appear to be helpful in determining syntactic structure.

"Perceptual Visual Awareness" herein refers to an implicit automatic perceptual sensorial awareness occurring between 60 to 80 milliseconds in a subject. However, this perceptual awareness is insufficient for discriminating detailed properties of objects in allocentric space.

"Perception" in its broad definition encompasses both conscious and unconscious effects of sensory stimulation on behavior. In particular visual perception is herein defined as a modular and integrative process, which is then divided into two functional phases:

Phase-1) an early perceptual phase, where perceiving literally means, "acting in the environment" namely, perceiving calls for the direct and imminent deployment of a physical force within the perceiver's reachable space rather than being a passive and contemplative mental process localized in the perceiver's brain. More so, early perception motor loops taking place within the perceiver's reachable space should be considered as if indistinguishable from "acting." Preferably, early visual perception refers to an unconscious act demanding the active participation of the perceiver in implicitly extracting from his/her reachable space, relational information (not energy attributes) from a sensorial stimuli light array. Preferably, the term visual perception refers in here to an early stage in visual perception, named early visual perception, where either endogenous or exogenous influences impact behavior only implicitly and unconsciously.

Phase-2) ordinary visual perception refers herein, to a conscious perceptual process explicitly under the influence of endogenous factors including, intention, attention, memory and learning. Particularly, perception in general and visual perception in particular refers to a process responsible for organizing sensorial stimuli information into a coherent framework, which is highly dependent on processing speed, storage capacity and lately to a functional and structural coherence distributed across the neural circuitry (neural networks) in the brain. Preferably, ordinary perception refers to visual perception and specifically, to the role assigned to the ventral neuropathway in processing visual information such that accomplishing discrimination, denotation and categorization of objects shape, color and size in the environment at large namely, allocentric space.

"Photic perceptual attributes" herein refer to visual perceptual informational properties other than energetic parameter (wavelength, amplitude, distribution), that ambient light assumes due to having physically interact with a biological system. Such visual perceptual informational attributes are mostly related to intrinsic spatiotemporal fluctuations originating from within the biological habitat, which transforms energetic spatiotemporal information contained in the optical field, such that the spatiotemporal informational patterning of the optical field will intrinsically fluctuate and be of such an energetic magnitude, that can directly trigger imminent ballistic movements among many physically distributed body parts in the reachable space of a subject. Examples of photic perceptual informational attributes are: a) synchronization of ambient light stimuli to intrinsic variable physiological mechanical activity occurring in visceral space of a subject; 2) spatiotemporal fluctuations of visual indicia; 3) visual indicia relationships based on simple (basic) correlations (like a simple distinction between distractors and targets in a visual scene which triggers covert attention). Photic perceptual informational attributes are a direct reflection of an active and reciprocally interaction-taking place between the biological system and ambient energy, namely the environment. Photic perceptual informational attributes populate egocentric space of a subject. Therefore, they should be considered as of being an integral part of the informational functional potential for mapping egocentric spaces that a subject possesses at any time to guide imminent motor behavior in reachable space. Photic perceptual informational attributes are centered related information namely, they generate active veridical personal experiences thus, not communicable (via verbal report) to any other perceiver.

"Physiological indices" herein refer to neural imaging devices, which have been developed in order to track and record the activity of the brain associate with some patterning of stimulation. The neuro-imaging techniques, Positron emission tomography (PET scans) and magnetic resonance imaging (MRI) relay on computerized tomography, which converts small signals from a range of positions into a model of the brain. When some radioactive substance has been administer and absorbed into the blood stream the brain areas that are subsequently most active have the highest radioactivity, and this can be detected by PET scans. Thus, the sites of heightened neural activity associated with a particular perceptual task receive a greater blood flow and therefore provide a stronger signal for the detector. Functional MRI (fMRI) measures are more useful for perceptual research, as they are concerned with differences in MRI measured in control and experimental conditions. Cells that are active under the experimental conditions utilize more oxygen and can be detected and imaged. Spatial resolution of fMRI is superior to that of PET scans. Both these procedures correlate changes in oxygen or nutrient use with brain activity.

"Posterior parietal cortex" (PPC) refers to a cerebral area involved in the spatial aspects of movements (Ungeleider, L. G., & Mishkin, M. (1982). Two cortical visual systems. In D. J. Ingle, M. A. Goodale, & R. J. W. Mansfield (Eds.), Analysis of visual behavior (pp. 549-586). Cambridge, Mass.: MIT Press), integrates depth and coordinates visually guided actions. The PPC is an end point of one of the mayor streams of visual processing in the primate visual cortex. The pathway of the parietal cortex is located in dorsal areas of the extrastriate cortex and is involve in spatial aspects of visual processing. It is a cerebral area responsible for integrating visual-motor information. In the PPC signals form different modalities, such as visual, tactile, auditory, vestibular and proprioceptive inputs, are combined to create a sensorimotor representation of space that can be used to plan and control body movements. PPC area 7a is involved in the further analysis of optic flow beyond the cortical areas MT and MST and provides a novel representation of motion. Area 7a utilizes motion for the construction of a spatial representation of extra-personal space (from egocentric mappings of space) and its involved with visual attention. In other words, the PPC is an area that transforms visual information from retinal to head and body-centered coordinates. More so, neurons in many areas of the PPC are known to respond to optic flow stimuli (area 7a). Since it's known that optic flow is a substantial source of visual information concerning control and planning self-motion and to avoid obstacles during locomotion. Additionally, human lesions of PPC cause: a) difficulty in guiding hands to objects in space (optic ataxia); b) inability to maintain eyes fixed on an object; c) inability to scan a scene; d) inability to locate an object in space; e) inability to perceive more than one object at a time (simultagnosia).

"Pre-attention" herein refers to a mode of operation of visual perception where no complex forms are processed. Typically, visual tasks that can be performed on large multi-element displays in less than 200 msec are considered preattentive. Pre-attention occurs in parallel, without effort or scrutiny, differences in a few local conspicuous features are detected over (discreet) time over the entire visual field. If search times is relatively constant and bellow some chosen threshold, independent of the number of distractors, the search is said to be preattentive. Many researches in the field of visual perception suggest that this parallel searching of visual information in a display is a key functional property of the low-level visual system.

"Proprioceptive system" herein refers to a bodily sensory information system, which has its receptors e.g. in muscles, tendons and joints, physically distributed on multiple locations in the body. Those receptors create sensory information by the contracting and stretching of muscles and by the bending and straightening, pulling and compression of joints between bones. This information is being constantly sent to the brain so that it can keep track of where all our body parts are and what they are doing without our having to look at them. Proprioception can be described as the mind's awareness of the body. Accomplishing a physical sense of "self" upon which we can base a psychological sense of self-awareness, which reflects adequate integration of proprioceptive information. Proprioceptive input helps integrate other types of stimulation such as vestibular and tactile and aids in organizing behavior. Proprioception plays an important role in the control of movement it is an important source of feedback information, when action is under closed loop control. There are two kinds of close loops: a) close-loop, attentional—visual and proprioceptive information received by brain and responses are modified in periods longer than 200 msec and b) close-loop, unconscious—proprioceptive information can be used to modify responses through spinal cord and reflexes. In general, closed-loop reflexive control corrections have rapid latencies 30 to 50 msec and do not require attention (motor system can respond to changes that are too small to be detected consciously). Long-loop reflexes in their own respond to a muscle stretch with a latency of 50 to 80 msec.

"Reading"—Human vision relies extensively on the ability to make saccadic eye movements, which are made at the rate of about three per second, orient the high-acuity foveal region of the eye over targets of interest in a visual scene. When people read sentences their fixations are typically between 60 and 500 ms long, being about 250 ms on average. Saccades are known to be ballistic, i.e., their final location is computed prior to making the movement and the trajectory of the movement is uninterrupted by incoming visual signals. Saccades are on average 7-9 characters in size. However, they vary in length, some being the length of only one character, while others may be almost as long as the sentence itself. Readers tend to fixate content words, which are usually quite long, but skip function words, which tend to be quite short. The number of characters that a reader can identify on any fixation is termed the visual span, and the number of characters that a reader processes at least partially during a fixation is termed the perceptual span. The perceptual span is asymmetrical about the point of fixation, being extended towards the direction in which the reader progresses through the text. Readers not only process text that they are fixating, but also pre-process text in the direction that they are reading. Additionally, readers make more fixations and fixate for longer when they experience processing difficulty and perform regressive saccades to re-read text to recover misanalyses sentences.

"Set of Energetic Optical Quanta" refers herein to a set that comprises a number of M photons of wavelength inside any frequency band in the spectral electromagnetic radiation, extending from the ultraviolet to the infrared regions, including the visible light region of the spectrum. Such a set possesses a particular (statistically informational stable) photon configuration inside an interval $\Delta t$. The set also comprises any number of N photons sub-sets, having any wavelength inside any frequency band, which is already contained inside the frequency region of the set.

"Simple optical flow fields" refers herein as generating a low dimensional (1-D to 2-D) perceptual intrinsic and variable visual dynamic environment such that the kinematical freedom of the generated and comprised velocity vectors in such a simple optic flow field will be constrained to move only in kinematical trajectories parallel to a 1-D or 2-D plane. Simple optical flow fields are strongly responsive to visual disparities and visual motion transparencies. Preferably a simple optical flow field will be such as to optimally trigger neuronal firing in area MT. Hence, the generated perceptual kinematical attributes will be restricted such that to satisfy a simple optical flow field. A simple optical flow field reduces vestibular input, thus less central processing of information is required for eye positioning corrections and avoids complex transformations of information required for either self-motion and/or object motion. Kinematical trajectories conveying a complex optical flow field to the subject such as: radial (expansion/contraction), circular, radial-rotational (spiral motion), radial-circular and some forms of planar motions generating possible complex global flow fields are not allowed.

"Superior Colliculus" (SC) refers herein to an additional visual pathway which conveys information to the pulvinar nucleus. The SC is a brain structure located on the dorsal surface of the brain stem After subcortically processing in the SC, information is conveyed to the Pulvinar Nucleus of the thalamus. From the pulvinar Nucleus, visual information is conveyed to secondary regions of visual cortex (MT/V5)

for additional processing. Inputs from both the SC and primary visual cortex contribute to the movement sensitivity of MT/V5 neurons. The SC coordinates visual, somatic and auditory information, adjusting movements of the head and eyes towards the stimulus. There is strong evidence to suggest that multi-modal sensory integration takes place in the deep layers of DC. Unconscious visual input goes directly from the retina to the colliculus, and therefore implicates this neural tissue in navigational processing. In addition to information from the retina, the SC receives auditory information, vestibular information about head position and visual information that has already been processed by primary visual cortex. This mixture of information is integrated by the SC in such a way as to control movements of the head and body made in orientation to visual targets of novelty or interest. Hence, the SC is responsible for the control of goal directed orientation responses towards novel sensory stimuli. Output from the SC goes to motor centers responsible for orienting behaviors. Orienting behaviors are immediate, rapid organism responses (reflexes), usually to movement. In addition, the SC is involved in the control of two types of eye movements, rapid eye movements (called saccades) that are made toward moving visual targets and slow movements (called pursuit eye movements) that are used for tracking visual stimuli. Although, the SC is usually described as a visual reflex center, it receives inputs from auditory and somatosensory centers thus the SC is not exclusively related to visual functions. Instead, it plays a role in helping orient the head and eyes to all types of sensory stimuli.

"Vestibular system" herein refers to a sensory system that has its receptors in the inner ear and senses movements of the head in all planes. The sensory input we get throughout the vestibular system tells us exactly where we are in relation to gravity (whether it needs to make postural adjustment to prevent falling) whether we are still or moving, how fast we are going (information about changes in velocity—speeding up or slowing down), and in which direction. The vestibular system does not enter consciousness but through its influence on muscle tone the vestibular system, it's essential for achieving motor coordination, and posture. The vestibular system plays a mayor role in controlling the muscles that move the eyes, so that in spite of the changes in head position, which occur during normal activities such as walking and running, the eyes remain stabilized through out space. Vestibular-ocular reflex (VOR) is an important mechanism by which unblurred vision is maintained in spite head movements (e.g. if the head is turned to the left, this reflex causes the eyes to move to the right and vise versa). When the vestibular system malfunctions, the brain receives nerve impulses that are no longer accurate, causing it to perceive the information as distorted or off balance. In response, the brain causes the eyes to move back and forth, which creates a sensation of disorientation, vertigo or dizziness.

"Visceral space" here in refers to the Autonomic Nervous System (also known as the visceral system) is a division of the nervous system that controls bodily functions that occur autonomously and automatically (without conscious thought) within the body. In particular, visceral space is not open to the scrutiny of sensorial ordinary perception, namely its spatiotemporal habitat is closed to sensorial observation of any kind (intentional or unintentional). However, the egocentric mapping of space of a subject has some access to some functional aspects of visceral space (mechanical functions), while unconsciously triggering imminent ballistic movements in reachable space, that is, while actively involved in early perceptual-motor action loops. The proprioceptive system information via reflexive feedback loops in a subject, helps a great deal in providing an implicit and unconscious (sensorial) boundary to visceral space. The Autonomic or Visceral system sends signals to smooth muscles and glands (involuntary control); this system has two divisions which act in opposition to each other: 1) Parasympathetic system nerves tend to slow down body activity during times of little stress. 2) Sympathetic system nerves increase overall body activity during times of stress, excitement, or danger. Some examples of body systems/responses involved: respiration, heart rate, blood pressure, vascular tone, digestion, rumination, vomiting, micturition, defecation, erection, ejaculation, sleep, arousal, body temperature, appetite, etc. Functionally involved with the maintenance of "homeostasis" and with the changes in visceral function, which accompany emergency situations (fight or flight). Notes: The autonomic system is present in both central and peripheral nervous system and there are efferent (motor) and afferent (sensory) components. However, traditional definitions suggest that this is entirely a motor system. The sensory component of visceral control is often referred to as "general visceral afferent" (GVA). The autonomic system is sometimes called the general visceral efferent system. The Autonomic Nervous System is controlled mainly by centers in: 1) Hypothalamus: Master control center-2) Spinal Cord: thoracic and sacral segments-3) Brain Stem: Special control functions (respiratory center, vasomotor center etc.) The system is functionally and anatomically divided into two divisions: Both divisions are controlled by the hypothalamus (represents about 4% of the brain mass and controls the brain-stem). The hypothalamus directs information to the reticular formation (brain stem), which passes motor instructions on to the sympathetic or parasympathetic system. The system is similar in many ways to the somatic nervous system: there are "upper motor neurons" which descend from the brain in the white matter of the spinal cord and synapse on "lower motor neurons" in the thoracic and sacral spinal cord.

"Visual pathways"—refers herein to the neurobiological account underlying the development of the visual system. Neurobiological functional modeling of the visual system start from the neurological mapping of two visual systems, a phylogenetically older retinotectal system, which the dominant destination retinal projections in lower mammals and a newer geniculostriate system which is the dominant target for retinal information in higher mammals, particularly primates. The main geniculostriate pathway is the long pathway from the retina via the LGN in the thalamus to the primary visual cortex (V1) and from there subdivides into two functional separate visual streams. In contrast, the subcortical retinotectal pathway transfers information to the superior colliculus (SC) in the brain stem and via pulvinar to the visual associative functions. More so, whereas the geniculostriate system receives information from the cone-rich areas of the retina, the retinotectal system via the SC receives information from the rod-rich areas found in the periphery of the retina. The collection of cones in the foveal region of the retina provides the greatest visual acuity that needed for the feature detection to occur further up the pathway in primary visual cortex. The peripheral roads, although low in acuity, are particularly sensitive to movement. Growing accumulating evidence for a major division within cortical processing in the macaque, pioneered by Zeki (Zeki S. M. 1974. Functional organization of a visual area in the posterior bank of the superior temporal sulcus of the rhesus monkey. J Psysiol 236: 549-573; Zeki S. M. 1978.

Functional specialization in the visual cortex of rhesus monkey. Nature 274, 423-428; Zeki S. M. 1983a Colour coding in the cerebral cortex: the reaction of cells in monkey visual cortex to wavelength and colours. Neuroscience, 9, 741-765; Zeki S. M. 1983b Colour coding in the cerebral cortex: The response of wavelength-selective and colour coded cells in monkey visual cortex to changes in wavelength composition. Neuroscience, 9, 767-781), demonstrated distinct extra-striate brain areas containing neurons responding to particular visual attributes, such a selective area for motion information (V5, also known as MT) and a color specific area (V4). These distinct cortical areas for processing visual information came to be seen forming two broad, functionally, different processing streams, the dorsal and ventral streams proposed by Ungerlider and Mishkin (Ungeleider, L. G., & Mishkin, M. (1982). Two cortical visual systems. In D. J. Ingle, M. A. Goodale, & R. J. W. Mansfield (Eds.), Analysis of visual behavior (pp. 549-586). Cambridge, Mass.: MIT Press). The dorsal stream (including V5) transmitted information to the PPC for localizing objects within spatial array (where) and the ventral stream (including V4) processed information for the ITC, concerned with the 'what' aspects of objects, such as form, color and face recognition. Visual pathway transfers different types of visual information from the retina via different nerve fibers. Parvocellular (P) fibers transfer color and high contrast black & white detail information. Magnocellular (M) fibers transfer motion information and low contrast black & white information. These systems are distinct morphologically at retina and LGN. Particularly, the magnocellular stream subserves movement perception and some aspects of stereoscopic vision associated with spatial layout in the dorsal stream. The parvocellular system show high acuity and wavelength selectivity needed for analysis of form and color in the ventral stream. Glickstein & May (Glickstein, M & May, J. G 1982. Visual control of movement: the circuits which link visual to motor areas of the brain with special references to the visual input to the pons and the cerebellum. In contribution to sensory physiology, vol. 7 (ed. W. D. Neff), pp 103-145. New York: Academic Press) in a review reached a different conclusion as to the functions of the two systems. They reported that several dorsal visual areas send profuse neuronal projections to the SC and to motor nuclei in the pons, while none of the ventral visual areas do this. These brain stem target structures in turn supply visual information to the cerebellum (the SC via the pontine nuclei). They concluded that all accumulated behavioral, anatomical and physiological evidence suggests that the parietal lobe visual areas are especially concerned with the 'visual guidance of movement'. More recent evidence reports that areas in the dorsal system project not only to sensorimotor areas in the brain stem, but also to specific premotor areas in the frontal lobe, each related to different action domains such as saccadic eye movement, arm reaching movements, and hand grasping movements (Cavada C. & Goldman-Rakic, P. S. 1989. Posterior parietal cortex in rhesus monkey. II. Evidence for segregated cortico-cortical networks linking sensory and limbic areas with the frontal lobe. J. Comp. Neurol. 287, 422-455; Boussaoud, D., Di Pellegrino, G. & Wise, S. P. 1996. Frontal lobe mechanisms subserving vision-for-action versus vision-for-perception. Behav. Brain Res. 72, 1-15; Wise, S. P., Boussaoud, D., Johnson, P. B. & Camimiti, R. 1997. Premotor and parietal cortex: corticocortical connectivity and combinatorical computataions. A. Rev. Neurosci. 20, 25-42). In contrast, the ITC has strong reciprocal connections with amygdala. The amygdala is implicated in processes of learning to associate visual stimuli with reward and also with social and emotional cues (Kling, A. & Brothers, L. 1992. The amygdala and social behavior. In the amygdala: neurobiological aspects of emotion, memory, and mental dysfunction (ed. J. Aggleton), pp. 353-377. New York: Wiley-Liss; Brothers, L. & Ring, B. 1993. Mesial temporal neurons in the macaque monkey with responses selective for aspects of social stimuli. Behav. Brain Res. 57, 53-61). Thus, whereas the dorsal system has direct and rapid access to motor-related systems, the ventral system seems to provide the visual route to associative learning, and can thereby mediate more flexible and for a longer-term visual effects on behavior. In ontological development, even simple early deficits in a particular pathway may have a complex consequence. For example, motion-processing deficit related to the magnocellular stream had been hypothesized for developmental dyslexics (Livingstone, M. S et al. (1991) Physiological and anatomical evidence for a magnocellular defect in developmental dyslexia. Proc. Natl. Acad. Sci. U.S.A. 88, 7943-7947), elevated motion coherence thresholds (Cornelissen, P. et al. (1995). Contrast sensitivity and coherent motion detection measured at photopic luminance levels in dyslexics and controls. Vis Res. 35, 1483-1494; Witton, C. et al. (1998). Sensitivity to dynamic auditory and visual stimuli predicts nonword reading ability in both dyslexic and normal readers. Curr. Biol. 8, 791-797) and motion responses of area V5 revealed by functional brain imaging (Eden, G. F., vanMeter, J. W., Rumsey, J., Maisog, J. M., Woods, R. P., and Zeffiro, T. A. 1996b. Abnormal processing of visual motion in dyslexia revealed by functional brain imaging. Nature 382: 66-69).

The present invention provides a method and apparatus for structuring any visual scenery into various degrees of pre-attentive features embedded within perceptual kinematical attributes conveyed by an intrinsic variable simple optical flow field. Such constructions are necessary for maximizing the pre-conscious pickup of relational visual (sensorial) information from motion perception in the visual scene, which precedes the first storage of information (short-term memory) and discrimination of object details, by the more dominant visual ventral stream. Pre-attentive extraction of relational information from perceptual kinematical attributes from an intrinsic variable simple optical flow field, has the enormous advantage of being performed at once on the entire visual field picking up basic features including gross differences (conjectures) in line ends (terminators), brightness (shadows), closure, colors, tilt, curvature, size, etc.

It is hypothesized herein that the direct and implicit extraction of relational information from the above-mentioned early visual perceptual task involving multidimensional pre-attentive features, together interpolated with other perceptual kinematical attributes of an intrinsic variable simple optical flow field is done quickly (30 to 250 msc), effortlessly, without any attention being focused on the visual display.

Moreover, the teachings of this invention aim to parcel visual perceptual mechanisms into two basic modular phases: (1) an early visual perceptual phase, where perception automatically triggers imminent ballistic movements in egocentric space (reachable space) and vise versa; (2) a later visual phase, where ordinary perception principally trough the deployment of focus attention, reassembles direct information extracted via pre-attentive cuing and perceptual kinematical shape from a simple intrinsic variable optic flow field, into original objects and then performs identification (via the ventral stream) and categorization (higher cognitive functions) of the identified objects and puts them into a meaningful framework, namely, the recognition of an object and its relational place in allocentric space.

Moreover, on the one hand, the former step exploits the meshing of a multidimensional informational array of pre-attentive perceptual attributes embedded within a intrinsically variable simple optical flow field, enabling the subject to pre-attentively (automatically) attain the direct and implicit extraction of relational information from the visual scene and also, effectively guiding the subsequent deployment of its attention. On the other hand, the later perceptual visual phase serially searches (focus attention) the visual scenery and therefore processes and stores visual information within the limitations imposed by the attentional mechanism capacity.

In line with the above-mentioned phase "1", and in order to further enhanced the implicit potential for pre-attentive cuing in the subject (at the same time also shielding him or her from attentional capacity limits), we have quasi-randomized the spatial-temporal distribution of perceptual attributes in the intrinsic variable simple optical flow field conveyed to the subject. Hence, the resulting visual perceptual construct prevents the subject's attention mechanisms (vigilance, and focus attention) from intentionally being deployed towards initializing serial searches in multiple regions in the visual display. Real time quasi-randomization of perceptual visual kinematical stimuli attributes, denies attentional mechanisms the access to explicit cognitive representations, as the subject (consciously) attempts to establish a causal link between: a) what is actually being shown in the screen display and/or b) what its actually being shown in the screen display, what is it? (information stored in long term memory is being retrieved to establish an explicit association with the visual seen at hand, in order to discriminate and categorize objects (in the visual scenery in allocentric space). Both questions reflect the perceiver's intentional attempts to successfully decode the visual seen at hand, by cognitively engaging in an associative learning process.

Both functional modules of visual perception are neurologically sub-served by the dorsal and ventral streams, and we functionally view them as co-existing and synergicaly interacting in visual ordinary perception. Since attention affects both spatial and temporal aspects of visual processing, the teachings of the present invention indicate that a temporal intrinsic variable modulation influencing in real time the implicit extraction of relational information via pre-attentive cueing in a subject, especially when pre-attentive cuing (the targets) depicts a kinematical shape conveyed by an intrinsic variable simple optical flow field, will suffice to accelerate information processing. Accordingly, a more efficient processing of information grants a faster discrimination and categorization of objects and their relational metric in allocentric space. Hence, resulting in faster processing of information for word recognition before the potentially interfering effects of upcoming stimuli take place.

The present invention makes use of the numerous advantages rendered by a intrinsic variable visual dynamic environment as directly and effortlessly conveyed to the perceiver via an intrinsic variable simple optical flow field, but also by pre-attentive features embedded within such an intrinsic variable simple optical flow field. Consequently, the intrinsic variable simple optical flow field is structured in such a way as to implicitly afford being picked-up by covert attention via early visual perception, serving to boost the rate at which target (cue) information is extracted directly (by enhancing the signal in a noisy environment—distractors) or, alternatively, speeding overall visual information processing by enabling the perceiver to exclude task-irrelevant information from noise sources (Carrasco, M. & McElree, B. (2001). Covert attention speeds the accrual of visual information. Proceedings of the National Academy of Sciences, 98, 5341-5436).

Additional teachings of the present invention focus on the visual representation of space. Recent studies (the induced Roelof's Effect, Bridgeman, B., Kirch, M., & Sperling, A. (1981). Segregation of cognitive and motor aspects of visual function using induced motion. Perception and psychophysics, 29, 336-342). suggest the existence of two different representations of visual space: a cognitive representation devoted to conscious discrimination permitting categorization, denotation and a sensorimotor representation devoted to unaware egocentric localization of reachable objects. Whereas sensorimotor representations in egocentric space reflect behavior with a purely instrumental goal, cognitive representations strongly reflect behavior with a communicatory goal. Furthermore, the cognitive system stores information for use in controlling future behavior, while the sensorimotor system in egocentric space controls behavior in real time.

What's more, it is hypothesized in the related art that the sensorimotor representation of space is conveyed through specific anatomical pathways stemming from the primary visual cortex: the dorsal stream leading to the posterior parietal area, and the ventral stream leading to the inferotemporal cortex. In an embodiment of the present invention, the apparatus and method combine together the implicit extraction of relational information facilitated by interpolating pre-attentive features, with an intrinsically variable simple optical flow field. The present invention effectively reinforces the perceiver's potential for implicit awareness of his/hers egocentric space. Such enhanced implicit acuity towards the subject's (own) reachable space, is conveyed via visual transient stimuli, which is mainly projected onto the dorsal stream. Hence, providing a stronger implicit representation of a sensorimotor mapping of space due to the subject's possession of a greater potential for extracting relational information via imminent ballistic movement in (his/her own) reachable space.

The teachings of the present invention suggest that a perceptual sensorimotor mapping of space is preferably a 'dynamic mapping of space', namely that egocentric spaces implicit informational representations are not compressible via perception to a single frozen interval in time, but rather to a sequence of perceptual temporal events. Moreover, a perceptual sensorimotor mapping of space developmentally bridges and interfaces between early perceptual-motor acts occurring in reachable space, and the mental generation of the very first outburst of a cognitive representation of any kind, namely, the explicit representation of 'time discreteness'. Particularly, such a cognitive representation about time spans, its being planned and rehearsed by the cerebellum, a brain structure thought until now to be only involved in controlling and coordinating complex motor behavior. Time discreetness, its about the very first explicit mental mapping of temporal space representing temporal event durations among executed imminent sequential ballistic movements in reachable space.

In other words, a developmentally normal sensorimotor mapping of egocentric space strongly depends and reflects the potential for generating an explicit early perceptual internalization of time discreteness. In contrast, a cognitive mapping of space mainly provided by the processing of visual information via the neuropathway in the ventral stream, accomplishes ideal static representations of objects, from which an allocentric 3D space emerges as a relational metric among static recognized objects. More so, a cognitive mapping of space also depends in explicitly identifying a causal relationship among objects. In other words, a cognitive mapping of space strongly depends on an explicit ordinary perceptual internalization of the arrow of time, namely subjectively recognizing the flow of time, were the present is causally linked to the past.

The teachings of this invention make noticeable the benefits to be attained by utilizing the apparatus and method herein presented. These benefits imply that the automatic attainment of a stronger implicit sensorimotor mapping of space, will dramatically contribute in securing a normal cognitive development. The reasons for this are: 1) An implicit awareness of egocentric space accounts for a greater capacity the organism possesses at any single moment in time, for being capable of automatically integrating different sources of information (including vestibular, proprioceptive and mainly (visual) optic flow information) into a single grand source. Hence, in the absence of head movement change (lack of vestibular input) and/or when there is a conflict between proprioceptive and ventral information (report of visual illusions), the organism having a robust non-cognitive awareness about its egocentric space, is capable of compensating faster for any lack or shortage of spatiotemporal information and thus, is less susceptible to endogenous distortions originating within its cognitive circuitry (top-bottom processes); 2) Cognitive resources including short-term memory, attention and learning are less committed in aiding thus, compensating for an incomplete mapping of egocentric perceptual sensorimotor space (such a loss most commonly hinders the unconscious execution of fluent movements in reachable space).

In general, the liberation of cognitive resources, positively impacts information processing of sensorial stimuli. More so, an accelerated processing of information brings about a faster discrimination and categorization of visual stimuli by the ventral neuropathway (target signal enhancement). And last but no less important, the very process of visual ordinary perception should enormously benefit from a faster information processing, due to the perceiver having to be less susceptible to distortions and/or errors (optical illusions) originating in his own perceptual field of vision. Hence, information processing acceleration is also influenced by a reduced attentional sensitivity towards environmental sources of noise (distractors).

The herein teachings of the present invention also focus on the developmental influence that inhibitory processes have on cognitive resources. Recent investigations (Howe, M. L. & Pasnak, R. (Eds.) 1993. Emerging themes in cognitive development Vol.I: Foundations NY: Spring-Verlag) point out that inhibitory processes also contribute in improving processing efficiency and other aspects of behavior. Normal control and deployment of inhibition has proven to: a) better suppress reflexive or prepotent responses as children grow older (Diamond, [A. (1990). Developmental time course in human infants and infant monkeys, and the neural bases of inhibitory, control in reaching. In A. Diamond (Ed.), *The development and neural bases of higher cognitive functions* (pp. 637-676). New York: New York Academy of Sciences; Diamond, A., Cruttenden, L., & Nederman, D. 1994. AB with multiple wells: I. Why are multiple wells sometimes easier than two wells? II. Memory or memory+inhibition. Developmental Psychology, 30, 192-205); b) decrease sensitivity to noise in selective attention tasks (Ridderinkhof, K. R., & van der Molen, M. W. (1995). A psychophysiological analysis of developmental differences in the ability to resist interference. *Child Development,* 1995; 66: 1040-1056; Burack, J. A., & Enns, J. T., Eds. (1997). Attention, development, and psychopathology: A merging of disciplines. New York: Guildford Publications); c) reduce sensitivity to distractors in memory tasks (Bjorklund, D. F., & Harnishfeger, K. K. (1990). The resources construct in cognitive development: Diverse sources of evidence and a model of inefficient inhibition. Developmental Review, 10, 48-71); d) inhibit previously correct solutions that are currently incorrect.

The present method and apparatus in the herein invention provides the means by which indicia being displayed as part of a intrinsic variable visual dynamical environment are constructed in such a way as to interpolate several preattentive (features) dimensions meshing with an intrinsic variable simple optical flow field. The present method and apparatus in the herein invention aims to non-cognitively and implicitly extract relational information from a visual stimuli array. Thus, the perceiver actively accomplishes efficient early perceptual-motor loops, as reflected by a robust awareness of his/her own egocentric space. The active accomplishing of such perceptual-motor loop goal is only achievable if the perceiver is to a great degree capable of mental generating an explicit representation of time events. In general, the explicit generation of a mapping of time discreteness from a visual stimuli array concerns with multiple endogenous factors, but principally with 'expectations' and 'predictions' that the perceiver actively generates about the nature of the stimulus at hand. When expectations and/or predictions are violated, orienting occurs (Sokolov, E. N. 1963. Perception and the conditioned reflex. Oxford: Pergamon). It involves inhibition of ongoing behavior and increased vigilance (attention) towards the stimulus source facilitating an early visual perceptual extraction of relational information and subsequently facilitating the processing of relevant information and the selection of appropriate responses. In short, the primary function of orienting is to prepare the organism to deal effectively with the novel/deviant stimulus.

The sudden inhibition (interruption) of movement(s), which takes place as a result to (suddenly) orienting in an otherwise well predicted and/or expected temporal sequence of imminent ballistic movements in reachable space (egocentric space), has been shown to enhance early perceptual processes, if the orientating (by the subject) synchronizes with mechanical physiological activity in general, and cardio-respiratory phases in particular. In other words, a mentally explicit cognitive mapping about time discreteness appropriately surfaces while the organism non-cognitively is orienting towards novel/deviant stimuli in a (visual) sequential stimuli array. More so, the magnitude of this physiological timing effect is larger for rare (variable stimuli) than frequent (constant) stimuli, suggesting the importance of stimulus significance (Steinhauer et al., 1992). More so, a landmark article of Graham and Clifton (Graham, F. K., & Clifton, R. K. 1966. Heart-rate change as a component of the orienting response. Phschological bulletin, 65, 305-320) related orienting to heart rate (HR) via the intake (extraction)/rejection (processing) hypothesis proposed by the Laceys (Lacey, J. I., Ragan, J., Lacey, B. C., & Moss, H. A. (1963). The visceral level: Situational determinants and behavioral correlates of autonomic patterns. In P. H. Knapp (Ed.), *Expression of Emotions in Man.* New York: Internaional Universities Press). This hypothesis assumes that extraction (intake) of sensory (visual) information by a (early-visual) perceptual act is facilitated by deceleration of HR whereas processing of sensorial information (rejection) is facilitated by (visual) ordinary perception via acceleration of HR.

The teachings of the present invention strongly suggest that early visual perceptual acts, which effectively orient to novel stimulus from an intrinsic variable sensory (visual) sequential stimuli source, will elicit in the first place a strong multiple connection between mentally cognitive behavioral plans (in allocentric space), triggering imminent ballistic movements (in egocentric reachable space) and autonomic effectors (in visceral space). In other words, the apparatus and method of the present invention aims to integrate and transform various information sources about egocentric spaces via early visual perceptual acts, as triggering and guiding imminent ballistic motor movements in the subjects reachable space, while the perceiver mentally attains an explicit cognitive representation of time durations among the very same executed sequential imminent ballistics movements, in reachable space.

It becomes clear that the present invention aims fusing together multiple sources of information concerning egocentric spaces, into one grand source. Such grand unification is necessary in order for the perceiver to accomplish a vigorous early perceptual representation of a single and robust sensorimotor space (egocentric space), such that the later dominant visual ventral system doesn't commit cognitive resources to patched up for missing informational gaps caused by a faulty developmental early perceptual visual awareness of egocentric space. Thus, constantly weakening egocentric space.

The integration of egocentric information also translates into an economy of cognitive resources, which will be exploited later by a faster processing of information in the visual ventral stream. An economic information processing leads to a rapid and less unbiased representation of a cognitive space, so that recognition and categorization of objects in allocentric space is immediate (within the capacity of working memory).

The teachings of the present invention as herein implemented in an embodiment, aim in general, to facilitate the developmental perceptual internalization of 'time' by triggering early visual perceptual motor loops processes, which in part are being corroborated by special functions localized in the cerebellum. Ontological development in the very beginning, takes upon the perceptual internalization of "time discreetness" via early perception-motor loops, were the inner tempo for executing sequential imminent ballistic movements of such perceptual-motor loops is being rehearsed and provided by specific functions in the cerebellum. Subsequently, the perceptual internalization of the arrow of time ends with cognitively representing "standard time", via explicit ordinary sensorial perception. In particular, we herein have conceptualized visual perception as being a modular and integrative process consisting of two gross stages: 1) The perceiver actively engages in early visual perceptual-loops acts, and directly attained relational information, which was implicitly extracted from a intrinsic variable simple optical flow field. The implicit extracted information effortlessly transforms into an explicit mental mapping of time discreetness, whilst (the perceiver) executes sequential imminent ballistic movements in reachable space planned and rehearsed by specific areas in the cerebellum; 2) the perceiver, via visual ordinary perception, commits his/her cognitive resources to construct objects and subsequently categorize those objects in a 3D space. The perceiver accomplishes such cognitive constructions by establishing causal relationships among other constructed objects in 3D space. The resulting constructed metrics (of allocentric space) will attain an stability per se, if and only, the perceiver will be successful in explicitly represent the meaning of the passage of time at large; that is, attaining an ordinary perceptual internalization of the arrow of time connecting a present event as consequence of a past event.

The ordinary perceptual internalization of 'time' generates an explicit representation, a sort of a cognitive mental template on which visual ordinary perception can assemble the present processed status of a 3D object(s) in mental cognitive space. Such a visual ordinary perceptual mapping enables the cognitive processing of an object features details including size, color, and shape. In conclusion, the development of normal ordinary perception depends in a great degree upon the perceiver's cognitive ability of attaining an explicit mental representation of the arrow of time, that is, an explicit mental representation about the flow of time as streaming from the present to the past.

We have centered on several hypotheses connecting dyslexia to a biological level of causation. We have also presented overwhelming evidence for a magnocellular deficit and/or mild cerebellar impairment and/or an early visual perceptual deficit, (second core deficit) which according to the teachings of the present invention, should all be considered as potential physiological-perceptual/cognitive suspects for causing a diminished implicit perceptual-motor representation of space, namely egocentric space, in children suffering from dyslexia but also from other learning difficulties.

In general, we expect that such a feeble early perceptual-motor representation of space, will inevitably turn into a weak implicit awareness of egocentric space in children, and only a mild compensation for such early perceptual-motor deficit will be available during adult life, due to new developed cognitive strategies.

Lastly, we have hypothesized and argued for an early visual perceptual-motor deficiency (especially during young age) corroborated by a cerebellar weakness, to blame for failure to explicitly generating a mental representation of time discreteness. Such early visual perceptual-motor deficiency hinders the perceiver's potential for executing fluent ballistics movements in his/her reachable space. More so, dyslexia is a biological and/or perceptual deficiency that disrupts normal development in early life, but only quantified as soon as the child encounters difficulties in literacy skills (ages 6-8 years old). Undermines the individual's achievements tearing down his/her self-confidence thus, also impinging a negative behavioral mark during adult life.

The teachings of the present invention also envision dyslexia as been the cause for constraining visual ordinary perception from grasping a common sense representation of cognitive space (allocentric space) and thus, impairing the subject's ability of properly recognizing objects in allocentric space.

It is with little doubt we conclude that literacy skills, which depend on cognitive faculties (including discrimination and categorization of sensorial stimuli), will be dramatically affected and distorted. Hence, inevitably impacting reading, which is by far the most common reported symptom in developmental dyslexia.

Figure 1:
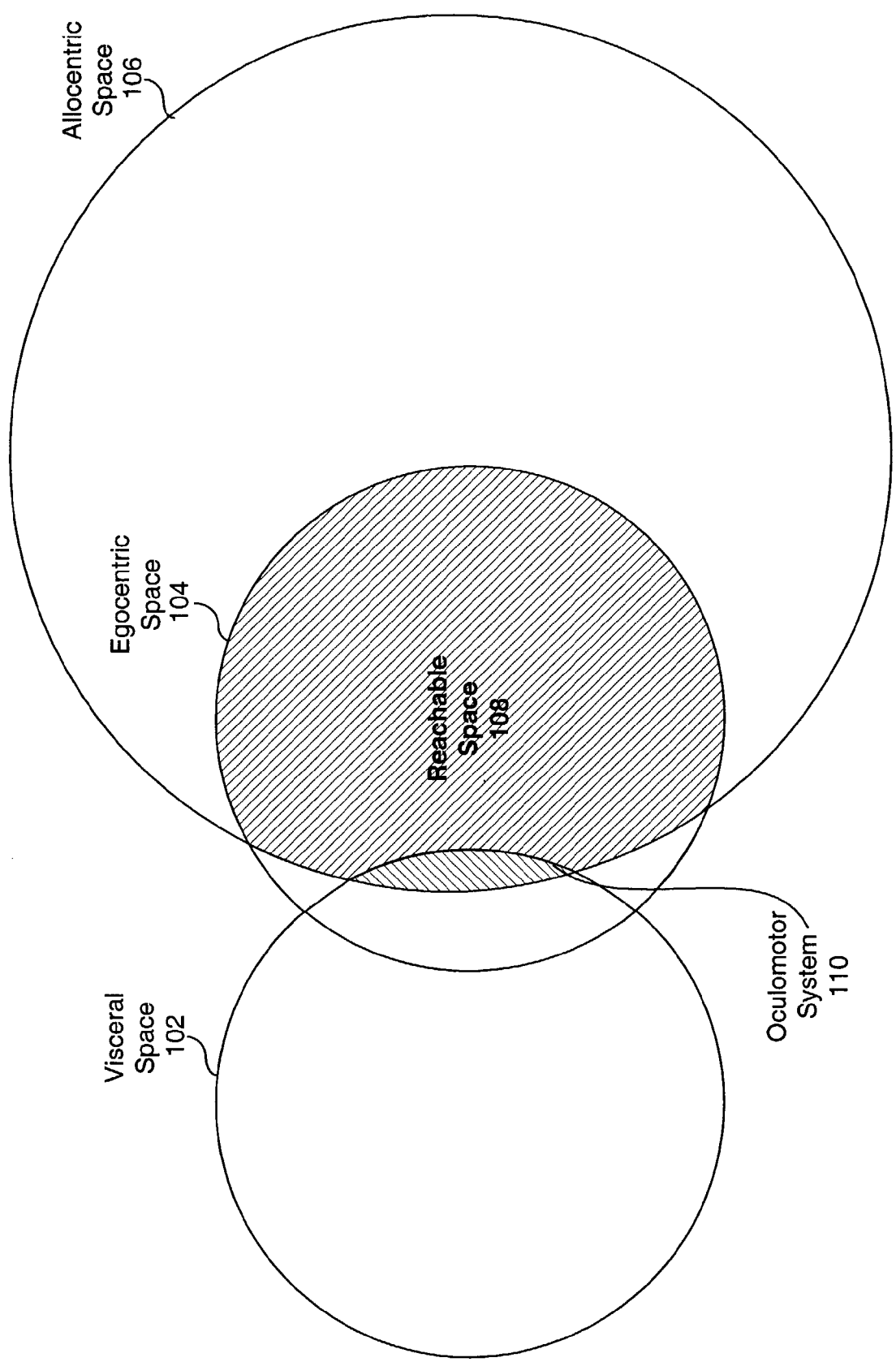
FIG. 1 illustrates three types of space inherent in all humans, including visceral space, egocentric space and allocentric space according to an embodiment of the present invention.

3. Overview of Invention 3.1. Visceral/Egocentric/Allocentric Space of a Subject FIG. 1 illustrates three types of space inherent in all humans, including visceral space 102, egocentric space 104 (related to early visual perception) and allocentric space 106 (related to ordinary visual perception). Allocentric space 106 embraces or overlaps the outer limits of egocentric space 104. This overlap between egocentric space 104 and allocentric space 106 is referred to as reachable space 108. The overlap between visceral space 102, egocentric space 104, and allocentric space 106 is referred to as the oculomotor system 110. Next, visceral space 102, egocentric space 104, allocentric space 106, reachable space 108 and the oculomotor system 110 will be described in more detail.

3.1.1. Visceral Space

Visceral space 102 relates to a domain involving physiological activities within a subject that have an intrinsic temporal variability in their cycles. Such physiological activities in visceral space 102 include, but are not limited to, hormonal cycles, the breathing cycle, the heart cycle, most neurological activity, and so forth. Another common trait of the physiological activities in visceral space 102 is the autonomous and automatic nature of the activity, where the activity happens without any attention or cognitive participation on behalf of the subject. In fact, physiological activities automatically occur in a species. The present invention is mostly concerned about physiological mechanical activity in visceral space 102, including, but not limited to, the mechanical activity of the heart, lungs, eye blinking and digestive system.

3.1.2 Egocentric Space

Egocentric space 104 reflects the implicit capacity of the subject's body for integrating and transforming several sources of body centered information (e.g. proprioceptive, vestibular and visual) to guide imminent motor behavior. In egocentric space 104, the early visually perceived kinematical trajectories of "things" are viewed as being in a direct one to one radial relationship with the perceiver.

As mentioned above, egocentric space 104 is related to early visual perception in the subject. An early visual perceptual mapping of egocentric space 104 in the subject translates (directly) in the perceiver into "imminent action." Therefore, the kinematical trajectories of early visually perceived things do not possess an intrinsic detailed status in their own right. Hence, the early visually perceived kinematical trajectories of things in egocentric space 104 cannot afford to be visually discriminated or verbally categorized as objects. In other words, the perceiver cannot establish verbal relationships among early visually perceived kinematical trajectories of things in egocentric space 104, other than to become an unconscious active performer of the very early visually perceived kinematical movements himself. Thus, the early visual mapping of egocentric space 104 triggers in the perceiver imminent ballistic movements activity. Therefore, egocentric space 104 herein refers to an active perceptual sensorimotor mapping of space within the perceiver's reachable space 108.

Magnocellular neuron cells in retinocortical and retinosubcortical dorsal pathways of the subject extract relational information from transient stimuli about visual motion perception to guide motor behavior in the perceiver's reachable space 108. Movements in egocentric space 104 are herein referred to as ballistic or imminent movements that take place in the perceiver's reachable space 108. Reachable space 108 may be viewed as being populated by a multidimensional dynamical web of potential ballistic movements that are mainly actualized and executed by body parts (e.g., fingers, wrist, hand, arm, head, eyes, neck, and so fourth), principally in the upper section of the subject's body.

Early visual perception of stimuli attributes within egocentric space 104 triggers imminent action in the perceiver, which are also automatic and imply early perceptual motor loops. Movements in egocentric space 104, once underway, cannot be consciously aborted, delayed or inhibited. In addition, movements executed in egocentric space 104 are characterized by not being ordinarily perceived by any other observer as if convening any message, that is, ballistic sensorimotor activity in egocentric space 104 is not a communicatory act.

The early visual perception of egocentric space 104 triggers in the perceiver, imminent ballistic movements activity, followed by separate or joint ballistic movements of mechanical nature done by various body parts in a non-voluntary, unconscious feedforward interaction with those early visually perceived things in reachable space 108. The actualization of executed imminent movements by the subject is always a sub-set of a much larger potential web of kinematical trajectories, namely egocentric space 104. These body parts principally include those in the upper extremities, waist, neck and the oculomotor system 110 (FIG. 1).

3.1.2 Allocentric Space

Allocentric space 106 refers to a cognitive (mental) mapping of space at large and is related to visual ordinary perception. Here, motor actions executed in allocentric space 106 (e.g., speech, body gestures, pointing with arm and/or finger, and so forth) convey a message to other observers and thus are perceptually considered a communicatory act. Communicatory acts are acts or actions that can be inhibited, that is, actions that can be delayed or aborted all together by the subject. Ordinary visual perception takes place in all allocentric space 106, which captures and organizes the explicit intent or meaning (and/or unconscious intent) of actions. Hence, sequential movements executed by the subject are clearly parcel into discriminable sets of subject actions, which are then further categorized in language.

In allocentric space 106, parvocellular cells in the ventral neuropathway of visuocortical areas of the subject, process detailed information concerned with object features (e.g., color, size, shape, etc.), including the relative location of one object with respect to another. With humans, object recognition together with its relative coordinates in allocentric space 106 are registered in memory storage, which are later accessed in order to provide a verbal report about the results of its analysis. Visual object recognition and its categorization in allocentric space 106 are strongly distorted in humans by endogenous influences including, but not limited to, intention, expectations, attention and learning.

3.2 Interaction of a Light Array and the Subject

Figure 2:
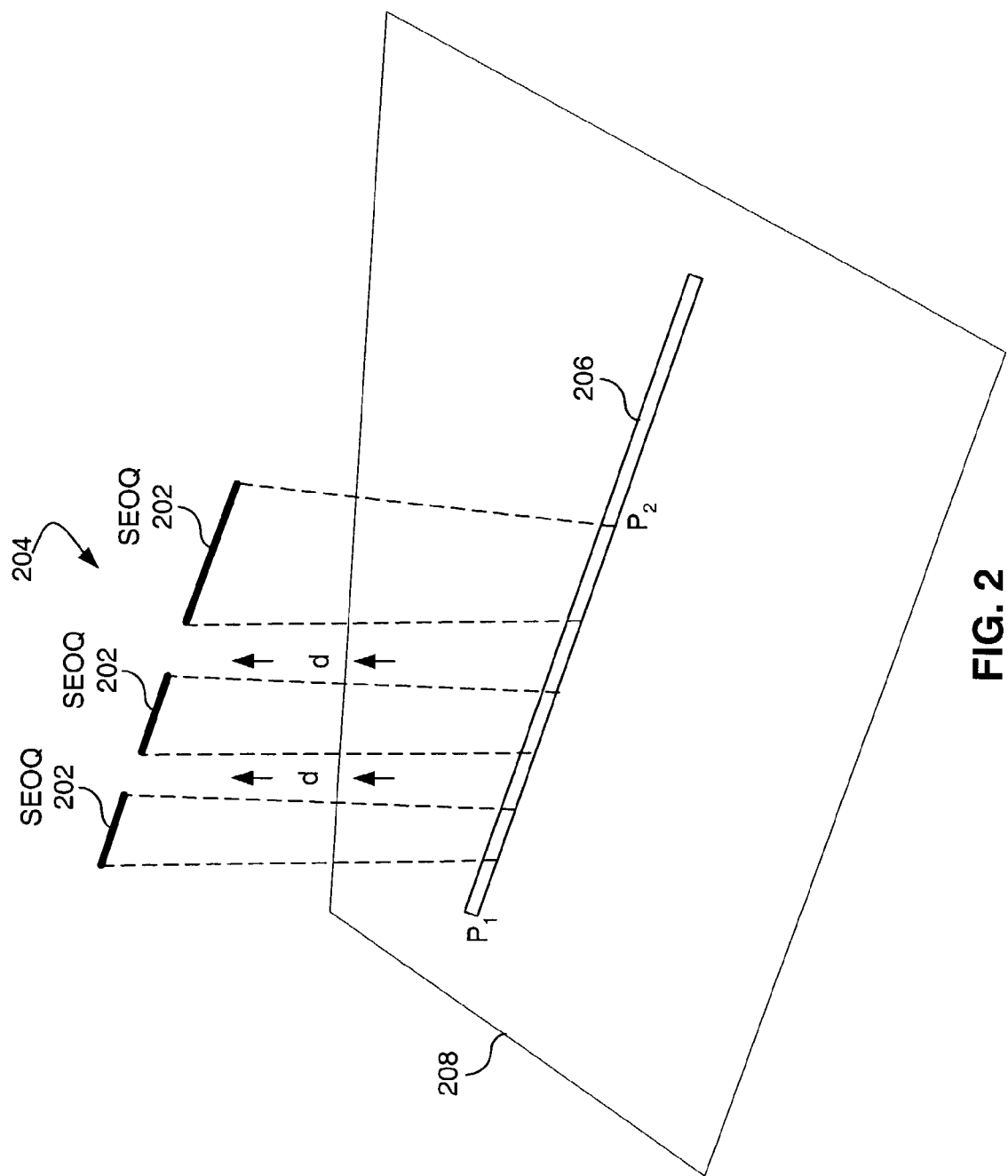
FIG. 2 illustrates a general case for the formation of a single light array according to an embodiment of the present invention.

Optical quanta involved with the apparatus and method of this invention is not defined or considered herein to be only inside the human's perceptual visible light spectrum, but also extending towards the infrared and ultraviolet spectral regions of the visible light spectrum. A general case for the formation of a single light array 204, is shown in FIG. 2. This general case for the formation of single light array 204 is described in order to facilitate the understanding how an optical field in FIG. 3 may be implemented.

In FIG. 2, three sets of energetic optical quanta (SEOQ) 202 make up light array 204 as it emerges through a slit 206 on a plane or surface 208. As light array 204 moves at the speed of light in a medium M, light array 204 is (informatically) considered to be constant or as having a defined informational identity only during a certain specific time interval ▲t. Changes at light source level and/or in the medium M (e.g., turbulence) will produce changes in the SEOQ 202 (probably at some locations but not in others along the p1 and/or p2 sides of slit 206). FIG. 2 also shows the general direction d of the photons of light and the specific spatial distribution of the three SEOQ 202 along slit 206, causing light array 204 to remain informatically the same during a certain interval ▲t. The graphical planar projection of the three SEOQ shown in FIG. 2 is shown only for example and is not intended to limit the spatial configuration of a light array in the present invention.

Figure 3:
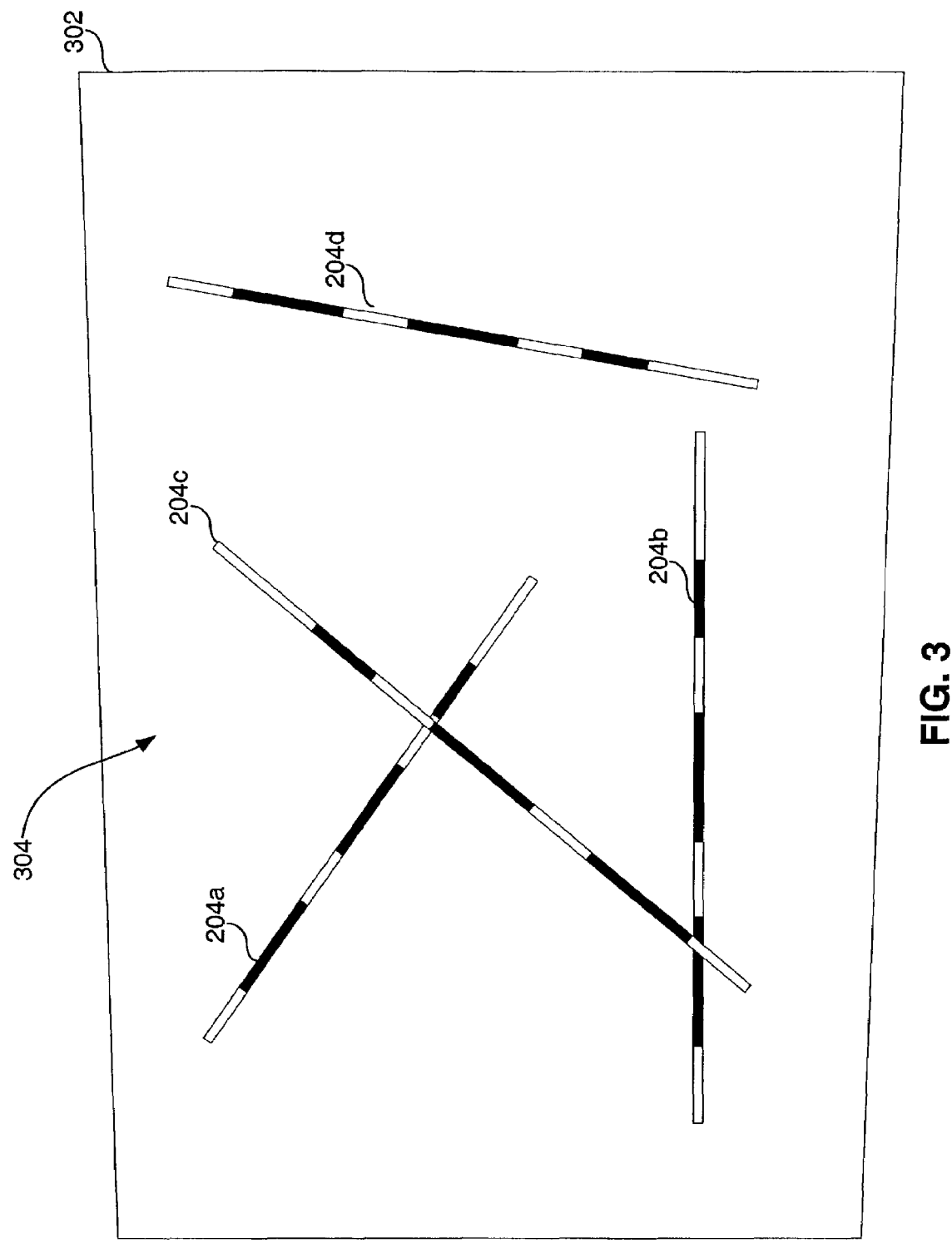
FIG. 3 shows an example plurality of single light arrays emerging through a surface according to an embodiment of the present invention.

FIG. 3 shows a plurality of single light arrays (204a, 204b, 204c and 204d) emerging through surface 302. This plurality of lights arrays is herein considered to form an optical field (OF) 304. As discussed above, only through a time interval ▲t can optical field 304 possess a particular informational identity. Optical field 304 is not perceivable by a human subject until it impacts the retina of the subject, at which point it becomes an optical image (OI). If the interval ▲t is long enough, optical field 304 and optical image will be considered as remaining informatically constant.

SEOQ 202, light array 204, optical field 304 and optical image are considered to take place naturally outside the realm of human perception, and do not perceptually affect the human subject. Optical field 304 could be also generated by a light source reflecting the three SEOQ 202 on a surface or generated by a computer screen display. Optical field 304 as shown in FIG. 3 is for illustration purposes only and is not intended to limit the invention.

Figure 4:
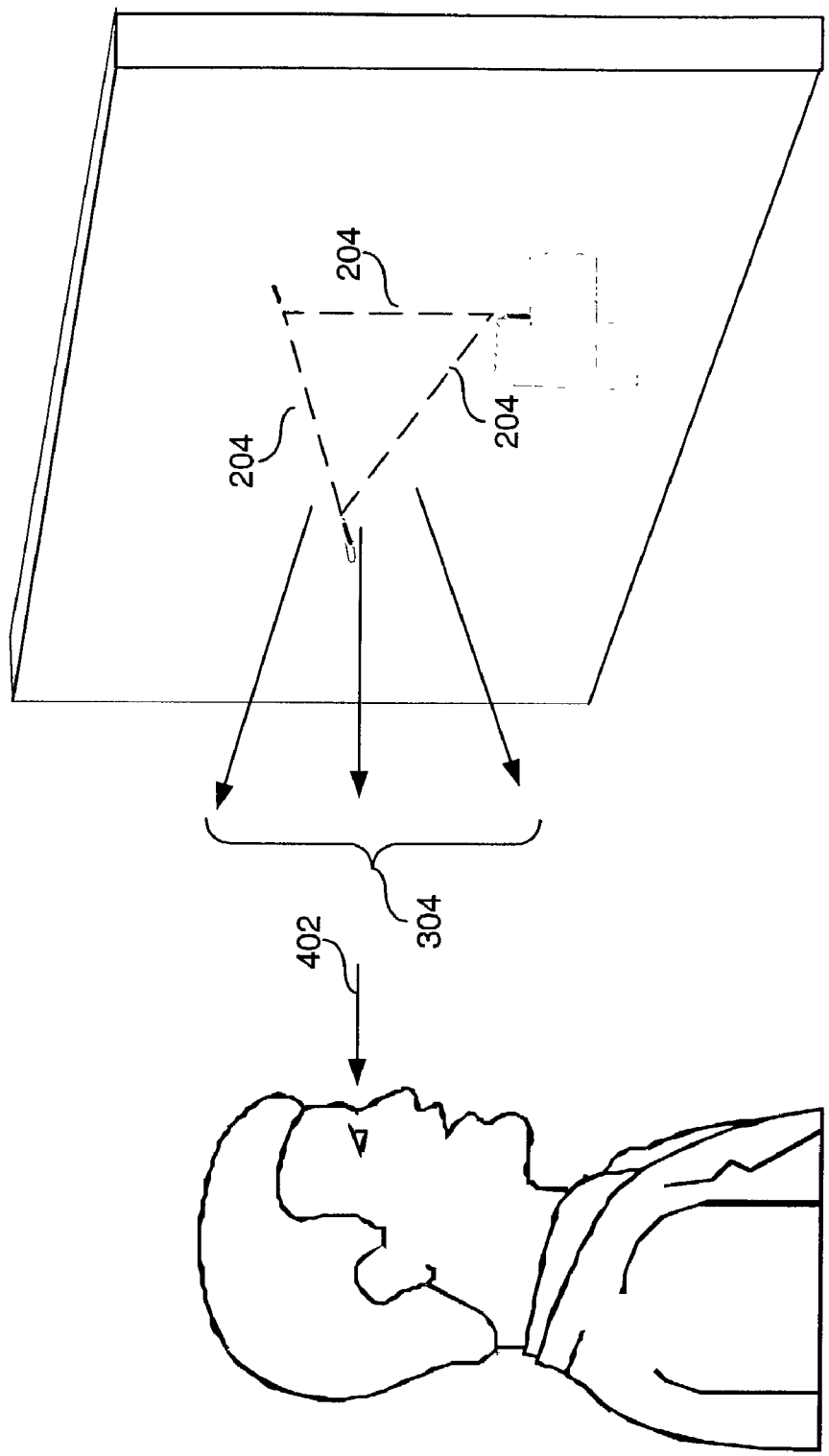
FIG. 4 shows the eyes of a human perceiver intercepting the path of light from an optical field according to an embodiment of the present invention.

FIG. 4 shows the eyes of a human perceiver intercepting the path of light from optical field 304 (FIG. 3). In almost no time (due to the speed of light), a defined optical image 402 will project on the surface of the retina of the perceiver, which may remain there for an interval ▲t.

Considering an extreme case were the light source is at rest in relation to the perceiver's body, and that the perceiver has intentionally managed to immobilize all his/her body parts, it will still not be possible to avoid the intrinsic mechanical influence of involuntary systems in visceral space 102 (the human body) by which one or more of at least the oculomotor system 110, neck and waist will bring about complex movements of the eye and the retina in relation to the light sources generating the optical field 304. As a result, the projected optical image 402 of the optical field 304 will fluctuate, that is, it will keep moving on the retina surface. This intrinsically unavoidable non-stationary condition of any optical image 402 on the retina surface will generate an optical flow (OF) even if both the light source of the optical image 402 will remain at rest and the human perceiver will maximally refrain from moving.

The generated optical flow is characterized by a plurality of light arrays 204, which move in all possible directions in 3-dimensional space, such that optical flow comprises a complex or absolute (global) optical flow field. The nature of ambient light arrays 204 is such that optical image 402 (even if it fluctuates due to unavoidable intrinsic mechanical influences of involuntary systems in visceral space 102) will still be bias towards inhibiting the potential for triggering imminent ballistic movements in reachable space 108 of the subject. Complex optical flow fields favor motor quasi-stationary states for considerable periods of time (e.g., a few seconds) in the body upon imminent ballistic actions (e.g., the case in the oculomotor system 110 which immobilizes the eyes in average, for almost 90% of the time in every second). The latter is no coincidence but reflects the existing delicate dynamical balance between egocentric and allocentric visual perception of space. In the case of the oculomotor system 110, both eyes expend almost their entire time in a quasi-stationary state, such that enough time is available for the deployment of attention mechanisms that will guarantee via ordinary perception the processing of visual information from a visual scene principally by the parvocellular system in order to attain a stable cognitive representation of allocentric space.

However, by far, most of the retina surface is related to the magnocellular system. Therefore, this basal complex optical flow field, which grants effortlessly a maximal and effective detection of a 3-dimensional space, will introduce photic related fluctuations in the retina that trigger magnocellular reactivity when either (1) the subject is in a state of self-motion and the environment is at rest, or (2) when the subject is at rest and objects in the environment perceptually move towards or away from him/her. In contradistinction, only a minimal part of the retina surface, the fovea, requires a quasi-stationary state of the oculomotor system 110 in order to process information from the optical image 402. The fovea is related to the Parvocellular system. The relative small foveal zone against the large peripheral zone of the retina will be described below with reference to FIG. 6.

As indicated above, the optical image 402 is of a physical nature, the kind obtained with a photographic camera. The intrinsic dynamic nature of optical image 402 when making physical contact with the eyes of a human perceiver gives birth to a new kind of an optical image 402, herein called biological optical image (BOI), from where human visual perception phenomena has its origin. Energetic optical events and early perceptual optical events are discussed next.

3.3. Energetic Optical Events (EOE) and Early Perceptual Optical Events (EPOE)

Figure 5:
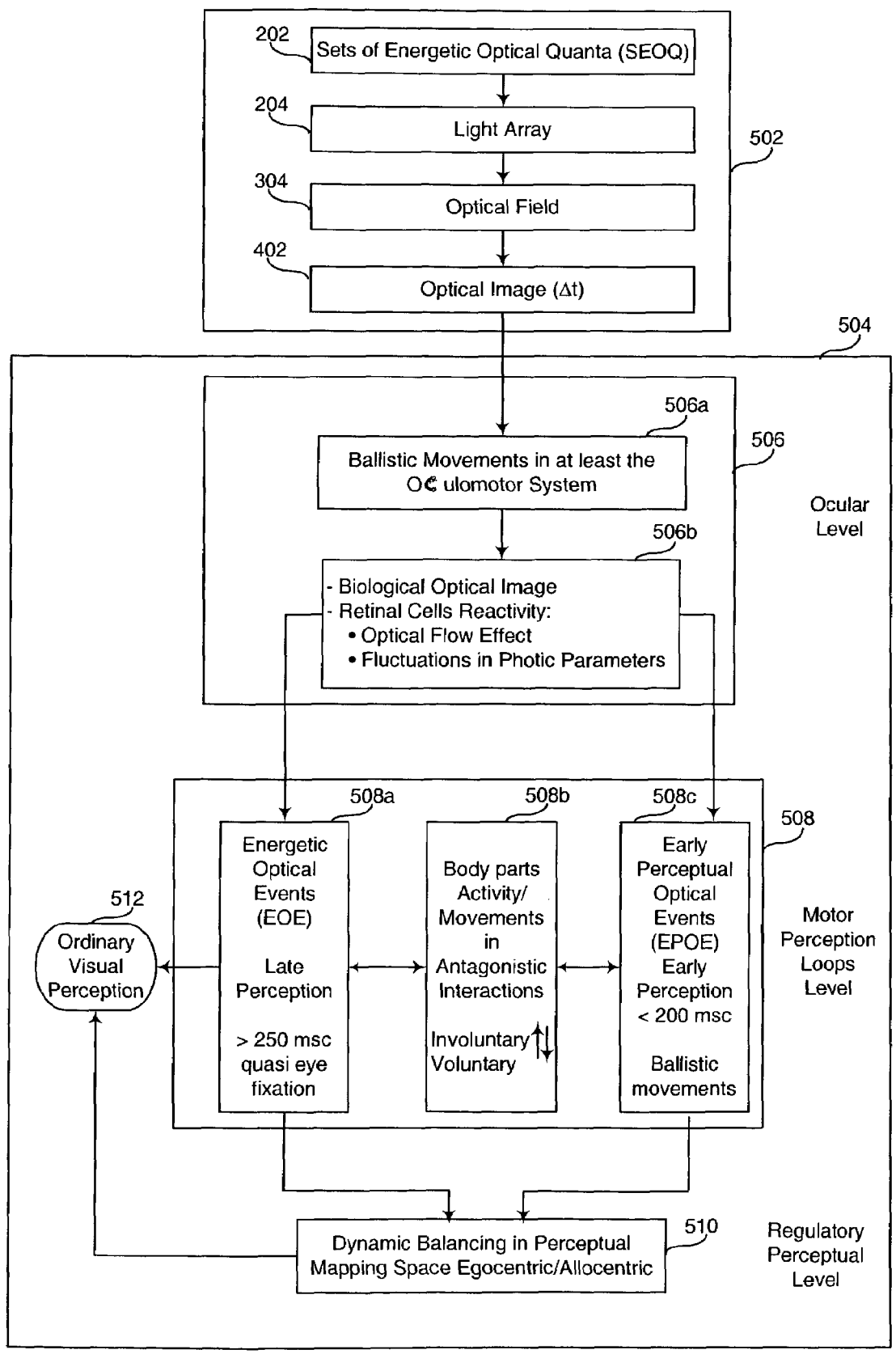
FIG. 5 illustrates a high level overview of the present invention according to an embodiment.

FIG. 5 illustrates a high level overview of the present invention. The overview includes step 502 where the invention generates optical image 402 (FIG. 4) and step 504 where the invention aims to influence the visual ordinary perception of a human subject in the desired direction. The invention also aims to infuluence processes in a subject or perceiver at various levels to induce an overall perceptual-motor integration in the subject via optical image 402.

As described above with reference to FIGS. 2-4, step 502 includes modulating sets of energetic optical quanta (SEOQ) 202 to create light array 204. A plurality of light arrays 204 form the optical field 304. Once optical field 304 impacts the retina of the subject, optical field 304 becomes optical image 402. As mentioned above, SEOQ 202, light array 204, optical field 304 and optical image 402 are considered to take place naturally outside the realm of human perception and are used to influence the ordinary visual perception of a human subject, in the desired direction.

In step 504, the invention aims to influence processes in the subject or perceiver (via optical image 402) at various levels to induce an overall perceptual-motor integration in the subject so as to induce the desired changes at ordinary visual perception 512. The various levels include an ocular level 506, a motor perception level 508 and a regulatory perceptual level 510. Each of these levels is briefly introduced next and described in more detail below.

In ocular level 506, optical image 402 creates ballistic movements in at least the oculomotor system of the subject in step 506a. In step 506b, these ballistic movements caused by the intrinsic dynamic nature of optical image 402 when making physical contact with the eyes of the human perceiver, gives birth to a new kind of an optical image 402, herein called biological optical image (BOI). It is from the biological optical image where human perception phenomena has its origin. Here, retinal cells reactivity within the subject is caused by the optical flow effect and fluctuation in photic parameters. Ocular level 506 is described in more detail below with reference to FIG. 6.

In motor perception level 508, energetic optical events (EOE) are considered to occur in more than 250 milliseconds and are considered to mediate a part of allocentric space 106 (FIG. 1). EOE are related to late ordinary perception of the subject and require quasi eye fixation of the subject. The invention uses EOE to facilitate voluntary body parts activity in the subject in step 508*b*. Early perceptual optical events (EPOE) in step 508*c* are considered to occur in less than 200 milliseconds and are considered to mediate a part of egocentric space 104 (FIG. 1). EPOE are related to early visual perception of the subject and trigger ballistic movements in the subject. The invention uses EPOE to trigger involuntary body parts movement in the subject in step 508*b*.

In regulatory perceptual level 510, by presenting EOE and EPOE to the subject at the motor perception level 508 establishes in the subject a dynamic balance in visually perceptual mapping space between egocentric space 104 and allocentric space 106. Ocular level 506 is described next in more detail with reference to FIG. 6.

3.3.1. Ocular Level

Ocular level 506 is further described with reference to FIG. 6. FIG. 6 illustrates an example of a single light array 204 (FIG. 2) from an optical field 304 (FIG. 3) and how it interacts with eye 602 of a subject. Eye 602 represents the physical location of the perceptual visual field of the subject. The perceptual visual field of the subject branches into an early perceptual visual field and an ordinary perceptual visual field. Eye 602 is comprised of many parts including retina 604, iris 608, lens 610, pupil 612 and cornea 614. Retina 604 is comprised of peripheral 605 and fovea 606. Peripheral 605 is neurophysiologically closely connected to egocentric space 104 (FIG. 1), whereas fovea 606 is neurophysiologically more closely connected to allocentric space 106 (FIG. 1).

Retina 604 is covered with light-sensitive receptors called cones and rods. Rods are focused in the peripheral 605, whereas cones are focused in fovea 606. Rods are primarily for night vision and for visually perceiving movement; they are sensitive to a broad spectrum of light; they can't discriminate between colors; they are sensitive to light intensity or shades of gray; and they detect motion of threats in periphery of the subject. Rods are more functionally focused in egocentric space 104 and the early perceptual visual field of the subject. Cones are used to visually sense color and allow for high acuity of objects focused at fovea 606. Cones are more functionally focused in allocentric space 106 and the ordinary perceptual visual field of the subject.

Also physically and functionally focused in peripheral 605 are magnocellular cells. Magnocellular cells are very sensitive to motion. Thus, magnocellular cells grant a subject's early visual-sensory motor perception. Early visual-sensory motor perception provides direct information about where things are in relation to the perceiver, namely an egocentric spatial early perception, but not what things look like. Visual motion information extraction takes place in the retinocortical and retinal sub-cortical dorsal neural pathway in the brain due to specific receptive field qualities of the magnocellular cells.

The three SEOQ 202 (FIG. 2) shown in FIG. 6 trigger different types of visual phenomena depending on the retinal zone they finally reach. These different neuronal reactions are mainly linked to the presence of two very different kinds of neural cells (magnocellular and parvocellular), which are highly non-evenly distributed on the surface of retina 604.

Unlike physical optical images, and as explained above, biological optical images generated at ocular level 506 are of an intrinsic dynamic nature, obtained with the participation of many biological structures and intrinsic variable functions in the human body. And, most importantly, two different time domains should be considered (<200 milliseconds and >250 milliseconds) to understand the genesis of two different orders of perception as briefly described at steps 508*c* and 508*a* respectively (FIG. 5). The dynamical interactions between the two different time domains bring about an overall perceptual-motor integration in the subject's body. Such perceptual-motor integration grants the subject the normal attainment of ordinary visual perception of space, and also the discrimination, categorization and analysis of such a visual representation of space, via verbal report.

The single light array 204 shown in FIG. 6 is an example derived from FIG. 2, with three SEOQ 202 taking place during the same time interval ▲t. Time required for this light array 204 to be projected on the surface of retina 604 is insignificant in relation to this ▲t interval due to the high speed of light. Thus, FIG. 6 illustrates a retinal projection of only one component of optical field 304, schematically showing the projected extremes of single light array 204. Even if optical field 304 will remain at rest in relation to the head of the perceiver, the position of the projected extremes q1 and q2 will fluctuate to, for example, points q'1 and q'2 in the peripheral retina, as shown in FIG. 6. As explained earlier, this phenomenon is a consequence of various intrinsic mechanical fluctuations in visceral space 102, such as ballistic movements in the body, including those of the oculomotor system 110.

The biological optical image is characterized by intrinsic spatiotemporal fluctuations originating from the subject. Such spatiotemporal fluctuations can be considered to be velocity vectors in the retinal projection of the external physical optical image. During the natural execution of saccades (ballistic oculomotor movements) the spatiotemporal fluctuations take place in around 25-30 milliseconds each.

The roots of normal early visual perception may lie in the presence of these velocity vectors in the peripheral 605 of the retina 604. This natural mechanism provides for a chronic triggering process of magnocellular reactivity. It is known that transient changes in certain photic parameters will trigger pre-attentive cuing and/or magnocellular reactivity.

One main objective of the present invention is to technologically produce and generate an intrinsic variable visual dynamic environment. Such particular visual environment will comprise velocity vectors such that a complex optical flow field could be constrained to a simple optical flow field. In such a simple optical flow field, the subject will visually experience motion perception as if passing by him/her (e.g. translational and laminar motion) instead of away or towards him/her. In such a simple optical flow field the oculomotor system 110 will be at times busy perusing (tracking) perceptual visual indicia (targets and distractors) thus, the eyes constantly exercising a state of smooth pursue along the visual scene.

Another objective of the present invention is to technologically trigger pre-attentive cuing and/or magnocellular reactivity by resorting to the above-mentioned intrinsic spatiotemporal fluctuations. The present invention aims to generate and trigger such spatiotemporal fluctuations in such magnitudes as if compensating for the body's inefficiency in naturally and intrinsically triggering ballistic movements in egocentric space, as described below with reference to FIGS. 7 and 8. Motor perception level 508 is described next in more detail.

3.3.2. Motor Perception Loop Level

Two orders of visual perceptions are generated by a biological optical image, including (1) an early visual motor perception taking place in about <200 milliseconds (EPOE); and (2) a late ordinary visual perception taking place in about >250 milliseconds (EOE). The present invention provides for means and methods to produce sets of energetical optical quanta (SEOQ) 202 (FIG. 2) in optical arrays 204 and changes of these SEOQ 202 in optical arrays, all of which are herein defined as optical events. In this invention, optical field 304 is populated with early perceptual optical events (EPOE) to facilitate pre-attentive cuing and magnocellular reactivity towards transient stimuli in order to trigger egocentric imminent ballistic motoric movements in the subject. (This is illustrated in step 508c in FIG. 5.) Optical field 304 also includes energetic optical events (EOE) to facilitate ordinary visual perception of an allocentric space and parvocellular activity. (This is illustrated in step 508a in FIG. 5.) Antagonistic Movement's interaction in step 508b is now described.

The spatiotemporal structure of a natural optical field 304 may lack, at certain unpredictable periods of time, the sufficient order of variability required to leap above a biological desirable threshold and transform optical field 304 into a biological optical image. It is the biological optical image that may induce the required transient temporal resolution (quick temporal changes) in peripheral 605. As a consequence, ground magnocellular reactivity and the potential for triggering imminent ballistic movements in reachable space 108 (FIG. 1) of the subject (via early visual motor perception) could be compromised. Hence, the dynamical balance between the potential for triggering imminent ballistic movements in egocentric space 104 (that will cause optical images 402 to intrinsically fluctuate in retina 604) and holding the eye 602 in a quasi-stationary fixation state (by means of (intentional) restricted movements of body parts) long enough for the eye to focus on allocentric space 106 (in the small area of the fovea), may be imperative if nature is to secure the attainment of ordinary visual perception.

In normal subjects, this delicate balance between antagonistic types of movements/actions has been achieved with an unconscious, non-voluntary performance of an average of three ballistic saccades per second. Each ballistic movement of the eye 602 lasts approximately 30 milliseconds. Between saccades the eye 602 is maintained in a quasi-stationary fixation state to secure the focus of an image on the fovea 606. In this way, quasi-stationary intervals of about 300 milliseconds will allow for parvocellular activity in the fovea 606, immediately followed by ballistic motor periods of about 30 milliseconds to sustain basic and normal magnocellular reactivity in the peripheral 605.

Nevertheless, this natural visual perceptual-motor biological balance in humans is very sensitive due to the influence of many variables. If a task demands a higher focus of attention of the subject, then the quasi-stationary fixation state of the eye 602 may be extended until 500 milliseconds, for example, then we are left with the possibility of less than two saccades per second, a situation that may inevitably hinder early sensory motor perception. On the other extreme we may have a condition where the subject imminently executes an average of four or more saccades per second. In this case we will have on average many fixation periods lasting less than 200 milliseconds. In this particular case, there is not enough time for the deployment of focused attention to serially search the visual scene and allow the processing of perceptually selected image information reaching the fovea 606. In general, ordinary visual perception will be very difficult to achieve if the visual task at hand requires an average of long time eye fixations, as is the case for dyslexic people when they are confronted with the task of reading.

The kind of relationship between egocentric and allocentric mapping of space activity in the subject in step 510 (FIG. 5) is considered herein as a dynamic balance, which together with the above indicated two orders of visual perceptions, defines the actual condition of ordinary visual perception 512. Ordinary visual perception 512 in itself is bound to fluctuate in accordance with the visual task at hand, factors affecting the two above mentioned orders of visual perception, and also the dynamic balance established between egocentric and allocentric activity. A goal of the present invention is to shift the established egocentric/allocentric dynamic balance in the subject by controlling early perceptual optical events and energetic optical events in optical field 304 that is provided to the subject, as described next with reference to FIGS. 7 and 8.

In step 702 of FIG. 7, photic energetic parameters of a light array and photic early perceptual attributes of the light array are controlled to trigger pre-attentive cueing and/or increase sensitivity of magnocellular reactivity towards visual transient stimuli in a subject. Control then passes to optical field 304.

In step 704, an optical field 304 is modulated based on the photic energetic parameters and the photic early perceptual attributes so that the optical field 304 transforms into the perceptual visual field of the subject the moment it makes physical contact with the subject's retina. The perceptual visual field includes the early and ordinary perceptual visual field of the subject. The flowchart in FIG. 7 ends at this point.

FIG. 8 illustrates in a different way than in FIG. 7, how the present invention controls photic energetic parameters and photic early perceptual attributes of the light array 204 to trigger pre-attentive cuing and/or increase sensitivity of magnocellular reactivity towards transient visual stimuli in a subject. Here, the invention controls photic energetic parameters 804 and photic perceptual attributes 806 in the optical image 402 (produced in step 502 and described with reference to FIG. 5 above) to produce the controlled generation 808 of early perceptual optical events and energetic optical events. This controlled generation 808 aims to influence processes in a subject or perceiver at various levels to induce an overall perceptual-motor integration in the subject's body via optical image 402 (as produced in step 504 and also described with reference to FIG. 5 above). The system architecture of the invention is described next.

4. System Architecture Overview

FIG. 9 is a block diagram representing an example system environment of the present invention. Referring to FIG. 9, a physiological mechanical activity sensor module 902 (hereafter sensor module 902), an optical events stimuli module 904 (hereafter optical events module 904), an optical field stimuli output module 906 (hereafter optical field output 906), a game/entertainment program module 908 (hereafter game 908) and a subject 910 are shown.

At a high level, sensor module 902 monitors the physiological mechanical activity of subject 910 and receives signals regarding particular physiological mechanical activity it is monitoring. Sensor module 902 processes, preferably in real time (although the invention is not limited to real time processing), the physiological mechanical activity signals to derive the necessary information used by optical events module 904. Optical events module 904 receives this information from sensor module 902 and identifies a program for subject 910 that will trigger pre-attentive cuing and/or increase sensitivity of magnocellular reactivity in subject 910. Optical events module 904 involves controlling photic energetic parameters and photic early perceptual attributes that will determine both spatial and temporal fluctuations of light arrays 204 that are generated and outputted by optical field output 906. Optical events module 904 also receives information from game 908 which may alter the program for subject 910. Thus, based on the controls or program determined by optical events module 904, optical field output 906 and game 908 trigger pre-attentive cuing and/or increases sensitivity of magnocellular reactivity in subject 910. Next, each of these modules is described in more detail.

4.1. Physiological Mechanical Activity Sensor Module

As stated above, sensor module 902 monitors a physiological mechanical activity of subject 910. Sensor module 902 processes, preferably in real time, the physiological mechanical activity signals to derive the necessary information used by optical events module 904. Referring to FIG. 10, sensor module 902 is comprised of one or more physiological mechanical sensor(s) 1002 and a signal-conditioning module 1004. Both of these are described in more detail below.

4.1.1. Physiological Mechanical Sensor

One or more of physiological mechanical sensor 1002 is utilized for detecting, transducing or deriving signals related to the physiological mechanical activity being monitored. Physiological mechanical sensor 1002 may be comprised of one or more of those currently used in the art, including but not limited to, those used in reography or doppler techniques and/or in photoplethysmography devices to detect the arterial and/or venous pulse, and/or those to measure blood pressure, and/or those used to currently detect the ECG and/or those to detect the periodic mechanical chest movements due to the breathing activity. Physiological mechanical sensors 1002 encompass the above examples and also, in general, any other sensors currently existing or to be developed in the future and by which signals representative of physiological mechanical activity of the heart and/or lungs and/or eyes of any other involuntary driven periodical and/or sequential physiological mechanical movements by the body could be directly or indirectly detected. The physiological mechanical activity detected by physiological mechanical sensor 1002 is forwarded to signal condition module 1004, which is described next.

4.1.2. Signal Conditioning Module

Signal conditioning module 1004 provides preferably real time conditioning and processing of signals produced or derived from the physiological mechanical activity being monitored. Signal conditioning module 1004 performs a number of well known steps in the relevant art(s) comprising, but not limited by, the steps of amplifying, filtering, multiplexing and converting analog signals to digital signals or vice versa, protocol conversion, etc. The digital signals are then transmitted directly or by wireless means to optical events module 904. Depending on the particular embodiment, signal-conditioning module 1004 may be physically located within optical events module 904. It is noted that while the processing of sensor module 902 has been described as operating in real time, in some embodiments such processing does not occur in real time. Next, optical events module 904 is described with reference to FIG. 11.

4.2. Optical Events Module

Optical events module 904 receives information from sensor module 902 and identifies a program for subject 910 that will trigger pre-attentive cuing and/or increase sensitivity of magnocellular reactivity in subject 910. Optical events module 904 involves controlling photic energetic parameters and photic early perceptual attributes that will determine both spatial and temporal fluctuations of light arrays 204 that are to be generated and outputted by optical field output 906. Optical events module 904 also receives information from game 908 which may alter the program for subject 910. Thus, based on the controls or program determined by optical events module 904, optical field output 906 and game 908 triggers pre-attentive cuing and/or increases sensitivity of magnocellular reactivity in subject 910.

FIG. 11 illustrates one embodiment of optical events module 904. Here, optical events module 904 is comprised of an optical events engine 1112 and various option libraries including a library of optical features for eliciting pre-attentive cuing 1102, a library of options to increase the reactivity of the visual magnocellular system 1104, a library of variability components (VC) for optical event ground state (GS) stimuli and/or changes in their stimuli parameters 1106, a library 1108 of control parameters for changes in the relative location of velocity vectors of optical events in relation to the location of subject 910, and a library 1110 of time correlations and (their) fluctuations of optical events ground state stimuli parameters and their changes with periodical and/or sequential involuntary driven mechanical movements in the body of subject 910. Each of these libraries are described next at a high level and are described in more detail below with reference to FIG. 25 describing an embodiment of the present invention.

4.2.1. Library of Optical Features for Eliciting Pre-Attentive Cuing

FIG. 14 illustrates library 1102 and example optical features for eliciting pre-attentive cuing in a subject. A limited set of optical features are picked up pre-attentively (without the need for focusing attention by the subject) and thus, the direct extraction of information of the particular visual scene it's accomplished via early visual perception, which resources to an egocentric mapping of space of the subject. In order for the subject to orient towards a perceptual optical feature pre-attentively, the subject must be able to perceptually pick out a target among a number of distractors in a fixed amount of time (<200 milliseconds) regardless of the number of distractors. Here, the perceptual relationship between the target and the distractors must be simple. Thus, pre-attentive orientating involves a parallel perceptual feature search of the visual scene that affords an implicit and direct information extraction of targets (as compared to visual ordinary perception that involves a perceptual serial feature searching of the visual scene that demands an explicit information processing of targets).

Example optical features that can be processed pre-attentively are shown in library 1102 in FIG. 14. Illustrations of some of these optical features are further illustrated in FIG. 19. In FIG. 19, various optical features are further illustrated, each one showing a number of perceptual distractors with one perceptual target. Most of the optical features shown in FIGS. 14 and 19 are self-explanatory. Optical features that may need some explanation in FIG. 14 include intensity 1422, stereoscopic depth 1430, 3-D depth cues 1432 and lightening direction 1434. Intensity 1422 is contrast. An illustration of this is a visual gray background as the perceptual distractor with a visual white dot on it as the perceptual target. Stereoscopic depth 1430 involves multiple perceptual distractors, where each perceptual distractor shows two objects with the same depth between the objects and a perceptual target that shows two objects that have a different depth. 3-D depth cue 1432 involves 3-D shapes where the perceptual target has a different 3-D shape from all of the perceptual distractors. Lightening direction 1434 involves emphasizing the surface of an object in a different way in the perceptual target than how it is done with the perceptual distractors. Library 1104 is described next.

4.2.2. Library of Options to Increase the Reactivity of the Visual Magnocellular System FIG. 15 illustrates library 1104 and example options to increase reactivity of the visual magnocellular system towards visual transient stimuli. One of these options 1502 involves promoting stimuli detection in the peripheral visual field 1502. Examples of how library 1104 may be implemented is described below with reference to FIG. 24.

Another option 1504 in library 1104 involves selecting a perceptual motor activity for a subject to periodically engage his or her focus attention towards the (foveal) central region of the displayed visual field where optical events take place in game/entertainment program module 908 (FIG. 9).

Option 1506 in library 1104 involves using a black-white visual field angular sectors alternance. Here, frequency of alternance equals angular degrees per each white-black alternance period. This is described further with reference to FIG. 20. Magnocellular cells react most efficiently when subjected to a low frequency angular alternance of black and white colors. This is shown in FIG. 20 by illustration 2002. Illustration 2002 shows a low frequency angular alternance of black and white colors. Alternatively, illustration 2004 shows a high frequency angular alternance of black and white colors, which triggers the reactivity of parvocellular cells.

Another option 1508 in library 1104 involves introducing temporal variability in duty cycles of transient stimuli. Transient stimuli duty cycles are herein characterized by a temporal variability of brief durations in stimuli parameters (the active part of the cycle) and in the time interval (the resting part of the cycle) between stimuli changes. This is further illustrated in FIG. 21. Illustration 2102 shows stimuli 2108 (the active part of the cycle) followed by a time interval 2110 (the resting part of the cycle). Illustration 2104 shows how stimuli 2108 is increased to show temporal viability in stimuli 2108 (the duration of stimuli is increased), whereas illustration 2106 shows how the time interval 2110 is now increased during stimuli 2108 changes.

4.2.3. Library of Variability Components (VC) for Optical Event Ground-State (Gs) Stimuli and/or Changes in Stimuli Parameters FIG. 16 illustrates library 1106 and example options of variability components (VC) for optical event ground state (Gs) stimuli and/or changes in stimuli parameters. The example options include time duration 1602; graphic display (e.g., form, width, length, size, etc.) 1604; color 1606; intensity 1608; number of changes in an optical event in time duration, graphic display, color and/or intensity 1610; magnitude of changes in the number of changes in an optical event 1612; and sequential order of changes at the number of changes in an optical event and/or in the magnitude of changes in the number of changes in an optical event 1614. Library 1108 is described next.

4.2.4. Library of Control Parameters for Changes in the Perceptual Relative Location of Velocity Vectors of Optical Events in Relation to the Location of the Subject FIG. 17 illustrates library 1108 and example options of control parameters for changes in the perceptual relative location of velocity vectors of optical events in relation to the location of subject 910. The example options include perceptual direction of movement 1702, perceptual orientation of movement 1704, perceptual magnitude of movement 1706, perceptual spatial coordinates at which an optical event emerges in the visual field 1708, and perceptual spatial coordinates at which an optical event abandons in the visual field 1710. Library 1110 is described next.

4.2.5. Library of Time Correlations and their fluctuations of Optical Events Ground State Stimuli Parameters and its Changes with Periodical and/or Sequential Involuntary Driven Mechanical Movements in the Body of Subject FIG. 18 illustrates library 1110 and example time correlations of optical events ground state stimuli parameters, their fluctuations and their changes with periodical and/or sequential involuntary driven mechanical movements in the body of subject 910. The example options include number of ground state optical event per each of the selected periodical and/or sequential occurrence of a mechanical movement in the body 1802 and option 1804 that deals with time delays and their fluctuations between a fiducial point in the periodical cycle and/or in the sequential mechanical movement in the body with the start of each of the ground state optical event stimuli and/or its changes as defined in library 1106. Optical events engine 1112 is described next.

4.2.6. Optional Events Engine

Optical events engine 1112 (FIG. 11) receives inputs from libraries 1102-1110 described above. The administrator and/or an expert system within the optional events engine 1112 determines the different variability options to be configured for a program of a particular subject, as will be described in detail below with one embodiment of the invention.

Optical events engine 1112 should be understood in its broader sense to be a programmable machine. Optical events engine 1112 may perform high speed processing of data. Therefore, optical events engine 1112 may involve a microcontroller, a microprocessor, a specially programmed machine incorporating instructions in ROM, PROM or other firmware, a specially programmed machine incorporating instructions, which are hardwired in, or a general-purpose computer together with a computer program. This computer program may have many forms including but not limited to an entertainment program, an interactive game program or an informative communication program.

In fact, optical events engine 1112 could be implemented using one of more of the computer systems described next with reference to FIG. 40. The computer system 4000 includes one or more processors, such as processor 4004. The processor 4004 is connected to a communication bus 4006. Various software embodiments are described in terms of this example computer system. After reading this description, it will become apparent to a person skilled in the relevant art how to implement the invention using other computer systems and/or computer architectures.

Computer system 4000 also includes a main memory 4008, preferably random access memory (RAM), and can also include a secondary memory 4010. The secondary memory 4010 can include, for example, a hard disk drive 4012 and/or a removable storage drive 4014, representing a floppy disk drive, a magnetic tape drive, an optical disk drive, etc. The removable storage drive 4014 reads from and/or writes to a removable storage unit 4018 in a well-known manner. Removable storage unit 4018, represents a floppy disk, magnetic tape, optical disk, etc. which is read by and written to by removable storage drive 4014. As will be appreciated, the removable storage unit 4018 includes a computer usable storage medium having stored therein computer software and/or data.

In alternative embodiments, secondary memory 4010 may include other similar means for allowing computer programs or other instructions to be loaded into computer system 4000. Such means can include, for example, a removable storage unit 4022 and an interface 4020. Examples of such can include a program cartridge and cartridge interface (such as that found in video game devices, video camcorder, and so forth), a removable memory chip (such as an EPROM, or PROM) and associated socket, and other removable storage units 4022 and interfaces 4020 which allow software and data to be transferred from the removable storage unit 4018 to computer system 4000.

Computer system 4000 can also include a communications interface 4024. Communications interface 4024 allows software and data to be transferred between computer system 4000 and external devices. Examples of communications interface 4024 can include a modem, a network interface (such as an Ethernet card), a communications port, a PCMCIA slot and card, etc. Software and data transferred via communications interface 4024 are in the form of signals 4026 which can be electronic, electromagnetic, optical or other signals capable of being received by communications interface 4024. These signals 4026 are provided to communications interface via a channel or path 4028. This channel 4028 carries signals 4026 and can be implemented using wire or cable, fiber optics, a phone line, a cellular phone link, an RF link and other communications channels.

In this document, the terms "computer program medium" and "computer usable medium" are used to generally refer to media such as removable storage device 4018, a hard disk installed in hard disk drive 4012, and signals 4026. These computer program products are means for providing software to computer system 4000.

Computer programs (also called computer control logic) are stored in main memory and/or secondary memory 4010. Computer programs can also be received via communications interface 4024. Such computer programs, when executed, enable the computer system 4000 to perform the features of the present invention as discussed herein. In particular, the computer programs, when executed, enable the processor 4004 to perform the features of the present invention. Accordingly, such computer programs represent controllers of the computer system 4000.

In an embodiment where the invention is implemented using software, the software may be stored in a computer program product and loaded into computer system 4000 using removable storage drive 4014, hard drive 4012 or communications interface 4024. The control logic (software), when executed by the processor 4004, causes the processor 4004 to perform the functions of the invention as described herein.

In another embodiment, the invention is implemented primarily in hardware using, for example, hardware components such as application specific integrated circuits (ASICs). Implementation of the hardware state machine so as to perform the functions described herein will be apparent to persons skilled in the relevant art(s). In yet another embodiment, the invention is implemented using a combination of both hardware and software. Optical field stimuli output module 906 is described next.

4.3. Optical Field Stimuli Output Module

FIG. 12 illustrates optical field stimuli output module 906, which receives input from optical events stimuli module 904 that defines a program for subject 910. Optical field stimuli output module 906 then generates and outputs the program. The program generated and outputted by optical field stimuli output module 906 may be modified by input from game/entertainment module 908.

As shown in FIG. 12, optical field stimuli output module 906 may be comprised of a module 1202, a module 1204 and a module 1206. Module 1202 generates and delivers to subject 910 the visual sensorial stimuli (physical attributes of stimuli), including information about pre-attentive features. Module 1204 generates and delivers visual sensorial stimuli to subject 910 to increase the reactivity of the magnocellular cells in subject 910. Module 1206 generates and delivers visual sensorial stimuli according to spatial, temporal and other stimuli parameters according to optical events stimuli module 904. A specific embodiment of optical field stimuli output module 906 is described below in detail.

4.4. Game/Entertainment Program Module

Game/entertainment program module 908 receives input from optical events stimuli module 904 and sends output to optical field stimuli output module 906 and to subject 910. A specific embodiment of game/entertainment program module 908 is described below in detail.

5. Example Embodiment of the Invention

FIG. 22 illustrates one embodiment of the invention that could be used to address, such as ameliorate, the condition of a dyslexic subject. As described above with reference to FIG. 9, sensor module 902 (comprised of physiological mechanical sensor(s) 1002 and signal conditioning module 1004) monitors the physiological mechanical activity of subject 910 and receives signals regarding particular physiological mechanical activity it is monitoring. Sensor module 902 processes, preferably in real time, the physiological mechanical activity signals to derive the necessary information used by optical events module 904. Optical events module 904 receives this information from sensor module 902 and identifies a program for subject 910 that aims to trigger pre-attentive cuing and/or increase sensitivity of magnocellular reactivity in subject 910. Optical events module 904 involves controlling photic energetic parameters and photic early perceptual attributes that will determine both spatial and temporal fluctuations of light arrays 204 that are to be generated and outputted by optical field output 906. Optical events module 904 also receives information from game 908 which may alter the program for subject 910.

In the example embodiment of the invention, game 908 is implemented as a periodic fashion game that allows subject 910 to periodically engage his or her ordinary visual perception to search (or focus attention) on a visual scenery and therby process and store visual information within the limitations imposed by the subject's attentional mechanism capacity. Thus, based on the controls or program determined by optical events module 904, optical field output 906 and game 908 triggers pre-attentive cuing and/or increases sensitivity of magnocellular reactivity in subject 910.

In this embodiment, it is assumed that physiological mechanical sensor 1002 is an ECG machine from where the heart cycle of subject 910 can be monitored.

It is also assumed that optical events module 904 produces a dynamic environment that is conveyed to subject 910 via optical field output 906. This dynamic environment is displayed on a computer screen display and represents a perceptual intrinsic variable simple optical flow field that embeds preattentive features once it reaches the eye of the subject. The dynamic environment is defined by ground states and eighteen different variability components (VCs) as defined in FIGS. 25-27 that control the visual field stimuli generated and displayed by optical field output 906. Thus, optical field output 906 generates an optical field displayed on the computer screen display which generates a particular photic field spatiotemporal configuration display as defined by the administrator (with optical events module 904) with the VCs. Also in this embodiment, game module 908 occupies (at times) the center of the computer screen display at particular periods. The screen display of the embodiment of optical field output 906 and game module 908 are shown in FIG. 24. Input device module 2202 is a mouse and allows subject 910 to bio-motorically engage in game 908.

An example embodiment of optical field output 906 and game module 908 are shown in FIG. 24. As will be described in detail below, in this embodiment one ground state event is defined as the generation of an optical event icon with a perceptual rectilinear form on the screen display of optical field output 906. Example optical event icons are shown in FIG. 24. Each of the modules in this embodiment of the invention is described next in more detail.

5.1. Physiological Mechanical Sensor

Physiological mechanical sensor 1002 includes an ECG machine from where the heart mechanical cycle of subject 910 can be monitored. Physiological mechanical sensor 1002 is located on the body of subject 910 (e.g., subject 910 may wear a heart chest strap that contains one or more ECG electrodes). Signals corresponding to the periodic mechanical activity of the heart are transmitted by wireless means to optical events module 904. By this means, the previously selected ground state stimuli parameters of the optical event, as well as changes in stimuli parameters can be synchronized (in a variable fluctuated manner) with a selected fiducial point of the periodical mechanical movements of the heart cycle of subject 910. In this embodiment, the generated visual stimuli can be optionally correlated with either the early portion of the heart contraction cycle (mechanical systole) or with the late portion of the heart contraction cycle (mechanical diastole), or any portion thereof (as determined by the invention). By non-invasively monitoring (e.g., the arterial pressure wave on the carotid, sub-clavia or radial artery) it can be directly shown the subject's systolic and diastolic phases of the heart cycle. This can also be done non-invasively with piezo-electric sensors. Also by photopletismographic transducer methods, the subject's pulse can directly be obtained and thereby monitor systolic and diastolic phases of the heart mechanical cycle.

The ECG does not directly show the early and late portions of the heart contraction cycle, known under the names of mechanical systole and mechanical diastole. Nevertheless, they can be obtained with sufficient approximation for the purpose of some embodiments of this invention, by way of a mathematical function depending only upon the gender and mean heart rate of the subject. The below mathematical functions were obtained from data on large sample groups. The main electrical ECG events characterizing the heart function are shown in FIG. 23. The QRS complex shows the ventricular depolarization, the Pwave showing the depolarization of the atria, and the Twave showing the repolarization of the ventricules. The pre-ejection period (PEP) spans normally from the Q point in the ECG until few tens of milliseconds behind the S point in the ECG. The end of PEP marks the start of the mechanical systole of the ventricules (MS), and the MS ends around the end of the Twave. The mechanical diastole of the ventricules starts where MS ends and ends in the next Q point, after the P wave. Expressions defining the three main sub-cyles of the ventricular or heart cycle are given below, as a function of gender (M or F) and the mean heart rate (mHR), as shown in the Table below.

TABLE

Sub-Cycles length (milliseconds) of the Heart Period as a function of Heart Rate (HR) in beats/min

| Sub-Cycle | Men | Women |
| --- | --- | --- |
| Left ventricular Ejection Time or Mechanical Systole (MS)* | 413 - 1.7 HR | 418 - 1.6 HR |
| Pre-ejection Period (PEP) | 131 - 0.4 HR | 133 - 0.4 HR |
| Refilling of Left Ventricle or Mechanical Diastole (MD) | $2.1\ HR + 6 \times 10^4/$ $HR - 544$ | $2\ HR + 6 \times 10^4/$ $HR - 551$ |

Obtained from 121 man and 90 women by: Weissler et al, Bedsides techniques for the evaluation of ventricular function in man. Amer J. Cardiol 23:577,1969. Weissler et al, Systolic time intervals in heart failure in man, Circulation 37:149,1968.

5.2. Optical Events Stimuli Module

Optical events module 904 receives information from sensor module 902 and identifies a program for subject 910 (as configured by an administrator) that will trigger pre-attentive cuing and/or increase sensitivity of magnocellular reactivity in subject 910. Optical events module 904 involves controlling photic energetic parameters and photic early perceptual attributes that will determine both spatial and temporal fluctuations of light arrays 204 (FIG. 2) that are to be generated and outputted by optical field output 906. In this embodiment the photic energetic parameters and photic early perceptual attributes are defined by ground states and eighteen different variability components (VCs) to create a photic field structure. An optical event is defined in this embodiment as a ground state and also as any changes in the velocity vectors of the ground state optical events and/or in their photic properties (e.g., color, thickness, size, brightness, direction, orientation, and so forth).

In this embodiment, one ground state event is defined as the generation of an icon with a perceptual rectilinear form which is selected according to its pre-attentive cuing attributes and with a defined RGB color of white. Here, only one ground state optical event (or optical event icon or optical event photic stimuli) per cardiac cycle will enter the perceptual visual optical field of subject 910. The computer screen display background color in optical field output 906 is defined by RGB of (61,17,90). The fluctuations/variabilities to the ground states are provided by eighteen different VCs as shown in FIGS. 25-27 and will be described in detail below. A user interface will be provided to an administrator that will control the configuration of the eighteen VCs in order to generate different photic field structures in accordance with a desired objective. For example, 5, 10, 15 or more VCs may be utilized for one photic field structure. FIG. 13 illustrates the steps to be carried out by an administrator or operator to configure this VCs, as is described next.

In step 1302 of FIG. 13, an operator selects optical features for eliciting pre-attentive cuing in library 1102 and the desired fluctuations in randomness and periodicity for such selections. Control then passes to step 1304.

In step 1304, the operator selects from the options to increase the reactivity of the visual magnocellular system in library 1104 and the desired fluctuations in randomness and periodicity for such selections. Control then passes to step 1306.

In step 1306, the operator selects from the variability components for optical events ground state stimuli and/or changes in stimuli parameters in library 1106 and the desired fluctuations in randomness and periodicity for such selections. Control then passes to step 1308.

In step 1308, the operator selects from the control parameters for changes in the relative location of velocity vectors of optical events in relation to the subject's location in library 1108 and the desired fluctuations in randomness and periodicity for such selections. Control then passes to step 1310.

In step 1310, the operator selects from the time correlations of optical events ground state stimuli parameters and their changes with periodical and/or sequential involuntary driven mechanical movements in the subject's body in library 1110 and the desired fluctuations in randomness and periodicity for such selections. The flowchart in FIG. 13 ends at this point. The eighteen different VCs are described next with reference to FIGS. 26 and 27.

FIG. 26 illustrates the temporal variability conditions (VCs) used by this embodiment of the invention in order to temporally fluctuate both the energetic parameters and the photic early perceptual attributes of an optical event icon that perceptually enters and travels across the computer screen display of optical field output 906 of subject 910. FIG. 27 illustrates the spatial VCs used by the embodiment of the invention in order to spatially fluctuate the photic energetic parameters and photic early perceptual attributes of the optical event icon. It should be understood that optical field output 906 is generated by a plurality of optical event icons. But, for simplicity and illustration purposes, the description of the VCs will be in reference to changes for a single optical event icon.

It is important to note that the present invention allows for increasing hierarchies of VCs to allow for maximum variability in the fluctuations of both the photic early perceptual attributes and the photic energetic parameters of the optical event icon. The hierarchies are selected by the administrator by layering different VCs in order to define a program for a particular subject 910. An example of how the hierarchies between VC 2501-VC 2518 is illustrated in the hierarchy tree shown in FIG. 41. The hierarchies reshuffled and thus further fluctuated via a randomness/periodicity feature of the invention. The randomness/periodicity feature of the invention is provided to the administrator via a user interface described below with reference to FIG. 29. To aid in the understanding of the invention, one VC will be described and then the specifics of that VC will be used to provide an explanation of how the randomness/periodicity feature operates.

Referring to FIG. 26, VC 2501 is first described. VC 2501 allows for three options for the occurrence of a ground state optical event icon and/or for its perceptual changes on the screen display of optical field output 906. As described above, one ground state icon per cardiac cycle will perceptually enter the visual optical field of subject 910. Thus, the three options are illustrated in FIG. 28. Here, the optical event icon can perceptually enter the screen display and/or change while traveling across the screen display during mechanical systole 2802, mechanical diastole 2804, or both mechanical systole 2802 and mechanical diastole 2804 of the heart cycle of subject 910. The administrator may decide, for example, to have one optical event icon perceptually appear and/or change while it moves along on the screen display of optical field output 906, during the mechanical diastole option for each heart cycle of subject 910. This is referred to herein as 100% periodicity. Alternatively, the administrator may decide to increase the variability of the occurrence of the optical event icon on the screen display of optical field output 906 via the randomness/periodicity feature of the invention, as described next with reference to FIG. 29.

FIG. 29 illustrates an example user interface 2900 provided to the administrator of the invention as it relates to VC 2501. Here, the invention allows the administrator to determine the amount of variability of VC 2501. For example, if the administrator wants to have the optical event icon displayed and/or changed on the screen display of optical field output 906 during the mechanical systole option only and for each heart cycle, the administrator will enter 100% for block 2904 and check the mechanical systole block 2906. Once the administrator has decided on the configuration, the administrator clicks the confirm 2914 button. The change button 2912 allows the administrator to reconfigure and update the configuration.

In another example, if the administrator wants to display the optical event icon randomly for one of the three options (mechanical systole, mechanical diastole, and mechanical systole/mechanical diastole), then the administrator will enter 100% in block 2902 and check all blocks 2906, 2908 and 2910. Here, the invention will randomly pick one of options mechanical systole, mechanical diastole or mechanical systole/mechanical diastole to display the optical event icon and/or its changes on the screen display of optical field output 906 during each heart cycle of subject 910. For this particular configuration of the randomness/periodicity feature of the invention and assuming a frequency of 60 heart cycles per minute, it is unknown the order in which the three options will be randomly chosen each time, but the invention does guarantee that for the 60 heart cycles a minute, 20 times the mechanical systole option will be chosen, 20 times the mechanical diastole option will be chosen and 20 times the mechanical systole/mechanical diastole option will be chosen. This randomness shuffling may be combined with some percentage of periodicity by, for example, entering 80% in block 2902 and 20% in block 2904. This now guarantees a higher degree of repetitivity in the chosen option if compared with the previous 100% randomness configuration.

The randomness/periodicity feature of the invention applies to all the VCs that will now be described in reference to FIGS. 26 and 27. VC 2502 is described next.

Referring back to FIG. 26, VC 2502 defines a systemic higher and independent hierarchy from VC 2501 (See FIG. 41) and thus provides for another level of variability to the optical event icon on the screen display of optical field output 906. With VC 2501, an occurrence and/or change of the optical event icon on the screen display happens at each heart cycle (stimuli is provided to subject 910 at each heart cycle). VC 2502 allows the administrator to provide a higher systemic and independent hierarchy to VC 2501 and override the occurrence of the optical event icon and/or its changes on the screen display at each heart cycle (stimuli may not be provided to subject 910 at each heart cycle). Thus, the administrator may override VC 2501 with VC 2502 by preventing the occurrence of the optical event icon for one heart cycle every 20 heart cycles, or for two heart cycles every 20 heart cycles, and so forth. VC 2504 (FIG. 26) is described next and provides yet another level of systemic hierarchy to VC 2501 and VC 2502 when the mechanical diastole option is chosen by the administrator in VC 2501 (See FIG. 41).

With VC 2504 for a particular heart cycle (assuming that the mechanical diastole option is chosen in VC 2501 and assuming that VC 2502 is not blocking the stimuli or optical event icon from occurring during the particular heart cycle), VC 2504 provides for four options for the total temporal duration of three successive photic optical event changes in mechanical diastole. The four options are illustrated with reference to FIG. 30. In FIG. 30, the total time duration 3001 of the occurrence of optical event (i.e., stimuli being provided to subject 910) is further subdivided into three successive photic optical event changes. Note that the invention also may provide a variability component for different options for the total temporal duration of two or more successive photic optical event changes in mechanical systole. These successive photic optical event changes are shown in FIG. 30 as change 3002, change 3004 and change 3006.

Also in FIG. 30, the four options for the total time duration of three successive photic optical event changes in mechanical diastole are illustrated in user interface 3008. In the example user interface 3008 the four options include 80 milliseconds, 100 milliseconds, 120 milliseconds and 140 milliseconds. As described in FIG. 29, the administrator has a choice to determine the percentages of randomness and periodicity at which these four options will be selected by optical events engine 1112 (FIG. 11) in FIG. 25. VC 2503 is described next and provides yet another level of systemic hierarchy to VC 2501, VC 2502 and VC 2504 (See FIG. 41).

VC 2503 provides for two wave amplitude envelope form options for the three consecutive photic changes during the optical event occurring in mechanical diastole in VC 2504. These two options 3102 and 3104 are illustrated in FIG. 31. Here again, the invention provides a user interface 3106 where the administrator may chose between option 3102 (illustrated as "A" in user interface 3106), option 3104 (illustrated as "B" in user interface 3106), or both options 3102 and 3104. The administrator then specifies the percentages of randomness and periodicity desired as described above with reference to FIG. 29. VC 2518 is described next and provides yet another level of systemic hierarchy to VC 2501, VC 2502, VC 2504 and VC 2503 (See FIG. 41).

VC 2518 is a spatial VC (FIG. 27) and provides for a choice among four optical event icon thickness (defined as number of pixels). The optical event icon thickness may change within the different three consecutive photic changes during the optical event occurring in mechanical diastole in VC 2503. Example choices for the four different options for icon thickness are shown in FIG. 32 via example user interface 3202 and include 6, 8, 10 or 12 pixel thickness. As described with the other VCs, the invention allows the administrator to specify the percentages of randomness and periodicity regarding the four different options for icon thickness. VC 2505 (FIG. 26) is described next and provides yet another level of systemic hierarchy to VC 2501 and VC 2502 when the mechanical systole option is chosen in VC 2501 (See FIG. 41).

VC 2505 for a particular heart cycle (assuming that the mechanical systole option is chosen in VC 2501 and assuming that VC 2502 is not blocking the stimuli or optical event icon from occurring during the particular heart cycle) provides for four options for the total time duration of the optical event icon (duration of the stimuli) in mechanical systole. The four options are illustrated with reference to FIG. 33. In FIG. 33, the total time duration 3301 of the occurrence of optical event icon (i.e., stimuli being provided to subject 910) is shown. Note that unlike VC 2504, the total time duration 3301 is not further subdivided into three successive photic optical event changes. Example values for the total duration 3301 is shown in example user interface 3302. In the example user interface 3302 includes four options include 60 milliseconds, 61 milliseconds, 65 milliseconds and 70 milliseconds. As with the other VCs described above, the administrator has a choice to determine the percentages of randomness and periodicity with VC 2505. VC 2506 is described next and provides yet another level of systemic hierarchy to VC 2501, VC 2502 and VC 2505 when the mechanical systole option is chosen in VC 2501 (See FIG. 41).

VC 2506 provides for four options for a time delay before the total time duration 3301 of the optical event icon begins in mechanical systole in VC 2505. This time delay 3404 is measured in relation to a fiducial point 3402 in the ECG, as shown with reference to FIG. 34. Example values for the time delay 3404 is shown in example user interface 3406. In the example user interface 3406 the four options include 200 milliseconds, 225 milliseconds, 250 milliseconds and 275 milliseconds. Here also the administrator has a choice to determine the percentages of randomness and periodicity with VC 2506. VC 2507 is described next and is similar to VC 2506 except that it provides for a time delay in mechanical diastole (instead of mechanical systole) (See FIG. 41).

VC 2507 provides for eight options for a time delay before the total time duration 3001 (FIG. 30) of the optical event icon begins in mechanical diastole in VC 2504. This time delay 3502 is measured in relation to a fiducial point 3402 in the ECG, as shown with reference to FIG. 35. Example values for the time delay 3502 is shown in example user interface 3504. In the example user interface 3504 the eight options include 400 milliseconds, 425 milliseconds, 450 milliseconds, 475 milliseconds, 500 milliseconds, 525 milliseconds, 550 milliseconds, and 575 milliseconds. Here also the administrator has a choice to determine the percentages of randomness and periodicity with VC 2507. VC 2508 is described next and provides yet another level of systemic hierarchy to VC 2501, VC 2502, and VC 2504 (See FIG. 41).

VC 2508 provides for seven color options for each one of the three consecutive photic changes during the optical event icon occurring in mechanical diastole in VC 2504 (FIG. 30). These seven color options are each defined as a RGB. As above, the administrator specifies the desired percentages of randomness and periodicity. Spatial VC 2511 provides yet another level of systemic hierarchy to VC 2501 is described next to aid in the illustration of the remaining temporal VCs (VC 2512, VC 2513 and VC 2514) (See FIG. 41).

VC 2511 is defined as a spatial VC (FIG. 27) and provides yet another level of systemic hierarchy to VC 2501 and VC 2502. VC 2511 provides four options of possible screen display zones that the optical event icon may perceptually emerge on the screen display of optical field output 906 of subject 910. An example embodiment of optical field output 906 is shown in FIG. 36. The four options include the top left of the screen display (defined from point 3602 to point 3604), the top right of the screen display (defined from point 3604 to point 3606), the bottom right of the screen display (defined from point 3606 to point 3608) and the bottom left of the screen display (defined from point 3608 to point 3602). The invention provides the administrator a user interface to configure the desired percentages of randomness and periodicity for VC 2511. Temporal VC 2512 is described next and provides yet another level of systemic hierarchy to VC 2511 (See FIG. 41).

VC 2512 provides for four possible time periods measured in seconds during which an optical event icon will perceptually keep emerging from the zone defined in VC 2511. As with VC 2511, the invention provides the administrator a user interface to configure the desired percentages of randomness and periodicity for VC 2512. VC 2513 is described next and provides yet another level of systemic hierarchy to VC 2511 (See FIG. 41).

VC 2513 provides for four possible total time periods for which an optical event icon has to move across the screen display of optical field output 906 once it perceptually emerges from the zone defined in VC 2511. The available total time periods are computed as a number of elapsed heart cycles of subject 910. Example total time periods for optical event icon perceptually moving across the screen display include 10, 20, 100 heart cycles. The invention provides the administrator a user interface to configure the desired percentages of randomness and periodicity for VC 2513. VC 2514 is described next and provides yet another level of systemic hierarchy to VC 2511 (See FIG. 41).

VC 2514 provides for three possible options for changing the velocity of an optical event icon as it moves across the screen display of optical field output 906, once it perceptually emerges from the zone defined in VC 2511 of subject 910. Example velocity options include increasing icon velocity (acceleration), decreasing its velocity from the perceptual instant of its emergency into the screen display till the icon perceptually abandons the screen display. Because traveling distance and number of heart cycles to traverse that distance are known, the initial velocity and its changes can be calculated by optical event engine 1112. The invention provides the administrator a user interface to configure the desired percentages of randomness and periodicity for VC 2514. Spatial VC 2511 was already described above and the remaining spatial VCs (FIG. 27) will be described next.

VC 2515 provides yet another level of systemic hierarchy to VC 2511 (See FIG. 41). VC 2515 further sub-divides each of the four options of possible screen display zones provided by VC 2511 into additional 4 sub-zones. These sub-zones are illustrated in FIG. 37 for the upper left screen display zone only (defined by points 3602 and 3604 in FIG. 36). Here options for the sub-zones for the upper left screen display zone include from point 3602 to point 3702, from point 3702 to point 3704, from point 3704 to point 3706, and from point 3706 to point 3604. Although not shown in FIG. 37, all other screen display zones described with reference to VC 2511 are sub-divided in a similar way. With VC 2515, there now exists a total of sixteen different locations/options from which the optical event icon may perceptually emerge on the screen display of optical field output 906 of subject 910. The invention provides the administrator a user interface to configure the desired percentages of randomness and periodicity for VC 2515.

VC 2516 provides yet another level of systemic hierarchy to VC 2515 (See FIG. 41). VC 2516 further sub-divides each of the sixteen different sub-zones as defined in VC 2515. An example of how this is done by the invention is shown in FIG. 38. Here, sub-zone (defined by points 3602 and 3702 in FIG. 37) is further divided into eight sub-zones, including from point 3602 to point 3802, from point 3802 to point 3804, and so forth. Again, as with VC 2515 and FIG. 37, all other sub-zones described with reference to VC 2515 are sub-divided in a similar way. With VC 2516, there now exist a total of 128 different locations/options from which the optical event icon may perceptually emerge on the screen display of optical field output 906 of subject 910. Again, the invention provides the administrator a user interface to configure the desired percentages of randomness and periodicity for VC 2516. VC 2517 is described next and provides yet another level of systemic hierarchy to VC 2516 (See FIG. 41).

VC 2517 provides, for each of the 8 sub-zones defined in VC 2516, eight different options for the optical event icon to perceptually terminate or arrive at the opposite and respective sub-zone from which it perceptually emerged. VC 2517 is further described with reference to FIG. 39. The opposite and respective sub-zone for sub-zone defined by points 3602 and 3702 is shown as the sub-zone in FIG. 39 defined by points 3606 and 3902. Thus, for an optical event icon that perceptually emerges in the sub-zone defined in VC 2516 (for example the zone defined by points 3806 and 3808), VC 2517 provides for eight different perceptually termination sub-zones including the sub-zones defined by point 3606 to point 3904, from point 3904 to point 3906, from point 3906 to point 3908, from point 3908 to point 3910, and so forth. The invention provides the administrator a user interface to configure the desired percentages of randomness and periodicity for VC 2517. VC 2509 is next described and provides yet another level of systemic hierarchy to VC 2501, VC 2502, VC 2504 and VC 2503 (See FIG. 41).

VC 2509 provides for a choice between optical event icon lengths, which are given as a fraction of the total width of the screen display of optical field output 906. The optical event icon length may change within the different three consecutive photic changes during the optical event occurring in mechanical diastole in VC 2503. Example choices for the two different options for icon length include $\frac{1}{20}$ and $\frac{1}{100}$ of the total screen display's width. As described with the other VCs, the invention allows the administrator to specify the percentages of randomness and periodicity regarding the four different options for icon length. VC 2510 is described next and also provides yet another level of systemic hierarchy to VC 2501, VC 2502, VC 2504 and VC 2503 (See FIG. 41).

VC 2510 provides for a choice among 'N' options for the graphic form of the optical event icon, where the perceptual different graphic forms vary in terms of the number of terminators and/or the relative length of the lines defining the icon's form. The options may change within the different three consecutive photic changes during the optical event that takes place in mechanical diastole in VC 2503. The invention allows the administrator to specify the percentages of randomness and periodicity regarding the two or more different options for graphic form of the optical event icon. Optical field stimuli output module 906 is described next.

5.3. Optical Field Stimuli Output Module

The dynamic environment provided by the invention is defined by ground states and eighteen different variability components (VC 2501-VC 2518) that control the visual field stimuli generated and displayed by optical field output 906. Thus, optical field output 906 generates an optical field displayed for example on a computer screen display and produces a particular photic field spatiotemporal configuration as defined by the administrator (with optical events module 904) via VC 2501-VC 2518. The central window for the game may be shown periodically. When the game is present, the screen display of the embodiment of optical field output 906 is shown in FIG. 24.

As shown in FIG. 24 and described above with reference to VC 2501-VC 2518, optical field output 906 generates and the subject 910 perceives a display of photic stimuli configured in the form of at least one array of consecutive one dimensional optical event icons moving rectilinearly, one after the other, and in the same direction and orientation against a screen display background of a controlled ground state of contrasting color. The goal of the spatial configuration of all potential perceptual emerging optical event icons at defined points on the screen display of optical field output 906 of subject 910 is aimed at generating a particular simple optical flow field type perceptual phenomena. As described above, the temporal and spatial distribution of the optical event icons are controlled by optical events stimuli module 904 (as configured by the administrator). A game (via game module 908) is periodically displayed and perceived on the middle of the optical visual field, and inside a separate and central window. While the game is displayed, the dynamic environment conveys by the optical event icon visual field perceptually continues to be displayed to subject 910. This produces the visual (allocentric) illusory sensation of depth, which is internalized by the ordinary perception of subject 910, as if the visual dynamic environment at the time the central window is displayed comprises the third dimension, which helps subject 910 with orienting towards salient stimuli (pre-attentive cuing). In order for the dynamic environment generated by the optical event icon perceptual visual field to aid in the activation of the peripheral vision of subject 910, the subject is instructed to intentionally keep his or her central vision engaged (focus attention) in the bio-motoric performance of the game via game module 908. Game module 908 is next described in more detail.

5.4. Game/Entertainment Program Module

Also in this embodiment, game module 908 produces a game that visually is perceived occupying (at times) the center of the computer screen display, as illustrated in FIG. 24. Input device module 2202 is a mouse and allows subject 910 to bio-motorically engage in the game. In FIG. 24, game module 908 produces a number of vertically oriented lines that are displayed at the center of the central window. These vertically oriented lines are, for example, displayed sinusoidal with constant or variable amplitude. The vertically oriented lines move in a block, up-down or down-up, at a controlled speed. The separation of the vertically oriented lines may be configured so that they can be optionally made as an integer or fractional relationship with the separation between screen display location points for the perceptual emerging optical event icons.

Preferably the present invention utilizes colors in game module 908 that triggers the most efficient reactivity of the magnocellular cells of subject 910, including blacks, grays and whites. Game module 910 also produces an icon e.g. a car that is bio-motorically moved by subject 910 towards the right or left and along one horizontal direction crossing the vertically oriented lines. The color of the icon, or for example a car, could be red or yellow in color to promote a significant reactivity of the parvocellular cells in subject 910. Subject 910 is instructed during each game to bio-motorically keep the icon or for example a car as close as possible to the middle point between the vertically oriented lines despite the vertically oriented movement of the lines. The present invention optionally provides to subject 910 a reward score which is given at the end of the game that reflects his or her ability to bio-motorically maintain the icon or for example car as close as possible to the middle point. Based on the score received by subject 910, he or she may receive a reward.

The present invention may also provide variability components that are specific to game module 908. Such variability components include fluctuating the location of the game module 908 on the screen display of optical field stimuli output module 906; fluctuating the shape of game module 908 (e.g., rectangle, square, circle, symbol-shaped, and so forth); fluctuating the time when game module 908 perceptually appears on the screen display of optical field stimuli output module 906; and fluctuating the color, intensity, and/or saturation of game module 908. Another fluctuation of game module 910 involves fluctuating the theme (e.g., driving a car, flying an airplane, driving a boat, and so forth). Another fluctuation of the game module 908 involves fluctuating the serial order of the theme appearance.

6. Implementation of the Present Invention in Televisions, Billboard Signs, Vehicle Windshields, and Computer Software Programs In other embodiments of the invention, optical field stimuli output module 906 is integrated into a television, billboard sign, vehicle windshield, computer software programs, and so forth, (where the television, billboard sign, vehicle windshield, and computer software program act as game/entertainment program module 908) to trigger pre-attentive cuing and/or increases sensitivity of magnocellular reactivity in a subject towards visual transient stimuli. An example embodiment of the invention where optical field stimuli output module 906 is integrated into a television is shown in FIG. 42.

In FIG. 42, in an embodiment, optical field stimuli output module 906 functions as described above. Television 4202 may provide at least some of the functions as described above with reference to game/entertainment program module 908. For example, while the subject is watching a television program, the subject engages his or her visual ordinary perception to search (or focus-attention) on a visual scenery (i.e., the television show the subject is currently watching) and thereby process and store visual information within the limitations imposed by the subject's attentional mechanism capacity. This is also true for a billboard sign that the subject is reading, the vehicle windshield as the subject is focused on driving his or her vehicle, and a computer software program (e.g., word processing software) while the subject is at work. It should be apparent that the present invention may be extended to many scenarios in everyday life that require the subject to engage his or her ordinary perception to focus attention on a visual scenery.

7. Implementation of the Present Invention Regarding the Slow Smooth Pursue and Fluctuation of the Eye While Reading There are two types of ballistic eye movements that help to satisfy the mapping of egocentric space 104 (FIG. 1) and are the type of movement that are controlled by the SC and the cerebellum, including saccades and slow smooth pursue of the eye. In an embodiment, the invention encourages the smooth pursue of the eye of a subject when reading by displaying symbols (e.g., words, letters, numbers, and so forth) to be read by the subject in such a way that the symbols translationally move slowly in a linear fashion across a screen display as the subject reads. The invention may also encourage saccades in the eye of the subject by fluctuating at times the symbols on the screen display as the subject reads by changing one or more individual symbol's color, size, font, graphical appearance, and so forth. Both the linear translational movement and fluctuation of the symbols are coordinated with the subject's physiological mechanical activity via physiological mechanical activity sensor module 902 (FIG. 9) described above.

8. Conclusion

While some embodiments of the present invention has been described above, it should be understood that it has been presented by way of examples only, and not meant to limit the invention. It will be understood by those skilled in the art that various changes in form and detail may be made therein without departing from the spirit and scope of the invention as defined in the appended claims. Thus, the breadth and scope of the present invention should not be limited by the above-described exemplary embodiments, but should be defined only in accordance with the following claims and their equivalents. Each document cited herein is hereby incorporated by reference in its entirety.

What is claimed is:

1. A method to address early visual-sensory motor perception of a subject, comprising the steps of:
   (1) controlling photic energetic parameters and photic perceptual attributes to trigger pre-attentive cuing or increase reactivity in magnocellular activity towards transient visual stimuli of the subject; and
   (2) generating an optical field comprising optical events based on said photic energetic parameters and said photic perceptual attributes, wherein said optical field transforms into a simple optical flow in the perceptual visual field of said subject.

2. The method of claim 1, wherein step (1) comprises:
   controlling photic energetic parameters and photic perceptual attributes to trigger pre-attentive cuing and increase reactivity in magnocellular activity towards transient visual stimuli of the subject.

3. The method of claim 1, wherein said photic energetic parameters comprise light array energetic features.

4. The method of claim 3, wherein said light array energetic features comprise at least one or more of wavelength, amplitude, intensity, phase, polarization, coherence, hue, brightness, and saturation.

5. The method of claim 3, wherein said light array energetic features cause motor activity in said subject that can be delayed or inhibited by said subject.

6. The method of claim 5, wherein said motor activity is communicative.

7. The method of claim 6, wherein said motor activity comprises one or more of facial movements, eye movements, finger pointing, and verbal reports by said subject.

8. The method of claim 5, wherein said light array energetic features may trigger imminent ballistic movements in said subject when at least intensity of said light array energetic features is substantial.

9. The method of claim 1, wherein said photic perceptual attributes include the spatiotemporal patterning of said optical events.

10. The method of claim 9, wherein said spatiotemporal patterning is perceivable by said subject, and comprises one or more of perceivable changes in at least motion, location, direction, duration, and orientation of said optical events.

11. The method of claim 10, wherein said motion comprises simple motion.

12. The method of claim 11, wherein said simple motion comprises 1-D translational motion or some forms of planar motion.

13. The method of claim 11, wherein said simple motion comprises motion that does not cause self-motion by said subject, or does not cause an ordinary discriminatory perceptual act by said subject of object motion towards or away of said subject.

14. The method of claim 11, wherein said simple motion comprises implicit awareness about motion that does not cause information to be processed by ordinary perception in the said subject.

15. The method of claim 9, wherein said spatiotemporal patterning of said optical events trigger imminent ballistic movements in body parts of said subject.

16. The method of claim 15, wherein said imminent ballistic movements comprises body part mechanical movements.

17. The method of claim 16, wherein said body part mechanical movements are perceptually physically distributed along the entire body of said subject.

18. The method of claim 16, wherein said body part mechanical movements are target organs and muscles physically distributed along the visceral space of said subject.

19. The method of claim 16, wherein said body part mechanical movements include one or more arm movements for reaching, finger aperture movements, hand movements for grabbing, eye saccades movements for orienting, eye smooth pursue movements, head movements, chewing movements, neck movements and waist movements.

20. The method of claim 15, wherein said imminent ballistic movements are mechanical movements of one or more body parts in egocentric space of said subject.

21. The method of claim 20, wherein said imminent ballistic movements comprise proximal distal movements in reachable space of said subject, that cannot be delayed, that are uninterruptible once initiated, that are non-communicative, and that occur in a time span of a pre-attentive time event.

22. The method of claim 15, wherein said imminent ballistic movements comprise N sequential body part mechanical movements, which collectively fulfil an imminent motoric goal.

23. The method of claim 15, wherein steps (1) and (2) comprise:
   triggering said imminent ballistic movements to facilitate extraction and integration of information about various egocentric spaces of said subject via early perception.

24. The method of claim 15, wherein steps (1) and (2) comprise:
   triggering said imminent ballistic movements to facilitate extraction and transformation of information about various egocentric spaces of said subject via early perception.

25. The method of claim 15, wherein steps (1) and (2) comprise:
   triggering said imminent ballistic movements to increase transient stimuli reactivity in magnocellular activity of the subject.

26. The method of claim 15, wherein steps (1) and (2) comprise:
   triggering said imminent ballistic movements to effectively guide sensory motor behaviour of said subject.

27. The method of claim 1, further comprising:
   modulating control of said photic energetic parameters and said photic perceptual attributes to increase magnocellular reactivity towards extracting information from early motion perception without cognitive awareness of said subject.

28. The method of claim 27, wherein said modulating step comprises:
   regulating participation of said photic energetic parameters and said photic perceptual attributes in generating said optical events.

29. The method of claim 28, wherein said regulating step comprises the step of:
   regulating participation of said photic energetic parameters and said photic perceptual attributes in generating said optical events to control energetic impact of said optical events.

30. The method of claim 28, wherein said regulating step comprises the step of:
   regulating participation of said photic energetic parameters and said photic perceptual attributes in generating said optical events to modulate early perceptual spatiotemporal influences of said optical events.

31. The method of claim 1, wherein said optical events comprise ground states and excited ground states.

32. The method of claim 1, further comprising:
time correlating said optical events based on feedback from said subject.

33. The method of claim 32, wherein said time correlating step comprises:
time correlating said optical events with involuntary driven physiological mechanical periodical or sequential movements of the subject.

34. The method of claim 33, wherein said involuntary driven physiological mechanical periodical or sequential movements of the subject comprise at least one or more of the cyclical movement of one or more of the heart and lungs of said subject.

35. The method of claim 33, wherein said involuntary driven physiological mechanical periodical or sequential movements of the subject comprise eye blinking of said subject.

36. The method of claim 32, wherein said time correlating step comprises:
(a) time correlating one or more of said optical events with one or more involuntary driven physiological mechanical periodical or sequential movements of the subject.

37. The method of claim 36, wherein step (a) comprises:
time correlating one or more of said optical events with consecutive involuntary driven physiological mechanical periodical or sequential movements of the subject.

38. The method of claim 36, wherein step (a) comprises:
time correlating one or more of said optical events with non-consecutive involuntary driven physiological mechanical periodical or sequential movements of the subject.

39. The method of claim 33, wherein said involuntary driven physiological mechanical periodical or sequential movements of the subject comprises sequential finger tapping by said subject.

40. The method of claim 33, wherein said involuntary driven physiological mechanical periodical or sequential movements of the subject comprises walking gait or arm-hand swinging of said subject.

41. The method of claim 32, wherein said time correlating step involves initialization of said optical events.

42. The method of claim 32, wherein said time correlating step involves the duration span of said optical events, and wherein extraction of information during an early perceptual act of said optical events, may result in generation of a feedforward prediction about time durations among imminent sequential motoric movements in the said subject.

43. The method of claim 1, further comprising:
producing and generating fluctuations in said optical events.

44. The method of claim 43, wherein said producing and generating step comprises:
producing and generating random fluctuations.

45. The method of claim 43, wherein said producing and generating step comprises:
producing and generating periodic fluctuations.

46. The method of claim 43, wherein said producing and generating step comprises:
producing and generating fluctuations each comprising a periodical component and a random component.

47. The method of claim 43, wherein said producing and generating step comprises:
producing and generating fluctuations in said optical events to increase reactivity of magnocellular activity towards transient stimuli.

48. The method of claim 43, wherein said fluctuations are variable.

49. The method of claim 48, wherein said fluctuations are intrinsically variable.

50. The method of claim 48, wherein said fluctuations approximate intrinsically variable fluctuations.

51. The method of claim 43, wherein said producing and generating step comprises:
producing and generating fluctuations in said optical events in the spatial domain of the perceptual visual field of said subject.

52. The method of claim 43, wherein said producing and generating step comprises:
producing and generating temporal fluctuations in said optical events.

53. The method of claim 43, wherein said producing and generating step comprises:
producing and generating spatiotemporal fluctuations in said optical events.

54. The method of claim 43, wherein said producing and generating step comprises:
controlling one or more of said photic energetic parameters to produce and generate said fluctuations.

55. The method of claim 43, wherein said producing and generating step comprises:
controlling one or more of said photic perceptual attributes to produce and generate said fluctuations.

56. The method of claim 43, wherein said producing and generating step comprises:
controlling one or more of said photic energetic parameters and one or more of said photic perceptual attributes to produce and generate said fluctuations.

57. The method of claim 1, wherein step (2) comprises:
generating optical events that are less than 250 milliseconds in duration.

58. The method of claim 1, wherein step (2) comprises:
generating optical events that are less than 200 milliseconds in duration.

59. The method of claim 1, wherein step (2) comprises:
organizing a plurality of said optical events that together with intrinsic variable physiological mechanical activity in said subject, triggers fluctuations in an optical image within the perceptual visual field of the said subject, such that a complex optical flow is generated.

60. The method of claim 59, wherein said optical events are constrained to generate a simple optical flow.

61. The method of claim 60, wherein said simple optical flow comprises one or more perceptual arrays each comprising one or more optical events moving in said perceptual visual field of said subject.

62. The method of claim 61, wherein the optical events in the same perceptual array includes a single point of entrance into said perceptual visual field, a single point of departure from said perceptual visual field, and perceptually follows the same path.

63. The method of claim 61, wherein optical events in the same perceptual array have the same perceptual orientation.

64. The method of claim 61, wherein one or more optical events in the same perceptual array reverses perceptual orientation when moving across said perceptual visual field.

65. The method of claim 61, wherein one or more optical events in the same perceptual array reverses perceptual orientation when moving across said perceptual visual field in a time span less than 200 milliseconds.

66. The method of claim 61, wherein one or more optical events in the same perceptual array reverses perceptual orientation when moving across said perceptual visual field in a time span less than 250 milliseconds.

67. The method of claim 60, wherein said simple optical flow is generated by:
n perceptual arrays, at least partially displayed in said perceptual visual field; and
m optical events moving in each array;
wherein optical events of each perceptual array perceptually emerge and depart through a given pair of points in said perceptual visual field.

68. The method of claim 67, further comprising:
changing at least one of n, m, and said pair of points for each array while maintaining said simple optical flow as simple translational motion inside said perceptual visual field.

69. The method of claim 68, wherein said simple translatiional motion comprises 1-D translational or some forms of planar motion.

70. The method of claim 1, wherein said optical events comprise ground states and excited ground states, each ground state comprising a default condition of an optical event, step (2) comprising:
varying a ground state to generate an excited ground state.

71. The method of claim 70, wherein step (2) comprises:
varying the entire graphical appearance of said ground states.

72. The method of claim 70, wherein step (2) comprises:
varying a size of said ground states.

73. The method of claim 70, wherein step (2) comprises:
varying sizes of graphical components of said ground states.

74. The method of claim 70, wherein step (2) comprises:
varying a number of graphical components of said ground states.

75. The method of claim 70, wherein step (2) comprises:
varying one or more of
(a) the entire graphical appearance of said ground states;
(b) a size of said ground states;
(c) varying sizes of graphical components of said ground states; and
(d) varying a number of graphical components of said ground states.

76. The method of claim 1, wherein said optical events comprise ground states and excited ground states, step (2) comprising:
selecting graphical components of said ground states.

77. The method of claim 76, wherein said selecting step comprises:
selecting, for said graphical components, indicia that diminish potential for associative learning.

78. The method of claim 76, wherein said selecting step comprises:
selecting, for said graphical components, indicia that triggers pre-attentive cueing.

79. The method of claim 76, wherein said selecting step comprises:
selecting, for said graphical components, indicia that triggers imminent ballistic movements in the said subject.

80. The method of claim 1, wherein said optical events comprise ground states and excited ground states, step (2) comprising:
generating one or more ground states each correlated to at least some physiological mechanical periodical or sequential movement of the subject.

81. The method of claim 1, wherein said optical events comprise ground states and excited ground states, step (2) comprising:
varying said ground states.

82. The method of claim 81, wherein said varying step comprises:
varying photic energetic parameters of said ground states.

83. The method of claim 82, wherein said photic energetic parameters include one or more of wavelength, amplitude, intensity, phase, coherence, polarization, hue, brightness, and saturation.

84. The method of claim 81, wherein said varying step comprises:
selecting the rate of variation of one or more of said photic energetic parameters of said ground states.

85. The method of claim 81, wherein said varying step comprises:
selecting the order at which each of said photic energetic parameters of said ground states varies.

86. The method of claim 81, wherein said varying step comprises:
varying at least one of photic energetic parameters and graphical components of said ground states to modulate visual searching awareness in the said subject about time discreteness of perceptual pre-attentive cueing.

87. The method of claim 86, wherein visual searching awareness in said subject about said time discreteness triggers imminent motor movements by said subject which are not communicative.

88. The method of claim 81, further comprising:
varying the number of graphical components of a ground state.

89. The method of claim 81, wherein variation of ground states of a given optical event does not exceed 250 milliseconds.

90. The method of claim 81, wherein said varying step comprises:
(a) generating a first set comprising one or more ground states; and
(b) generating a second set comprising one or more excited ground states;
wherein steps (a) and (b) operate to generate said first and second sets according to a predefined sequence.

91. The method of claim 90, wherein said varying step further comprises:
(c) generating a third set comprising one or more ground states or excited ground states having attributes that differ from that of said first set or second set, respectively;
wherein steps (a), (b) and (c) operate to generate said first, second, and third sets according to said predefined sequence.

92. The method of claim 90, wherein said varying step further comprises:
(c) selecting said predefined sequence from a plurality of predefined sequences.

93. The method of claim 92, wherein step (c) is performed in accordance with a mathematical function.

94. The method of claim 90, wherein at least one of said first set and said second set is generated from one or more intrinsic variability sources.

95. The method of claim 81, wherein variation of ground states of a given optical event does not exceed 200 milliseconds.

96. The method of claim 1, wherein said optical events comprise ground states and excited ground states, step (2) comprising:
changing the size of said optical events as they move across the perceptual visual field of said subject.

97. The method of claim 1, wherein said optical events comprise ground states and excited ground states, step (2) comprising:
changing photic energetic parameters of said optical events as they move across the perceptual visual field of said subject.

98. The method of claim 1, wherein said optical events comprise ground states and excited ground states, step (2) comprising:
changing graphical components of said optical events as they move across the perceptual visual field of said subject.

99. The method of claim 1, wherein said optical events comprise ground states and excited ground states, step (2) comprising:
generating optical events having differing velocity vectors when entering the perceptual visual field of said subject.

100. The method of claim 1, wherein said optical events comprise ground states and excited ground states, step (2) comprising:
changing velocity vectors of said optical events as they move across the perceptual visual field of said subject.

101. The method of claim 1, wherein step (2) comprises:
varying one or more graphical components of one or more indicia distractors every n cycles, where n is variable.

102. The method of claim 1, wherein step (2) comprises:
varying one or more graphical components of one or more indicia distractors every n cycles, where n is variable.

103. The method of claim 1, wherein step (2) comprises:
varying one or more graphical components of one or more indicia targets every n cycles, where n is variable.

104. The method of claim 1, wherein step (2) comprises:
varying one or more graphical components of one or more indicia targets every n cycles, where n is variable.

105. The method of claim 1, wherein step (2) comprises:
causing hierarchical fluctuations to approximate one or more intrinsic variable sources.

106. The method of claim 1, wherein said optical field fluctuates in one or more of size, shape, intensity, color, location, saturation, time of display and theme.

107. A system to address early visual-sensory motor perception of a subject, comprising:
means for controlling photic energetic parameters and photic perceptual attributes to trigger pre-attentive cuing or increase reactivity in magnocellular activity towards transient visual stimuli of the subject; and
means for generating an optical field comprising optical events based on said photic energetic parameters and said photic perceptual attributes, wherein said optical field transforms into a simple optical flow in the perceptual visual field of said subject.

108. The system of claim 107, wherein said controlling means comprises:
means for controlling photic energetic parameters and photic perceptual attributes to trigger pre-attentive cuing and increase reactivity in magnocellular activity towards transient visual stimuli of the subject.

109. The system of claim 107, wherein said photic energetic parameters comprise light array energetic features.

110. The system of claim 109, wherein said light array energetic features comprise at least one or more of wavelength, amplitude, intensity, phase, polarization, coherence, hue, brightness, and saturation.

111. The system of claim 109, wherein said light array energetic features cause motor activity in said subject that can be delayed or inhibited by said subject.

112. The system of claim 111, wherein said motor activity is communicative.

113. The system of claim 112, wherein said motor activity comprises one or more of facial movements, eye movements, finger pointing, and verbal reports by said subject.

114. The system of claim 109, wherein said light array energetic features may trigger imminent ballistic movements in said subject when at least intensity of said light array energetic features is substantial.

115. The system of claim 107, wherein said photic perceptual attributes include the spatiotemporal patterning of said optical events.

116. The system of claim 115, wherein said spatiotemporal patterning is perceivable by said subject, and comprises one or more of perceivable changes in at least motion, location, direction, duration, and orientation of said optical events.

117. The system of claim 116, wherein said motion comprises simple motion.

118. The system of claim 117, wherein said simple motion comprises 1-D translational or some forms of planar motion.

119. The system of claim 117, wherein said simple motion comprises motion that does not cause self-motion by said subject, or does not cause an ordinary discriminatory perceptual act by said subject of object motion towards or away of said subject.

120. The system of claim 117, wherein said simple motion comprises implicit awareness about motion that does not cause information to be processed by ordinary perception in the said subject.

121. The system of claim 115, wherein said spatiotemporal patterning of said optical events trigger imminent ballistic movements in body parts of said subject.

122. The system of claim 121, wherein said imminent ballistic movements comprises body part mechanical movements.

123. The system of claim 122, wherein said body part mechanical movements are perceptually physically distributed along the entire body of said subject.

124. The system of claim 122, wherein said body part mechanical movements are target organs and muscles physically distributed along the visceral space of said subject.

125. The system of claim 122, wherein said body part mechanical movements include one or more arm movements for reaching, finger aperture movements, hand movements for grabbing, eye saccades movements for orienting, eye smooth pursue movements, head movements, chewing movements, neck movements and waist movements.

126. The system of claim 121, wherein said imminent ballistic movements are mechanical movements of one or more body parts in egocentric space of said subject.

127. The system of claim 126, wherein said imminent ballistic movements comprise proximal distal movements in reachable space of said subject, that cannot be delayed, that are uninterruptible once initiated, that are non-communicative, and that occur in a time span of a pre-attentive time event.

128. The system of claim 121, wherein said imminent ballistic movements comprise N sequential body part mechanical movements, which collectively fulfil an imminent motoric goal.

129. The system of claim 121, wherein said controlling and generating means comprise:
means for triggering said imminent ballistic movements to facilitate extraction and integration of information about various egocentric spaces of said subject via early perception.

130. The system of claim 121, wherein said controlling and generating means comprise:
means for triggering said imminent ballistic movements to facilitate extraction and transformation of information about various egocentric spaces of said subject via early perception.

131. The system of claim 121, wherein said controlling and generating means comprise:
means for triggering said imminent ballistic movements to increase transient stimuli reactivity in magnocellular activity of the subject.

132. The system of claim 121, wherein said controlling and generating means comprise:
means for triggering said imminent ballistic movements to effectively guide sensory motor behaviour of said subject.

133. The system of claim 107, further comprising:
means for modulating control of said photic energetic parameters and said photic perceptual attributes to increase magnocellular reactivity towards extracting information from early motion perception without cognitive awareness of said subject.

134. The system of claim 133, wherein said modulating means comprises:
means for regulating participation of said photic energetic parameters and said photic perceptual attributes in generating said optical events.

135. The system of claim 134, wherein said regulating means comprises:
means for regulating participation of said photic energetic parameters and said photic perceptual attributes in generating said optical events to control energetic impact of said optical events.

136. The system of claim 134, wherein said regulating means comprises:
means for regulating participation of said photic energetic parameters and said photic perceptual attributes in generating said optical events to modulate early perceptual spatiotemporal influences of said optical events.

137. The system of claim 107, wherein said optical events comprise ground states and excited ground states.

138. The system of claim 107, further comprising:
means for time correlating said optical events based on feedback from said subject.

139. The system of claim 138, wherein said time correlating means comprises:
means for time correlating said optical events with involuntary driven physiological mechanical periodical or sequential movements of the subject.

140. The system of claim 139, wherein said involuntary driven physiological mechanical periodical or sequential movements of the subject comprise at least one or more of the cyclical movement of one or more of the heart and lungs of said subject.

141. The system of claim 139, wherein said involuntary driven physiological mechanical periodical or sequential movements of the subject comprise eye blinking of said subject.

142. The system of claim 139, wherein said time correlating means comprises:
second time correlating means for time correlating one or more of said optical events with one or more involuntary driven physiological mechanical periodical or sequential movements of the subject.

143. The system of claim 142, wherein second time correlating means comprises:
means for time correlating one or more of said optical events with consecutive involuntary driven physiological mechanical periodical or sequential movements of the subject.

144. The system of claim 142, wherein second time correlating means comprises:
means for time correlating one or more of said optical events with non-consecutive involuntary driven physiological mechanical periodical or sequential movements of the subject.

145. The system of claim 139, wherein said involuntary driven physiological mechanical periodical or sequential movements of the subject comprises sequential finger tapping by said subject.

146. The system of claim 139, wherein said involuntary driven physiological mechanical periodical or sequential movements of the subject comprises walking gait or arm-hand swinging of said subject.

147. The system of claim 138, wherein said time correlating means involves initialization of said optical events.

148. The system of claim 138, wherein said time correlating means involves the duration span of said optical events, and wherein extraction of information during an early perceptual act of said optical events, may result in generation of a feedforward prediction about time durations among imminent sequential motoric movements in the said subject.

149. The system of claim 107, further comprising:
means for producing and generating fluctuations in said optical events.

150. The system of claim 149, wherein said producing and generating means comprises:
means for producing and generating random fluctuations.

151. The system of claim 149, wherein said producing and generating means comprises:
means for producing and generating periodic fluctuations.

152. The system of claim 149, wherein said producing and generating means comprises:
means for producing and generating fluctuations each comprising a periodical component and a random component.

153. The system of claim 149, wherein said producing and generating means comprises:
means for producing and generating fluctuations in said optical events to increase reactivity of magnocellular activity towards transient stimuli.

154. The system of claim 149, wherein said fluctuations are variable.

155. The system of claim 154, wherein said fluctuations are intrinsically variable.

156. The system of claim 154, wherein said fluctuations approximate intrinsically variable fluctuations.

157. The system of claim 149, wherein said producing and generating means comprises:
means for producing and generating fluctuations in said optical events in the spatial domain of the perceptual visual field of said subject.

158. The system of claim 149, wherein said producing and generating means comprises:
means for producing and generating temporal fluctuations in said optical events.

159. The system of claim 149, wherein said producing and generating means comprises:
means for producing and generating spatiotemporal fluctuations in said optical events.

160. The system of claim 149, wherein said producing and generating means comprises:
means for controlling one or more of said photic energetic parameters to produce and generate said fluctuations.

161. The system of claim 149, wherein said producing and generating means comprises:
means for controlling one or more of said photic perceptual attributes to produce and generate said fluctuations.

162. The system of claim 149, wherein said producing and generating means comprises:
means for controlling one or more of said photic energetic parameters and one or more of said photic perceptual attributes to produce and generate said fluctuations.

163. The system of claim 107, wherein said generating means comprises:
means for generating optical events that are less than 250 milliseconds in duration.

164. The system of claim 107, wherein said generating means comprises:
means for generating optical events that are less than 200 milliseconds in duration.

165. The system of claim 107, wherein said generating means comprises:
means for organizing a plurality of said optical events that together with intrinsic variable physiological mechanical activity in said subject, triggers fluctuations in an optical image within the perceptual visual field of the said subject, such that a complex optical flow is generated.

166. The system of claim 165, wherein said optical events are constrained to generate a simple optical flow.

167. The system of claim 166, wherein said simple optical flow comprises one or more perceptual arrays each comprising one or more optical events moving in said perceptual visual field of said subject.

168. The system of claim 167, wherein the optical events in the same perceptual array includes a single point of entrance into said perceptual visual field, a single point of departure from said perceptual visual field, and perceptually follows the same path.

169. The system of claim 167, wherein optical events in the same perceptual array have the same perceptual orientation.

170. The system of claim 167, wherein one or more optical events in the same perceptual array reverses perceptual orientation when moving across said perceptual visual field.

171. The system of claim 167, wherein one or more optical events in the same perceptual array reverses perceptual orientation when moving across said perceptual visual field in a time span less than 200 milliseconds.

172. The system of claim 167, wherein one or more optical events in the same perceptual array reverses perceptual orientation when moving across said perceptual visual field in a time span less than 250 milliseconds.

173. The system of claim 166, wherein said simple optical flow is generated by:
n perceptual arrays, at least partially displayed in said perceptual visual field; and
m optical events moving in each array;
wherein optical events of each perceptual array perceptually emerge and depart through a given pair of points in said perceptual visual field.

174. The system of claim 173, further comprising:
means for changing at least one of n, m, and said pair of points for each array while maintaining said simple optical flow as simple translational motion inside said perceptual visual field.

175. The system of claim 174, wherein said simple translational motion comprises 1-D translational or some forms of planar motion.

176. The system of claim 107, wherein said optical events comprise ground states and excited ground states, each ground state comprising a default condition of an optical event, said generating means comprising:
means for varying a ground state to generate an excited ground state.

177. The system of claim 176, wherein said generating means comprises:
means for varying the entire graphical appearance of said ground states.

178. The system of claim 176, wherein said generating means comprises:
means for varying a size of said ground states.

179. The system of claim 176, wherein said generating means comprises:
means for varying sizes of graphical components of said ground states.

180. The system of claim 176, wherein said generating means comprises:
means for varying a number of graphical components of said ground states.

181. The system of claim 176, wherein said generating means comprises:
means for varying one or more of
(a) the entire graphical appearance of said ground states;
(b) a size of said ground states;
(c) varying sizes of graphical components of said ground states; and
(d) varying a number of graphical components of said ground states.

182. The system of claim 107, wherein said optical events comprise ground states and excited ground states, said generating means comprising:
means for selecting graphical components of said ground states.

183. The system of claim 182, wherein said selecting means comprises:
means for selecting, for said graphical components, indicia that diminish potential for associative learning.

184. The system of claim 182, wherein said selecting means comprises:
means for selecting, for said graphical components, indicia that triggers pre-attentive cueing.

185. The system of claim 182, wherein said selecting means comprises:
means for selecting, for said graphical components, indicia that triggers imminent ballistic movements in the said subject.

186. The system of claim 107, wherein said optical events comprise ground states and excited ground states, said generating means comprising:
  means for generating one or more ground states each correlated to at least some physiological mechanical periodical or sequential movement of the subject.

187. The system of claim 107, wherein said optical events comprise ground states and excited ground states, said generating means comprising:
  means for varying said ground states.

188. The system of claim 187, wherein said varying means comprises:
  means for varying photic energetic parameters of said ground states.

189. The system of claim 188, wherein said photic energetic parameters include one or more of wavelength, amplitude, intensity, phase, coherence, polarization, hue, brightness, and saturation.

190. The system of claim 187, wherein said varying means comprises:
  means for selecting the rate of variation of one or more of said photic energetic parameters of said ground states.

191. The system of claim 187, wherein said varying means comprises:
  means for selecting the order at which each of said photic energetic parameters of said ground states varies.

192. The system of claim 187, wherein said varying means comprises:
  means for varying at least one of photic energetic parameters and graphical components of said ground states to modulate visual searching awareness in the said subject about time discreteness of perceptual pre-attentive cueing.

193. The system of claim 192, wherein visual searching awareness in said subject about said time discreteness triggers imminent motor movements by said subject which are not communicative.

194. The system of claim 187, further comprising:
  means for varying the number of graphical components of a ground state.

195. The system of claim 187, wherein variation of ground states of a given optical event does not exceed 250 milliseconds.

196. The system of claim 187, wherein said varying means comprises:
  first means for generating a first set comprising one or more ground states; and
  second means for generating a second set comprising one or more excited ground states;
  wherein said first and second means operate to generate said first and second sets according to a predefined sequence.

197. The system of claim 196, wherein said varying means further comprises:
  third means for generating a third set comprising one or more ground states or excited ground states having attributes that differ from that of said first set or second set, respectively;
  wherein said first, second, and third means operate to generate said first, second, and third sets according to said predefined sequence.

198. The system of claim 196, wherein said varying means further comprises:
  means for selecting said predefined sequence from a plurality of predefined sequences.

199. The system of claim 198, wherein said selecting means operates in accordance with a mathematical function.

200. The system of claim 196, wherein at least one of said first set and said second set is generated from one or more intrinsic variability sources.

201. The system of claim 183, wherein variation of ground states of a given optical event does not exceed 200 milliseconds.

202. The system of claim 107, wherein said optical events comprise ground states and excited ground states, said generating means comprising:
  means for changing the size of said optical events as they move across the perceptual visual field of said subject.

203. The system of claim 107, wherein said optical events comprise ground states and excited ground states, said generating means comprising:
  means for changing photic energetic parameters of said optical events as they move across the perceptual visual field of said subject.

204. The system of claim 107, wherein said optical events comprise ground states and excited ground states, said generating means comprising:
  means for changing graphical components of said optical events as they move across the perceptual visual field of said subject.

205. The system of claim 107, wherein said optical events comprise ground states and excited ground states, said generating means comprising:
  means for generating optical events having differing velocity vectors when entering the perceptual visual field of said subject.

206. The system of claim 107, wherein said optical events comprise ground states and excited ground states, said generating means comprising:
  means for changing velocity vectors of said optical events as they move across the perceptual visual field of said subject.

207. The system of claim 107, wherein said generating means comprises:
  means for varying one or more graphical components of one or more indicia distractors every n cycles, where n is variable.

208. The system of claim 180, wherein said generating means comprises:
  means for varying one or more graphical components of one or more indicia distractors every n cycles, where n is variable.

209. The system of claim 107, wherein said generating means comprises:
  means for varying one or more graphical components of one or more indicia targets every n cycles, where n is variable.

210. The system of claim 180, wherein said generating means comprises:
  means for varying one or more graphical components of one or more indicia targets every n cycles, where n is variable.

211. The system of claim 107, wherein said generating means comprises:
  means for causing hierarchical fluctuations to approximate one or more intrinsic variable sources.

212. The system of claim 107, wherein said optical field fluctuates in one or more of size, shape, intensity, color, location, saturation, time of display and theme.

* * * * *